US010125363B2

(12) United States Patent
Montefeltro et al.

(10) Patent No.: US 10,125,363 B2
(45) Date of Patent: Nov. 13, 2018

(54) COMPOSITIONS AND METHODS FOR THE TREATMENT OF PARKINSON DISEASE BY THE SELECTIVE DELIVERY OF OLIGONUCLEOTIDE MOLECULES TO SPECIFIC NEURON TYPES

(71) Applicant: nLife Therapeutics, S.L., Armilla, Granada (ES)

(72) Inventors: Andrés Pablo Montefeltro, Barcelona (ES); Gabriel Alvarado Urbina, Nepean (CA); Analia Bortolozzi Biassoni, Barcelona (ES); Francesc Artigas Pérez, Barcelona (ES); Miquel Vila Bover, Barcelona (ES); Maria del Carmen Carmona Orozco, Terrassa (ES)

(73) Assignee: nLife Therapeutics, S.L., Armilla, Granada (ES)

( * ) Notice: Subject to any disclaimer, the term of this patent is extended or adjusted under 35 U.S.C. 154(b) by 0 days.

(21) Appl. No.: 14/803,811

(22) Filed: Jul. 20, 2015

(65) Prior Publication Data
US 2016/0083726 A1 Mar. 24, 2016

Related U.S. Application Data

(63) Continuation of application No. 14/065,024, filed on Oct. 28, 2013, now Pat. No. 9,084,825.

(60) Provisional application No. 61/719,284, filed on Oct. 26, 2012.

(30) Foreign Application Priority Data

Oct. 26, 2012 (EP) ..................................... 12382414

(51) Int. Cl.
*C12N 15/113* (2010.01)
*A61K 31/7105* (2006.01)
*A61K 47/55* (2017.01)

(52) U.S. Cl.
CPC ........ *C12N 15/113* (2013.01); *A61K 31/7105* (2013.01); *A61K 47/55* (2017.08); *C12N 2310/14* (2013.01)

(58) Field of Classification Search
CPC ........ A61K 47/51; A61K 47/55; A61K 48/00; C12N 15/113; C12N 2310/14
USPC ........... 435/6.1, 6.11, 6.16, 91.1, 91.31, 325, 435/368, 375, 455, 458, 463; 514/44, 1, 514/2; 536/23.1, 24.5; 535/24.31
See application file for complete search history.

(56) References Cited

U.S. PATENT DOCUMENTS

| 5,176,996 A | 1/1993 | Hogan et al. |
| 5,256,775 A | 10/1993 | Froehler |
| 5,264,564 A | 11/1993 | Matteucci |
| 9,084,825 B2 | 7/2015 | Montefeltro et al. |
| 2008/0139799 A1 | 6/2008 | Khvorova et al. |
| 2010/0221735 A1* | 9/2010 | Youdim ............... C12Q 1/6883 435/6.16 |
| 2012/0129912 A1 | 5/2012 | Mouradian et al. |
| 2012/0322991 A1* | 12/2012 | Montefeltro ..... A61K 47/48046 536/23.1 |
| 2014/0005252 A1* | 1/2014 | Bennett ................ C12N 15/113 514/44 A |
| 2014/0315795 A1 | 10/2014 | Carmona Orozco et al. |

FOREIGN PATENT DOCUMENTS

| EP | 0 076 669 A1 | 4/1983 |
| WO | WO 88/09810 A1 | 12/1988 |
| WO | WO 89/10134 A1 | 11/1989 |
| WO | WO 97/26270 A2 | 7/1997 |
| WO | WO 2007/050789 A2 | 5/2007 |
| WO | WO 2007050789 | * 5/2007 |
| WO | WO 2007/107789 A2 | 9/2007 |
| WO | WO 2009/079399 A2 | 6/2009 |
| WO | WO 2009/079790 A1 | 7/2009 |
| WO | WO 2011/087804 A2 | 7/2011 |
| WO | WO 2011/131693 A2 | 10/2011 |
| WO | WO 2012/027713 A2 | 3/2012 |

OTHER PUBLICATIONS

Wersinger et al, FASEB J., vol. 17, pp. 2151-2153 (2003).*
Wersinger et al, Neuroscience Lett., vol. 340, pp. 189-192 (2003).*
Negus et al, J. Pharmacol. & Exp. Therapeutics, vol. 291 No. 1, pp. 60-69 (1999).*
Gardner et al, Neuropharm. vol. 51, pp. 993-1003 (2006).*
Silva et al (Organic Lett., vol. 9, No. 8, pp. 1433-1436 (2007).*
Altschul, S.F., et al., "Basic Local Alignment Search Tool," *J. Mol. Biol.* 215:403-410, Academic Press Limited, England (1990).
Beaucage S.L. and Iyer, R.P., "The Functionalization of Oligonucleotides Via Phosphoramidite Derivatives," *Tetrahedron* 49(10):1925-1963, Pergamon Press Ltd., England (1993).

(Continued)

Primary Examiner — Jane J Zara
(74) Attorney, Agent, or Firm — Sterne, Kessler, Goldstein & Fox P.L.L.C.

(57) ABSTRACT

The invention provides a conjugate comprising (i) a selectivity agent which binds specifically to one or more neurotransmitter transporters selected from the group consisting of a dopamine transporter (DAT), serotonin transporter (SERT) or a norepinephrine transporter (NET) and (ii) a nucleic acid capable of specifically binding to a target molecule which is expressed in the same cell as the neurotransmitter transporter wherein said target molecule is α-synuclein or the mRNA encoding α-synuclein. The conjugates of the present invention are useful for the delivery of the nucleic acid to a cell of interest and thus, for the treatment of diseases which require a down-regulation of the protein encoded by the target nucleic acid as well as for the delivery of imaging agents to the cells for diagnostic purposes.

23 Claims, 6 Drawing Sheets
Specification includes a Sequence Listing.

(56) References Cited

OTHER PUBLICATIONS

Bolden-Watson, C. and Richelson, E., "Blockade by newly-developed antidepressants of biogenic amine uptake into rat brain synaptosomes," *Life Sciences* 52:1023-1029, Pergamon Press Ltd., England (1993).
Crooke, S.T., et al., "Pharmacokinetic Properties of Several Novel Oligonucleotide Analogs in mice," *The Journal of Pharmacology and Experimental Therapeutics* 277(2):923-937, The American Society for Pharmacology and Experimental Therapeutics, United States (1996).
Doxakis, E., "Post-transcriptional Regulation of α-Synuclein Expression by mir-7 and mir-153," *J. Biol. Chem.* 285(17):12726-12734, The American Society for Biochemistry and Molecular Biology, Inc., United States (2010).
Egholm, M., et al., "PNA hybridizes to complementary oligonucleotides obeying the Watson-Crick hydrogen-bonding rules," *Nature* 365:566-568, Nature Publishing Group, England (1993).
Hélène, C., "The anti-gene strategy: control of gene expression by triplex-forming-oligonucleotides," *Anti-Cancer Drug Design* 6:569-584, Macmillan Press Ltd., United States (1991).
Junn, E., et al., "Repression of α-synuclein expression and toxicity by microRNA-7," *Proc Natl Acad Sci USA* 106(31):13052-13057, National Academy of Sciences, United States (2009).
Kabanov, A.V., et al., "A new class of antivirals: antisense oligonucleotides combined with a hydrophobic substituent effectively inhibit influenza virus reproduction and synthesis of virus-specific proteins in MDCK cells," *FEBS Lett* 259(2):327-330, Elsevier Science Publishers B.V., Netherlands (1990).
Koe, B.K., et al., "Sertraline, 1S,4S-N-Methyl-4-(3,4-Dichlorophenyl)-1,2,3,4-Tetrahydro-1-Naphthylamine, a New Uptake Inhibitor with Selectivity for Serotonin," *J Pharmacol Exp Ther* 226(3):686-700, The American Society for Pharmacology and Experimental Therapeutics, United States (1983).
Kula, N.S., et al., "Effects of N-substituted phenyltetrahydropyridines on cerebral high-affinity synaptosomal uptake of dopamine and other monoamines in several mammalian species," *Life Sciences* 34:2567-2575, Pergamon Press Ltd., England (1984).
Kumar, P., et al., "Transvascular delivery of a small interfering RNA to the central nervous system," *Nature* 448(7149):39-43, Nature Publishing Group, England (2007).
Lapa, G.B., "Molecular-biological problems of drug design and mechanism of drug action," *Pharmaceutical Chemistry Journal* 45(6):323-328, Springer Science + Business Media, Inc., United States (2011).
Lemaitre, M., et al., "Specific antiviral activity of a poly-(L-lysine)-conjugated oligodeoxyribonucleotide sequence complementary to vesicular stomatitis virus N protein mRNA initiation site," *Proc Natl Acad Sci USA* 84:648-652, National Academy of Sciences, United States (1987).
Letsinger, R.L., et al., "Cholesteryl-conjugated oligonucleotides: Synthesis, properties, and activity as inhibitors of replication of human immunodeficiency virus in cell culture," Proc Nati Acad Sci USA 86:6553-6556, National Academy of Sciences, United States (1989).
Liu, Y., et al., "Membrane trafficking of neurotransmitter transporters in the regulation of synaptic transmission," *Trends Cell Biol* 9(9):356-363, Elsevier Science Ltd., England (1999).
Manoharan, M., et al., "Chemical Modifications to Improve Uptake and Bioavailability of Antisense Oligonucleotides," *Annals New York Academy of Sciences* 660:306-309, United States (1992).
Manoharan, M., et al., "Introduction of a lipophilic thioether tether in the minor groove of nucleic acids for antisense applications," *Bioorganic & Medicinal Chemistry Letters* 3(12):2765-2770, Pergamon Press Ltd., England (1993).
Manoharan, M., et al., "Cholic acid-oligonucleotide conjugates for antisense applications," *Bioorganic & Medicinal Chemistry Letters* 4(8):1053-1060, Elsevier Science Ltd., England (1994).
Manoharan, M., et al., "Lipidic Nucleic Acids," *Tetrahedron Letters* 36(21):3651-3654, Elsevier Science Ltd., England (1995).

Manoharan, M., et al., "Oligonucleotide conjugates: alteration of the pharmacokinetic properties of antisense agents," *Nucleosides & Nucleotides* 14(35):969-973, Marcel Dekker, Inc., United States (1995).
Mishra, R.K., et al., "Improved leishmanicidal effect of phosphorotioate antisense oligonucleotides by LDL-mediated delivery," *Biochimica et Biophysica Acta* 1264:229-237, Elsevier Science B.V., Netherlands (1995).
Oberhauser, B. and Wagner, E., "Effective incorporation of 2'-O-methyl-oligoribonucleotides into liposomes and enhanced cell association through modification with thiocholesterol," *Nucleic Acids Research* 20(3):533-538, Oxford University Press, England (1992).
Oney, S., et al., "Antidote-Controlled Platelet Inhibition Targeting von Willebrand Factor with Aptamers," *Oligonucleotides* 17:265-274, Mary Ann Liebert, Inc., United States (2007).
Perry-O'Keefe, H., et al., "Peptide nucleic acid pre-gel hybridization: An alternative to Southern hybridization," *Proc Natl Acad Sci USA* 93:14670-14675, National Academy of Sciences, United States (1996).
Que-Gewirth, N.S. and Sullenger, B.A., "Gene therapy progress and prospects: RNA aptamers," *Gene Therapy* 14:283-291, Nature Publishing Group, England (2007).
Saison-Behmoaras, T., et al., "Short modified antisense oligonucleotides directed against Ha-*ras* point mutation induce selective cleavage of the mRNA and inhibit T24 cells proliferation," *The EMBO Journal* 10(5):1111-1118, Oxford University Press, England (1991).
Schloss, P., et al., "Neurotransmitter transporters: new members of known families," *Curr Opin Cell Biol* 6:595-599, Current Biology Ltd., England (1994).
Shamah, S.M., et al., "Complex Target SELEX," *Accounts of Chemical Research* 41(1):130-138, American Chemical Society, United States (2008).
Shea, R.G., et al., "Synthesis, hybridization properties and antiviral activity of lipid-oligodeoxynucleotide conjugates," *Nucleic Acids Research* 18(13):3777-3783, Oxford University Press, England (1990).
Spilsberg, B., et al., "Reconstitution of active diphtheria toxin based on a hexahistidine tagged version of the B-fragment produced to high yields in bacteria," *Toxicon* 46:900-906, Elsevier Ltd., England (2005).
Stein, C.A. and Cohen, J.S., "Oligodeoxynucleotides as Inhibitors of Gene Expression: A Review," *Cancer Res* 48:2659-2668, American Association for Cancer Research, United States (1988).
Subbarao, N.K., et al., "pH-Dependent Bilayer Destabilization by an Amphipathic Peptide," *Biochemistry* 26:2964-2972, American Chemical Society, United States (1987).
Svinarchuk, F.P., et al., "Inhibition of HIV proliferation in MT-4 cells by antisense oligonucleotide conjugated to lipophilic groups," *Biochimie* 75:49-54, Société française de biochimie et biologie moléculaire/Elsevier, France (1993).
Thompson, J.D., et al., "Clustal W: improving the sensitivity of progressive multiple sequence alignment through sequence weighting, position-specific gap penalties and weight matrix choice," *Nucleic Acids Research* 22(22):4673-4680, Oxford University Press, England (1994).
Turk, M.J., et al., "Characterization of a novel pH-sensitive peptide that enhances drug release from folate-targeted liposomes at endosomal pHs," *Biochimica et Biophysica Acta* 1559:56-68, Elsevier Science B.V., Netherlands (2002).
Van Der Krol, A.R., et al., "Modulation of Eukaryotic Gene Expression by Complementary RNA or DNA Sequences," *BioTechniques* 6(10):958-976, Eaton Pub. Co., United States (1988).
Vogel, K., et al., "Peptide-Mediated Release of Folate-Targeted Liposome Contents from Endosomal Compartments," *Journal of the American Chemical Society* 118(7):1581-1586, American Chemical Society (1996).
Xia, C.-F., et al., "Intravenous siRNA of Brain Cancer with Receptor Targeting and Avidin-Biotin Technology," *Pharmaceutical Research* 24(12):2309-2316, Springer Science + Business Media, LLC, United States (2007).

(56) References Cited

OTHER PUBLICATIONS

Zon, G., "Oligonucleotide Analogues as Potential Chemotherapeutic Agents," *Pharmaceutical Research* 5(9):539-549, Plenum Publishing Corporation, United States (1988).
International Search Report for International Application No. PCT/EP2013/072410, European Patent Office, Rijswijk, Netherlands, dated Mar. 7, 2014.
Gardner, E.L., et al., "A slow-onset, long-duration indanamine monoamine reuptake inhibitor as a potential maintenance pharmacotherapy for psychostimulant abuse: effects in laboratory rat models relating to addiction," *Neuropharmacology* 51(5):993-1003, Pergamon Press, England (2006).
Negus, S.S., et al., "Effects of the long-acting monoamine reuptake inhibitor indatraline on cocaine self-administration in rhesus monkeys," *J. Pharmacol. Exp. Ther.* 291(1):60-69, American Society for Pharmacology and Experimental Therapeutics, United States (1999).
Silva Jr, L.F., et al., "Iodine(III)-promoted ring contraction of 1,2-dihydronaphthalenes: a diastereoselective total synthesis of (+/−)-indatraline," *Organic Letters* 9(8):1433-1436, American Chemical Society, United States (2007).
Wersinger, C. and Sidhu, A., "Attenuation of dopamine transporter activity by alpha-synuclein," *Neuroscience Letters* 340(3):189-192, Elsevier Scientific Publishers Ireland, Ireland (2003).
Wersinger, C., et al., "Modulation of dopamine transporter function by alpha-synuclein is altered by impairment of cell adhesion and by induction of oxidative stress," *FASEB Journal* 17(14):2151-2153, The Federation of American Societies for Experimental Biology, United States (2003).

\* cited by examiner

COMPOSITIONS AND METHODS FOR THE TREATMENT OF PARKINSON DISEASE BY THE SELECTIVE DELIVERY OF OLIGONUCLEOTIDE MOLECULES TO SPECIFIC NEURON TYPES

REFERENCE TO SEQUENCE LISTING SUBMITTED ELECTRONICALLY

The content of the electronically submitted sequence listing (Name: 3246_0010002_SequenceListing.txt; Size: 8 kilobytes; and Date of Creation: Aug. 19, 2015) is incorporated herein by reference in its entirety.

FIELD OF THE INVENTION

The present invention relates to conjugates comprising a nucleic acid specific for a target of interest and a group which allows the delivery of the nucleic acids to specific cells within the central nervous system by means of their affinity towards neurotransmitter transporter molecules on the surface of said cells.

BACKGROUND ART

The use of nucleic acids has proved effective for altering the state of a cell. The introduction of deoxyribonucleic acid (DNA) or ribonucleic acid (RNA) into a cell can be used to up- or down-regulate the expression of particular genes in the cell, thereby, impacting one or more biochemical pathways. Of the nucleic acid-based technologies used to alter cell physiology, RNA interference (RNAi) is the general term given for regulating the expression of genes at the post-transcriptional level in diversified organisms. RNAi gene silencing can be accomplished using homologous short (21-23 bp) dsRNA fragments known as short interfering or "siRNA." When a long dsRNA is introduced into a cell line, the cellular enzyme Dicer will cleave it into short interfering RNA (siRNA) molecules. This short interfering RNA molecule is now called the guided RNA. The guided RNA will guide the RNA-Induced-Silencing-Complex (RISC) to the homologous target mRNA. Once it forms a hybrid structure to the homologous mRNA sequence, the RISC will cleave the mRNA. As a result, protein that is encoded by the mRNA will no longer be produced, thereby causing the silencing of the gene. RNA interference refers to the process of sequence-specific post-transcriptional gene silencing in animals mediated by short interfering RNAs (siRNAs).

However, a major obstacle for the development of RNAi-based therapeutic approaches for brain pathologies is the blood-brain barrier (BBB). The brain is shielded against potentially toxic substances by the presence of two barrier systems: the blood-brain barrier (BBB) and the blood-cerebrospinal fluid barrier (BCSFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS. As a general rule, only small lipophilic molecules may pass across the BBB, i.e., from circulating systemic blood to brain. Many drugs that have a larger size or higher hydrophobicity show promising results in animal studies for treating CNS disorders.

Besides direct intrabrain administration, different strategies have been described for achieving gene silencing in the CNS by means of systemically-administered RNA interfering molecules. For instance, Kumar et al. (Nature, 2007, 448:39-44) have described conjugates of siRNA and a peptide derived from the rabies virus glycoprotein comprising a nonamer arginine and their ability to silence gene expression in the brain after intravenous injection. Xia et al. (Pharmaceutical Research, 2007, 24:2309-2316) have described conjugates comprising a biotinylated siRNA and a conjugate comprising avidin-anti-transferrin receptor antibody which are capable of silencing gene expression in the central nervous system after systemic delivery. WO200979790 describe conjugates comprising siRNA and a series of peptides collectively known as Angiopeps which are capable of crossing the blood-brain barrier by receptor-mediated transcytosis using the low-density lipoprotein receptor-related protein-1 (LRP-1) and which allows the delivery to the CNS of systemically administered conjugates comprising said peptides. WO2007107789 describes the use of compounds capable of causing RNA interference and which are specific for targets present in the CNS and the delivery to the CNS by the use of intranasal administration.

Several reports have speculated about conjugates to synuclein-specific silencing agents and different molecules which might help the translocation of the conjugate across cell membranes or across the blood brain barrier. For instance, WO2011087804 describes conjugates comprising an alpha-synuclein-specific siRNA and a peptide derived from rabies virus glycoprotein G, which allows the conjugate to cross the blood-brain barrier. WO2012027713 describes conjugates of alpha-synuclein-specific dsRNA and different moieties which enhance the activity, cellular distribution or uptake of the dsRNA such as lipid moieties (cholesterol), cholic acid, a thioether, a thiocholesterol, an aliphatic chain (e.g. dodecandiol or undecyl residues), a phospholipid, a polyamine or a polyethylene glycol chain, adamantane acetic acid, a palmityl moiety or an octadecylamine or hexylamino-carbonyloxycholesterol moiety. However, all these conjugates are intended for non-specific delivery across biological membranes or biological barriers but do not confer specificity towards the cells wherein synuclein is expressed.

However, while all these systems allow the delivery of systemically administered siRNAs to the CNS, they do not allow delivery to specific cell types within the brain. WO2011131693 (incorporated herein by reference) discloses conjugates comprising a nucleic acid which is complementary to a target nucleic acid sequence and which expression prevents or reduces expression of the target nucleic acid and a selectivity agent which is capable of binding with high affinity to a neurotransmitter transporter. These conjugates are useful for the delivery of a particular nucleic acid to a cell of interest.

The possibility of delivering siRNAs of known specificity to the central nervous system will be useful for the treatment of diseases which are caused by an undesired activity/expression of a given gene, including depression, cognitive disorders, Parkinson's disease, Alzheimer's disease, etc.

Parkinson's disease (PD) is a degenerative disorder of the central nervous system that often impairs the patient's motor skills, speech, and other functions. The symptoms of Parkinson's disease result from the greatly reduced activity of dopaminergic cells in the pars compacta region of the substantia nigra (SNpc). These neurons project to the striatum and their loss leads to alterations in the activity of the neural circuits within the basal ganglia that regulate movement, in essence an inhibition of the direct pathway and excitation of the indirect pathway. The direct pathway facilitates movement and the indirect pathway inhibits movement, thus the loss of these cells leads to a hypokinetic movement disorder. The lack of dopamine results in increased inhibition of the ventral anterior nucleus of the thalamus, which sends excitatory projections to the motor cortex, thus leading to hypokinesia.

PD is characterized by a progressive loss of dopaminergic neurons in the SNpc and the presence of intracellular inclusions designated as Lewy bodies (LB). Neurochemically, PD is marked by mitochondrial complex I dysfunction and increased indices of oxidative stress. Several pathogenic mechanisms have been proposed for PD including oxidative and nitrosative stress, mitochondrial dysfunction, protein misfolding and aggregation, and apoptosis. PD is mostly sporadic but some of the PD cases have been shown to be familial-linked. The first familial-linked PD gene identified was α-synuclein (α-syn) which in fact is the major component of LB in all PD patients. The normal function of α-synuclein is poorly understood. α-Synuclein can bind to lipids and, in neurons, is associated with presynaptic vesicles and the plasma membrane, possibly via lipid rafts. The deposited, pathological forms of α-synuclein are aggregated and show lower solubility than the normal protein. Three point mutations have been described to cause familial PD, but also duplications and triplications of the SNCA gene have been reported to be responsible for PD and Lewy body disease. Therefore, even without sequence variants, α-synuclein dosage can be causal for Lewy body disease.

α-Synuclein affects mitochondria and probably induces apoptosis. In fact, there is accumulating evidence for a close relationship between α-synuclein and oxidative damage: overexpression of mutant α-synuclein sensitizes neurons to oxidative stress and damage by dopamine and complex I inhibitors, resulting in increased protein carbonylation and lipid peroxidation in vitro and in vivo. Conversely, dysfunction of mitochondrial complex I has been associated to sporadic forms of PD. Complex I dependent oxidative damage and defective mitochondrial function is a main cause of neuronal degeneration and cell death in PD. Thus impaired mitochondrial function and ROS production increases the cytochrome c pool level in the mitochondrial intermembrane space, allowing its rapid release when the cell death agonist Bax is activated.

To sum up, the scenario in PD would be a situation of neuronal mitochondrial dysfunction with increase ROS production that on one hand would increase α-synuclein accumulation and on the other would activate Bax-mediated cell death. Further, α-synuclein accumulation, in turn, would increase cellular ROS production and induction of neuronal degeneration.

The most widely used treatment for PD is L-DOPA in various forms. However, only 1-5% of L-DOPA enters the dopaminergic neurons. The remaining L-DOPA is often metabolised to dopamine elsewhere, causing a wide variety of side effects. Dopa decarboxylase inhibitors like carbidopa and benserazide are also used for the treatment of PD since they help to prevent the metabolism of L-DOPA before it reaches the dopaminergic neurons and are generally given as combination preparations of carbidopa/levodopa and benserazide/levodopa. Moreover, dopamine agonists are moderately effective and act by stimulating some of the dopamine receptors. However, they cause the dopamine receptors to become progressively less sensitive, thereby eventually increasing the symptoms.

Antisense approaches might also be helpful, and have been reported to work in the rat and mouse brain. This approach is predicated on the idea that α-synuclein really is dispensable for CNS function in humans, as it appears to be in the mouse but perhaps even a modest decrease in protein levels would be enough to decrease PD progression.

However, despite the advances made in the development of PD therapeutics, there is still the need of alternative compounds which specifically are capable of preventing the reduced activity of dopaminergic cells in the pars compacta region of the substantia nigra.

SUMMARY OF THE INVENTION

The inventors of the present invention have identified different particular regions within the human alpha-synuclein mRNA sequence that, when targeted using silencing molecules, results in the cleavage of the alpha-synuclein mRNA. This has been shown by testing antisense oligonucleotides in an RNase-H-mediated assay and by testing down-regulation of the alpha-synuclein mRNA. Moreover, the gapmer version of the preferred silencing nucleic acid (cuccCTCCACTGTCuucu, SEQ ID NO:2) has been coupled to the triple reuptake inhibitor indatraline. The inventors have shown that indatraline is able to target an antisense oligonucleotide to cells expressing the serotonin 5-HT$_{1A}$ receptor when administered intranasally, and that indatraline is capable of targeting areas of the brain containing cells expressing a dopamine transporter (DAT) (e.g, the substantia nigra), to areas of the brain containing cells expressing a norepinephrine transporter NET (e.g. locus coeruleous) and to areas of the brain containing cells expressing a serotonin transporter SERT (e.g. raphe nuclei and dorsal raphe) as indicated by a fluorophore attached to indatraline. Moreover, the inventors have also shown that intranasal administration of the conjugate comprising indatraline and the preferred candidate gapmer results in a decrease of the levels of synuclein mRNA determined by in situ hybridization.

The silencing molecule according to the invention has some advantages. Firstly, it is specifically targeted to cells wherein the protein to be silenced is expressed, avoiding side effects due to the silencing of the protein in undesired locations. Secondly, the silencing molecule according to the invention is translocated across the cell membrane using a neurotransmitter transporter.

Thus, in a first aspect, the invention relates to a conjugate comprising:

i) at least one selectivity agent which binds specifically to one or more neurotransmitter transporters selected from the group consisting of a dopamine transporter (DAT), serotonin transporter (SERT) or a norepinephrine transporter (NET) and ii) at least one nucleic acid which is capable of specifically binding to a target molecule which is expressed in the same cell as the neurotransmitter transporter wherein said target molecule is α-synuclein or the mRNA encoding α-synuclein.

In a second aspect, the invention relates to a conjugate according to the invention for use in medicine.

In a further aspect, the invention relates to a conjugate according to the invention for use in the treatment or prevention of a disease associated with the deposition of Lewy bodies.

In a further aspect, the invention relates to a conjugate having the structure (III)

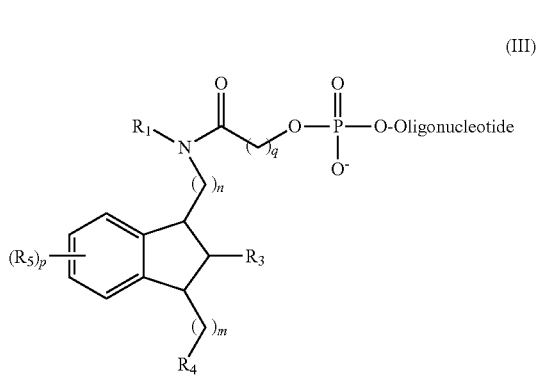

(III)

wherein n, m, p, q, R1, R3, R4 and R5 are as defined and wherein the oligonucleotide is a nucleic acid which is capable of specifically binding to a target molecule wherein said target molecule is alpha-synuclein or the mRNA encoding α-synuclein.

In a further aspect, the invention relates to a process comprising reacting a compound having the structure (V)

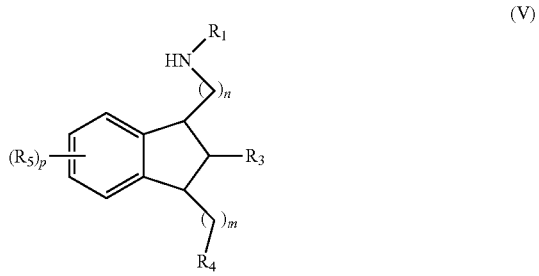

(V)

with a carboxymodified oligonucleotide having the formula (VI):

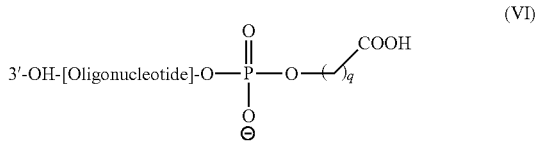

(VI)

In a further aspect, the invention relates to a compound having the structure (VI) wherein the oligonucleotide is a nucleic acid which is capable of specifically binding to a target molecule wherein said target molecule is alpha-synuclein or the mRNA encoding alpha-synuclein.

In a further aspect, the invention relates to a conjugate comprising
(i) at least one selectivity agent which binds specifically to one or more neurotransmitter transporters selected from the group consisting of a dopamine transporter (DAT), serotonin transporter (SERT) or a norepinephrine transporter (NET) and
(ii) an imaging agent.

In yet another aspect, the invention relates to a method for imaging a cell which expresses a neurotransmitter transporter which comprises contacting said cell with a conjugate according to the invention wherein the selectivity agent forming part of the conjugate binds specifically to the neurotransmitter transporter expressed by said cell These and other objects of the present invention will be further described in the detailed description section that follows, and they are not intended to be limiting of the present invention. Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise" and its variations are not intended to exclude other technical features, additives, components, or steps.

DETAILED DESCRIPTION OF THE INVENTION

Figure 1:
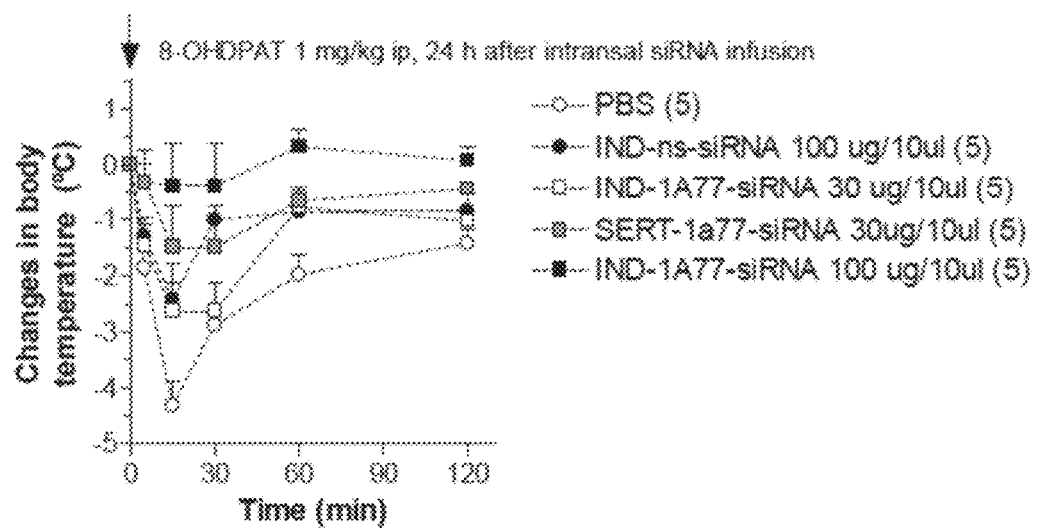
FIG. 1 shows the absence of hypothermia response induced by (R)-(+)-8-hydroxy-2-(di-n-propylamino)tetralin hydrobromide (8-OH-DPAT, selective 5-HT$_{1A}$R agonist) in mice having received intra-nasally an oligo anti-5HTIA with indatraline. Mice received: i) vehicle (PBS), ii) 100 µg indatraline nonsense siRNA (IND-ns-siRNA), iii) 30 µg indatraline-1A77 siRNA (IND-1A77-siRNA), iv) 30 µg sertraline-1a77 siRNA (SERT-1a77-siRNA) or v) 100 µg indatraline-1A77-siRNA (IND-1A77 siRNA). Body temperature was assessed 5 min before and 15, 30, 60 and 120 min after 8-OH-DPAT administration (1 mg/kg i.p.). Values are shown as mean of changes in body temperature±SEM from 5 mice per group.

The present inventors have observed that it is possible to specifically target a nucleic acid to a cell of interest which expresses a neurotransmitter transporter by covalently coupling said nucleic acid to a molecule which is capable of specifically binding to said neurotransmitter transporter and, more in particular, to an inhibitor of said transporter. In particular, the authors have shown that a nucleic acid targeting particular regions of alpha-synuclein mRNA coupled to a selectivity agent to a DAT, SERT or NET neurotransmitter transporter is capable of decreasing alpha-synuclein mRNA expression levels.

A. Conjugates of the Invention

In a first aspect, the invention relates to a conjugate comprising:
 i) at least one selectivity agent which binds specifically to one or more neurotransmitter transporters selected from the group consisting of a dopamine transporter (DAT), serotonin transporter (SERT) or a norepinephrine transporter (NET) and
 ii) at least one nucleic acid which is capable of specifically binding to a target molecule which is expressed in the same cell as the neurotransmitter transporter wherein said target molecule is α-synuclein or the mRNA encoding α-synuclein.

The term "conjugate", as used herein, refers to any compound resulting from the covalent attachment of two or more individual compounds. In the present invention, conjugate refers to a molecule comprising a selectivity agent and a nucleic acid which are covalently coupled, being said coupling direct or via a linking compound.

The terms "covalent coupling" or "covalent attachment" mean that the nucleic acid and the selectivity agent are directly covalently joined to one another, or indirectly covalently joined to one another through an intervening moiety or moieties, such as a linker, or a bridge, or a spacer, moiety or moieties.

A.1. The Selectivity Agent of the Conjugates of the Invention

The expression "selectivity agent which binds specifically to one or more of a neurotransmitter transporter", as used herein, refers to any substance which binds to a neurotransmitter transporter. This binding specificity allows the delivery of a molecule which is attached to said selectivity agent to the cell, tissue or organ which contains said neurotransmitter transporter. In this way, a conjugate carrying said selectivity agent will be directed specifically to said cells when administered to an animal or contacted in vitro with a population of cells of different types.

As used herein, specific binding of a first molecule to a second molecule refers to the ability of the first molecule to bind said second molecule in a way that is measurably different from a non-specific interaction. A selectivity agent according to the present invention may show a Kd for the target (the neurotransmitter transporter) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M or greater.

The term "neurotransmitter transporter", as used herein, refers to a protein belonging to a class of membrane transport proteins that span the cellular membranes of neurons and which primary function is to carry neurotransmitters across these membranes and to direct their further transport to specific intracellular locations. Neurotransmitter transporters which may be targeted by the selectivity agents of the invention include, without limitation, uptake carriers present in the plasma membrane of neurons and glial cells, which pump neurotransmitters from the extracellular space into the cell. This process relies on the Na+ gradient across the plasma membrane, particularly the co-transport of Na+. Two families of proteins have been identified. One family includes the transporters for GABA, monoamines such as noradrenaline, dopamine, serotonin, and amino acids such as glycine and proline. Common structural components include twelve putative transmembrane α-helical domains, cytoplasmic N- and C-termini, and a large glycosylated extracellular loop separating transmembrane domains three and four. This family of homologous proteins derives their energy from the co-transport of $Na^+$ and $Cl^-$ ions with the neurotransmitter into the cell ($Na^+/Cl^-$ neurotransmitter transporters). The second family includes transporters for excitatory amino acids such as glutamate. Common structural components include putative 6-10 transmembrane domains, cytoplasmic N- and C-termini, and glycosylations in the extracellular loops. The excitatory amino acid transporters are not dependent on Cl−, and may require intracellular K+ ions (Na+/K+-neurotransmitter transporters) (Liu, Y. et al. (1999) Trends Cell Biol. 9: 356-363).

Neurotransmitter transporters which may be targeted by the selectivity agents of the invention also include neurotransmitter transporters present in intracellular vesicle membranes, typically synaptic vesicles, which primary function is concentrating neurotransmitters from the cytoplasm into the vesicle, before exocytosis of the vesicular contents during synaptic transmission. Vesicular transport uses the electrochemical gradient across the vesicular membrane generated by a H+-ATPase. Two families of proteins are involved in the transport of neurotransmitters into vesicles. One family uses primarily proton exchange to drive transport into secretory vesicles and includes the transporters for monoamines and acetylcholine. For example, the monoamine transporters exchange two luminal protons for each molecule of cytoplasmic transmitter. The second family includes the GABA transporters, which relies on the positive charge inside synaptic vesicles. The two classes of vesicular transporters show no sequence similarity to each other and have structures distinct from those of the plasma membrane carriers (Schloss, P. et al. (1994) Curr. Opin. Cell Biol. 6: 595-599; Liu, Y. et al. (1999) Trends Cell Biol. 9: 356-363).

In a preferred embodiment, the selectivity agent is not a peptide.

Specific types of neurotransmitter transporters that can be targeted with the selectivity agents of the invention include dopamine transporters (DAT), serotonin transporters (SERT) and norepinephrine transporters (NET).

The term "dopamine transporter" or "DAT" or "SLC6A3" refers to a molecule which is an integral membrane protein that transports the neurotransmitter dopamine from the synaptic cleft and deposits it into surrounding cells, thus terminating the signal of the neurotransmitter. Human SLC6A3 (solute carrier family 6, neurotransmitter transporter, dopamine, member 3) gene is deposited in NCBI GenBank (version dated Oct. 7, 2012) with accession number NG 015885.1, and human SLC6A3 mRNA is deposited with accession number NM_001044.4. Human dopamine transporter protein is deposited in GenBank with accession number NP_001035.1.

The term "serotonin transporter" or "SERT" or "SLC6A4", as used herein, refers to a polypeptide which is an integral membrane protein that transports the neurotransmitter serotonin from synaptic spaces into presynaptic neurons. Human SLC6A4 (solute carrier family 4, neurotransmitter transporter, serotonin, member 4) gene is deposited in NCBI GenBank (version dated Oct. 21, 2012) with accession number NG_011747.1, and human SLC6A4 mRNA is deposited with accession number NM_001045.4. Human serotonin transporter protein is deposited in GenBank with accession number NP_001036.1. The sequences of the human, rat, mouse and bovine SERT are provided in the SwissProt database under accession numbers P31645, P31652, Q60857 and Q9XT49 respectively. Similarly as with the nucleic acids targeting 5-HT$_{1A}$R cDNA, any region in the SERT cDNA can be targeted as long as it results in a substantial inhibition in the levels of the corresponding mRNA or the protein encoded by said mRNA. Thus, suitable SERT-specific nucleic acids can be identified as described above by measuring the levels of the SERT mRNA or SERT protein in cells expressing SERT after said cells have been contacted with the nucleic acid to be tested.

The term "norepinephrine transporter" or "NET" or "SLC6A2" refers to a molecule which is a transmembrane protein that transports synaptically released norepinephrine back into the presynaptic neuron. Human SLC6A2 (solute carrier family 6, neurotransmitter transporter, noradrenaline, member 2) gene is deposited in NCBI GenBank (version dated Oct. 21, 2012) with accession number NG_016969.1. Four transcripts are deposited in GenBank for the human norepinephrine transporter. mRNA transcript variant 1 (mRNA1) is the transcript variant of human norepinephrine transporter that encodes the longer isoform or isoform 1. This mRNA1 is deposited in GenBank with accession number NM_001172504.1. mRNA transcript variant 2 (mRNA2), is a transcript variant that has an alternate 3' exon including the coding region, as compared to variant 1. This mRNA2 is deposited in GenBank with accession number NM_001172501.1. mRNA transcript variant 3 (mRNA3), is a transcript variant that has an alternate 3' exon including the coding region, as compared to variant 1. This mRNA3 is deposited in GenBank with accession number NM_001043.3. mRNA transcript variant 4 (mRNA4), is a transcript variant that has alternate 5' and 3' sequences including the 5' and 3' coding regions, as compared to variant 1. This mRNA4 is deposited in GenBank with accession number NM_001172502.1. Four human protein isoforms are deposited in GenBank, with accession numbers NP_001165975.1, NP_001165972.1, NP_001034.1 and NP_001165973.1.

In a particular embodiment the selectivity agent is selected from the group consisting of a triple reuptake inhibitor, a noraderenaline dopamine double reuptake inhibitor, a serotonin single reuptake inhibitor, a noradrenaline single reuptake inhibitor and a dopamine single reuptake inhibitor.

The term "triple reuptake inhibitor" or "TRI", also known as a serotonin, norepinephrine and dopamine reuptake inhibitor (SNDRI), refers to a molecule that simultaneously acts as a reuptake inhibitor for the monoamine neurotransmitters, serotonin (5-HT), norepinephrine (noradrenaline, NA) and dopamine (DA), by blocking the action of the serotonin transporter (SERT), norepinephrine transporter (NET), and dopamine transporter (DAT), respectively. This, in turn, leads to increased extracellular concentrations of these neurotransmitters and, therefore, an increase in serotonergic, noradrenergic or adrenergic, and dopaminergic neurotransmission. In a particular embodiment, the triple reuptake inhibitor of the invention is a dopamine, serotonine, norepinephrine triple reuptake inhibitor.

The term "double reuptake inhibitor" refers to a molecule capable of inhibiting reuptake for two neurotransmitter transporters simultaneously. In a particular embodiment, the double reuptake inhibitor of the invention is a norepinephrine dopamine double reuptake inhibitor.

The term "single reuptake inhibitor" refers to a molecule capable of inhibiting reuptake in a particular neurotransmitter transporter. In a particular embodiment of the invention, the single reuptake inhibitor is a dopamine single reuptake inhibitor.

The term "dopamine reuptake inhibitor" or "DRI" acts as a reuptake inhibitor for the neurotransmitter dopamine by blocking the action of the dopamine transporter (DAT). This in turn leads to increased extracellular concentrations of dopamine and therefore an increase in dopaminergic neurotransmission. Suitable DRIs include, without limitation, pharmaceutical drugs such as amineptine, Benzatropine/Benztropine, Bupropion, dexmethylphenidate, Esketamine, Etybenzatropine/Ethybe, Ponalide, Fencamfamine, Fencamine, Ketamine, Lefetamine, Medifoxamine, Mesocarb, Methylphenidate, Nefopam, Nomifensine, Pipradrol, Prolintane, Pyrovalerone, Tiletamine and Tripelennamine; research chemicals such as altropane, amfonelic acid, benocyclidine, brasofensine, bromantane, DBL-583, dichloropane, diclofensine, Dieticyclidine, difluoropine, gacyclidine, GBR-12,935, indatraline, ioflupane, Iometopane, manifaxine, radafaxine, tametraline, tesofensine, troparil and vanoxerine. Suitable DRIs can be identified using assays known to the skilled artisan such as the determination of the capacity of the putative DRI in inhibiting high-affinity uptake of the dopamine by synaptosomal preparations prepared from rat corpus striatum carried out as described using methods published by Kula et al., (Life Sciences 34: 2567-2575, 1984).

The term "norepinephrine-dopamine reuptake inhibitor" or "NDRI", as used herein, refers to a compound which acts as a reuptake inhibitor for the neurotransmitters norepinephrine and dopamine by blocking the action of the norepinephrine transporter (NET) and the dopamine transporter (DAT), respectively. This in turn leads to increased extracellular concentrations of both norepinephrine and dopamine and therefore an increase in adrenergic and dopaminergic neurotransmission. Suitable NDRIs for use in the conjugates of the present invention include, without limitation, Amineptine (Survector, Maneon, Directin), Bupropion (Wellbutrin, Zyban), Dexmethylphenidate (Focalin), Fencamfamine (Glucoenergan, Reactivan), Fencamine (Altimina, Sicoclor), Lefetamine (Santenol), Methylphenidate (Ritalin, Concerta), Nomifensine (Merital), Pipradrol (Meretran), Prolintane (Promotil, Katovit), Pyrovalerone (Centroton, Thymergix), Nefopam (Acupan), adhyperforin (found in *Hypericum perforatum* (St. John's Wort)), hyperforin (found in *Hypericum perforatum* (St. John's Wort)), Cocaine, Desoxypipradrol (2-DPMP), Diphenylprolinol (D2PM), Methylenedioxypyrovalerone (MDPV), Cilobamine, Manifaxine (GW-320,659), Radafaxine (GW-353,162), Tametraline (CP-24,441).

The term "serotonin reuptake inhibitor" or "SRI, refers to a molecule which is capable of blocking serotonin uptake and includes both selective serotonin reuptake inhibitors (SSRI) (which block specifically serotonin uptake without substantially affecting other neurotransmitter) as well as non-selective serotonin reuptake inhibitors such as serotonin-norepinephrine reuptake inhibitors (SNRI) and serotonin-norepinephrine-dopamine reuptake inhibitors (SNDRI).

The term "serotonin selective reuptake inhibitors" or "SSRI" refers to selective inhibitors of serotinine reuptake without substantially affecting other neurotransmitter reuptake or transporter systems. These compounds act primarily at the presynaptic serotoninergic cell leading to an increase in the extracellular level of the neurotransmitter serotonin, thereby increasing the level of serotonin available to bind to the postsynaptic receptor and reversing the deficit of the activity of this monoaminergic neurotransmitter system in the brain. Illustrative non-limitative examples of SSRI include sertraline (CAS 79617-96-2), a sertraline-structural analog, fluoxetine (CAS 54910-89-3), fluvoxamine (CAS 54739-18-3), paroxetine (CAS 61869-08-7), indapline (CAS 63758-79-2), zimeldine (CAS 56775-88-3), citalopram (CAS 59729-33-8) and escitalopram (CAS 219861-08-2). Assays for determining whether a given compound is acting as a SSRI are, for instance, the ability to reduce ex vivo uptake of serotonin and of antagonizing the serotonin-depleting action of p-chloroamphetamine without affecting rat heart uptake of intravenous [$^3$H]norepinephrine as described essentially in Koe et al. (J. Pharmacol. Exp. Ther., 1983, 226:686-700).

The term "serotonin-norepinephrine reuptake inhibitor" or "SNRI" refers to a family of compounds which are capable of inhibiting the reuptake of serotonin by blocking the serotonin transporter and the reuptake of norepinephrine by blocking the norepinephrine transporter. This family includes compounds such as venlafaxine (CAS 93413-69-5), desvenlafaxine (CAS 93413-62-8), duloxetine (CAS 116539-59-4), milnacipran (CAS 92623-85-3), Sibutramine (106650-56-0), Tramadol (CAS 27203-92-5) and Bicifadine (CAS 71195-57-8). Assays for determining whether a given compound is acting as a SNRI are, for instance, the ability to reduce the uptake of serotonin and norepinephrine by brain synaptosomes as described essentially in Bolden-Watson C, Richelson E. (Life Sci. 1993; 52(12):1023-9). A particular type of SNRIs are tricyclic antidepressants which are SNRIs having a general molecular structure comprising three rings. Prominent among the tricyclic anti-depressants are the linear tricyclics, e.g., imipramine, desipramine, amitriptyline, nortriptyline, protriptyline, doxepin, ketipramine, mianserin, dothiepin, amoxapine, dibenzepin, melitracen, maprotiline, flupentixol, azaphen, tianeptine and related compounds showing similar activity. Angular tricyclics include indriline, clodazone, nomifensin, and related compounds. A variety of other structurally diverse anti-depressants, e.g., iprindole, wellbatrin, nialamide, milnacipran, phenelzine and tranylcypromine have been shown to produce similar activities. They are functionally equivalent to the tricyclic anti-depressants and are therefore included within the scope of the invention. Thus, the term tricyclic anti-depressant is intended by the present inventor to embrace the broad class of anti-depressants described above together with related compounds sharing the common property that they all possess anti-depressant activity and which include, without limitation, compounds such as amitriptyline, amitriptylinoxide, carbamazepine, butriptyline, clomipramine, demexiptiline, desipramine, dibenzepin, dimetacrine, dosulepin/dothiepin, Doxepin, Imipramine, Imipraminoxide, Iprindole, Lofepramine, Melitracen, Metapramine, Nitroxazepine, Nortriptyline, Noxiptiline, pregabalin, Propizepine, Protriptyline, Quinupramine and Trimipramine.

The term "noradrenaline reuptake inhibitor", "NRI", "NERI", adrenergic reuptake inhibitor" or "ARI" refers to a family of compounds which are capable of blocking reuptake of noradrenaline and adrenaline by blocking the action of the norepinephrine transporter (NET). This family of compounds includes the selective NRIs which block exclusively the NET without affecting other monoamine transporters as well as non-selective NRIs such as the SNRIs, which block the norepinephrine transporter and the serotinine transporter (see above), the norepinephrine-dopamine reuptake inhibitors (NDRI), which block the norepinephrine and the dopamine transporters (see below), tricyclic antidepressants and tetracyclic antidepressants (see above). Suitable selective NRIs adequate for the present invention include, without limitation, Atomoxetine/Tomoxetine (Strattera or CAS 83015-26-3), Mazindol (Mazanor, Sanorex or CAS 22232-71-9), Reboxetine (Edronax, Vestra or CAS 98819-76-2) and Viloxazine (Vivalan or CAS 46817-91-8).

In a particular embodiment, the conjugate of the invention comprises a selectivity agent which is a triple reuptake inhibitor. In a preferred embodiment of the invention, the selectivity agent is a triple reuptake inhibitor having the following structure (I):

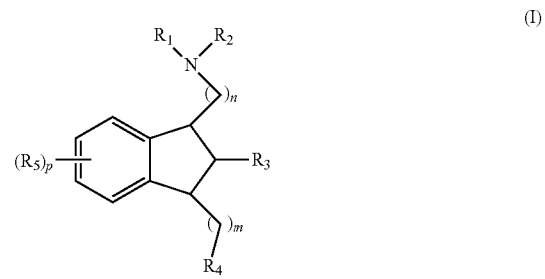

wherein n or m are integers each having a value between 0 and 6, inclusive;

p is an integer having a value between 0 and 4, inclusive $R_1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_A$; —CO$_2$$R_A$; —C(=O)N($R_A$)$_2$ or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_B$; —CO$_2$$R_B$; —C(=O)N($R_B$)$_2$ or —C($R_B$)$_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_C$; —C(=O)$R_C$;

—CO$_2$R$_C$; —CN; —SCN; —SR$_C$; —SOR$_C$; SO$_2$R$_C$; —NO$_2$; —N$_3$; —N(R$_C$)$_2$; —NHC(=O)R$_C$; —NR$_C$C(=O)N(R$_C$)$_2$; —OC(=O)OR$_C$; —OC(=O)R$_C$; —OC(=O)N(R$_C$)$_2$; —NR$_C$C(=O)OR$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_4$ is substituted or unsubstituted, branched or unbranched aryl; or substituted or unsubstituted, branched or unbranched heteroaryl;

R$_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_E$; —C(=O)R$_E$; —CO$_2$R$_E$; —CN; —SCN; —SR$_E$; —SOR$_E$; SO$_2$R$_E$; —NO$_2$; —N$_3$; —N(R$_E$)$_2$; —NHC(=O)R$_E$; —NR$_E$C(=O)N(R$_E$)$_2$; —OC(=O)OR$_E$; —OC(=O)R$_E$; —OC(=O)N(R$_E$)$_2$; —NR$_E$C(=O)OR$_E$; or —C(R$_E$)$_3$ wherein each occurrence of R$_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable forms thereof.

In a more preferred embodiment of the invention, the selectivity agent of the conjugate of the invention is a triple reuptake inhibitor having the following structure (II):

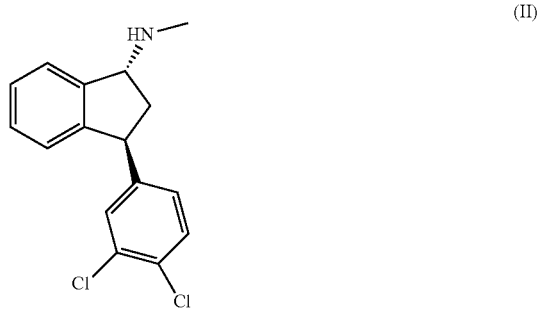 [SMILES: CN[C@@H]1C[C@@H](c2ccc(Cl)c(Cl)c2)c2ccccc21]

(II)

wherein the selectivity agent having the structure (II) is also known as (1R,3S)-3-(3,4-dichlorophenyl)-N-methyl-2,3-dihydro-1H-inden-1-amine or indatraline.

A.2. The Nucleic Acid of the Conjugates of the Invention

The second component of the conjugate according to the present invention is a nucleic acid which is capable of specifically binding to a target molecule which is expressed in the same cell as the neurotransmitter transporter, wherein said target molecule is α-synuclein or the mRNA encoding α-synuclein.

The term "alpha-synuclein", as used herein, refers to a polypeptide of the synuclein member family (α-synuclein, β-synuclein and γ-synuclein) which contains a highly conserved alpha-helical lipid-binding motif with similarity to the class-A2 lipid-binding domains of the exchangeable apolipoproteins and which are capable of forming intracellular aggregates known as Lewy bodies which appear in certain neural diseases such as Parkinson's disease, Alzheimer's disease and Lewy body disease.

The sequences of the human, rat, mouse and bovine α-synuclein are provided in the SwissProt database under accession numbers P37840, P37377, 055042 and Q3T0G8, respectively. Similarly as with the nucleic acids targeting 5-HT$_{1A}$R cDNA, the α-synuclein-specific nucleic acids can be identified or selected using any method as described above and tested for their capacity to induce a substantial inhibition in the levels of the corresponding mRNA or the protein encoded by said mRNA. Thus, suitable α-synuclein-specific nucleic acids can be identified as described above by measuring the levels of the α-synuclein mRNA or α-synuclein protein in cells expressing α-synuclein after said cells have been contacted with the nucleic acid to be tested.

Typically, the nucleic acid of the invention is capable of inhibiting the function of the target molecule, i.e. of inhibiting α-synuclein. Thus, if the target molecule is the α-synuclein mRNA, then the nucleic acid acts by inhibiting the translation of the α-synuclein mRNA leading to a decrease in the levels of the α-synuclein protein encoded by the mRNA. If the target molecule is the α-synuclein protein, then the nucleic acid (typically an aptamer) acts by inhibiting the activity of the protein.

The term "nucleic acid", as used herein, refers to a polymer having two or more deoxyribonucleotide, ribonucleotide or nucleotide analog molecules as well as molecules that are structurally similar to a native nucleic acid, but differ from the native nucleic acid (e.g., through chemical modification) at one or more of the nucleic acid backbone (e.g., phosphate in native nucleic acids), nucleic acid sugar (e.g., deoxyribose for native DNA and ribose in native RNA), and nucleic acid base (e.g., adenosine, cytosine, guanine or thymidine in native nucleic acids).

The oligonucleotide can be a double stranded or single stranded oligonucleotide including, without limitation, small interference RNAs (siRNA), small hairpin RNAs (shRNA), microRNAs (miRNA), antisense oligonucleotides or ribozymes. If double stranded nucleic acids are used, these comprise a first sense strand which is complementary to the target nucleic acid and a second antisense strand which is complementary to the sense, which allows the formation of the double stranded DNA by base pairing between the first and second strand.

The term "antisense strand" refers to the strand of a double stranded nucleic acid which includes a region that is substantially complementary to a target sequence. Where the region of complementarity is not fully complementary to the target sequence, the mismatches are most tolerated outside nucleotides 2-7 of the 5' terminus of the antisense strand. The term "sense strand," as used herein, refers to the strand of a dsRNA that includes a region that is substantially complementary to a region of the antisense strand.

In a particular embodiment of the invention, the nucleic acid sequence which is capable of specifically binding to a target molecule which is expressed in the same cell as the neurotransmitter transporter is selected from the group consisting of a gapmer, double stranded interference RNA, double stranded RNA with microRNA activity, an antisense oligonucleotide, an antiMicro RNA, preMiRNA, a mRNA coding for microRNAs or shRNAs, a PNA, a LNA, a ribozyme and an aptamer.

An "antisense oligonucleotide" as used herein includes antisense or sense oligonucleotides comprising a single-stranded nucleic acid sequence (either RNA or DNA) capable of binding to target mRNA (sense) or DNA (antisense) sequences. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

As used herein, the term "ribozyme" or "RNA enzyme" or "catalytic RNA" refers to an RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome, the ligase activity of a DNA ligase, and a number of other chemical reactions performed by conventional protein enzymes.

An "aptamer" as used herein refers to a nucleic acid ligand that binds to more than one site on a target molecule where binding is not "complementary," i.e., is not due to base-pair formation between a nucleic acid ligand and a target nucleic acid sequence. An aptamer can be designed which binds to any envisionable target, including polypeptides. Aptamers offer the utility for biotechnological and therapeutic applications as they offer molecular recognition properties that rival that of the commonly used biomolecule, antibodies. In addition to their selective recognition, aptamers offer advantages over antibodies as they can be engineered completely in a test tube, are readily produced by chemical synthesis, possess desirable storage properties, and elicit little or no immunogenicity in therapeutic applications. Aptamers can be synthesized through repeated rounds of in vitro partition, selection and amplification, a methodology known in the state of the art as "SELEX", (Systematic Evolution of Ligands by Exponential Enrichment) (Shamah et al, Acc. Chem. Res. 2008, 41 pp. 130-8). Alternatively, they can be synthesized, for example, by step-wise solid phase synthesis.

The nucleic acid of the invention may contain one or more modifications in the nucleobases, in the sugars and/or in the internucleotide linkages.

Modifications to one or more backbone residues of the nucleic acids may comprise one or more of the following: 2' sugar modifications such as 2'-O-methyl (2'-OMe), 2'-O-methoxyethyl (2'-MOE), 2'-O-methoxyethoxy, 2'-Fluoro (2'-F), 2'-Allyl, 2'-O-[2-(methylamino)-2-oxoethyl], 2'-O—(N-methylcarbamate); 4' sugar modifications including 4'-thio, 4'O—$CH_2$—O-2'-bridge, 4-$(CH_2)_2$—O-2'-bridge; Locked Nucleic Acid (LNA); Peptide Nucleic Acid (PNA); Intercalating nucleic acid (INA); Twisted intercalating nucleic acid (TINA); Hexitol nucleic acids (HNA); arabinonucleic acid (ANA); cyclohexane nucleic acids (CNA); cyclohexenyl-nucleic acid (CeNA); threosyl nucleic acid (TNA); Morpholino oligonucleotides; Gap-mers; Mix-mers; Incorporation Arginine-rich peptides; addition of 5'-phosphate to synthetic RNAs; RNA Aptamers (Que-Gewirth N S, Gene Ther. 2007 February; 14(4):283-91.); RNA Aptamers regulated with antidotes on the subject of the specific RNA aptamer (ref. Oney S, Oligonucleotides. 2007 Fall; 17(3): 265-74.) or any combinations thereof.

Modifications to one or more internucleoside linkages of the nucleic acids may comprise one or more of the following: Phosphorothioate, phosphoramidate, phosphorodiamidate, phosphorodithioate, phosphoroselenoate, phosphorodiselenoate, phosphoroanilothioate and phosphoranilidate, or any combinations thereof.

A Locked Nucleic Acid (LNA), often referred to as inaccessible RNA, is a modified RNA nucleotide. The ribose moiety of an LNA nucleotide is modified with an extra bridge connecting the 2' and 4' carbons (O2',C4'-methylene bridge). The bridge "locks" the ribose in the 3'-endo structural conformation, which is often found in the A-form of DNA or RNA. LNA nucleotides can be mixed with DNA or RNA bases in the nucleic acid whenever desired. Such oligomers are commercially available. The locked ribose conformation enhances base stacking and backbone pre-organization. This significantly increases the thermal stability (melting temperature) and hybridization affinity of LNA-modified nucleic acids, besides having improved mismatch discrimination abilities. These properties make them very useful for antisense-based techniques. Further, LNA anti-miR oligonucleotides have been tested in primates with encouraging results and low toxicity.

Peptide Nucleic Acid (PNA) is an artificially synthesized polymer similar to DNA or RNA and is used in biological research and medical treatments. PNA is not known to occur naturally. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right. Since the backbone of PNA contains no charged phosphate groups, the binding between PNA/DNA strands is stronger than between DNA/DNA strands due to the lack of electrostatic repulsion. Mixed base PNA molecules are true mimics of DNA molecules in terms of base-pair recognition. PNA/PNA binding is stronger than PNA/DNA binding.

Morpholinos are synthetic molecules which are the product of a redesign of the natural nucleic acid structure. Structurally, the difference between morpholinos and DNA or RNA is that while Morpholinos have standard nucleobases, those bases are bound to 6-membered morpholine rings instead of deoxyribose/ribose rings and non-ionic phosphorodiamidate intersubunit linkages replace anionic phosphodiester linkages. Morpholinos are sometimes referred to as PMO (phosphorodiamidate morpholino oligonucleotide). The 6-membered morpholine ring has the chemical formula O—$(CH_2$—$CH_2)_2$—NH.

Gapmers or "gapped oligomeric compounds" are RNA-DNA-RNA chimeric oligonucleotide probes, where windows or 'gaps' of DNA are inserted into an otherwise normal or modified RNA oligonucleotide known as "wings". This modification increases oligonucleotide stability in vivo and the avidity of the interaction of the probe with the target, so that shorter probes can be used effectively. Preferrably, the wings are 2'-O-methyl (OMe) or 2'-O-methoxyethyl (MOE) modified ribonucleotides that protect the internal block from nuclease degradation. Moreover, the nucleotides forming the gap or the wings may be connected by phosphodiester bonds or by phosphorothioate bonds, thus making it resistant to RNase degradation. Additionally, the nucleotides forming the wings may also be modified by incorporating bases connected by 3' methylphosphonate linkages.

The expression "RNA interference" or RNAi is a process of sequence-specific post-transcriptional gene repression which can occur in eukaryotic cells. In general, this process involves degradation of an mRNA of a particular sequence induced by double-stranded RNA (dsRNA) that is homologous to that sequence. This dsRNA is capable of causing the silencing of gene expression by means of converting said RNA into siRNA by means of an RNase type III (Dicer). One of the siRNA strands is incorporated into the ribonucleoprotein complex referred to as the RNA-induced silencing complex (RISC). The RISC complex uses this single strand of RNA to identify mRNA molecules that are at least partially complementary to the RNA strand of the siRNA incorporated in the RISC that are degraded or undergo an inhibition in their translation. Thus, the siRNA strand that is incorporated into the RISC is known as a guide strand or antisense strand. The other strand, which is known as a transient strand or sense strand, is eliminated from the siRNA and is partly homologous to the target mRNA. The degradation of a target mRNA by means of the RISC complex results in a reduction in the expression levels of said mRNA and of the corresponding protein encoded thereby. Furthermore, RISC can also cause the reduction in the expression by means of the inhibition of the translation of the target mRNA.

The nucleic acid of the conjugates of the invention are capable of specifically binding to the target molecule α-synuclein which is expressed in the same cell as the neurotransmitter transporter selected from the group consisting of DAT, SERT and NET. The binding of the nucleic acid to the target molecule can occur via Watson-Crick interactions wherein the target molecule is a nucleic acid which contains a sequence which is complementary to the sequence of the nucleic acid. Alternatively, when the target molecule is a polypeptide, the nucleic acid of the conjugates of the invention can also interact with said molecule, in which case the nucleic acid is acting as an aptamer.

The nucleic acid comprised by the conjugate according to the present invention specifically binds to alpha-synuclein in particular target region of alpha-synuclein mRNA. Thus, when the nucleic acid comprised by the conjugate of the invention binds to alpha-synuclein mRNA, said nucleic acid is targeted to a region of alpha-synuclein mRNA selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7).

The terms "silence" and "inhibit the expression of," "down-regulate the expression of," "suppress the expression of," and the like, in as far as they refer to a target gene, herein refer to the at least partial suppression of the expression of a target gene, as manifested by a reduction of the amount of target mRNA, which may be isolated from a first cell or group of cells in which a target gene is transcribed and which has or have been treated such that the expression of a target gene is inhibited, as compared to a second cell or group of cells substantially identical to the first cell or group of cells but which has or have not been so treated (control cells). The degree of inhibition is usually expressed in terms of:

[(mRNA in control cells)−(mRNA in treated cells)
*100 percent]/(mRNA in control cells)

Alternatively, the degree of inhibition may be given in terms of a reduction of a parameter that is functionally linked to target gene expression, e.g., the amount of protein encoded by a target gene or the number of cells displaying a certain phenotype. In principle, target genome silencing may be determined in any cell expressing the target, either constitutively or by genomic engineering, and by any appropriate assay. However, when a reference is needed in order to determine whether a given nucleic acid inhibits the expression of a target gene by a certain degree and therefore is encompassed by the instant invention, the assay provided in the Examples below and those known in the art shall serve as such reference. For example, in certain instances, expression of a target gene is suppressed by at least about 5 percent, 10 percent, 15 percent, 20 percent, 25 percent, 30 percent, 35 percent, 40 percent, 45 percent, or 50 percent by administration of the double-stranded oligonucleotide. In some embodiments, a target gene is suppressed by at least about 60 percent, 70 percent, or 80 percent by administration of the double-stranded oligonucleotide. In some embodiments, the target gene is suppressed by at least about 85 percent, 90 percent, or 95 percent by administration of the double-stranded oligonucleotide.

For instance, the nucleic acid sequence according to the present invention can be introduced into a cell that expresses the target gene alpha-synuclein. The mRNA level of the target gene in the cell can be detected by using RT-PCR, Northern blot or any other standard methods. Alternatively, the level of the polypeptide encoded by the target mRNA can be measured using Western blot, ELISA or any other immunological or non-immunological method. A substantial change in the expression level of mRNA or of the protein encoded by the target gene after the introduction of the siRNA sequence is indicative of the effectiveness of the siRNA sequence in suppressing the expression of the target gene. In one specific example, the expression levels of other genes are also monitored before and after the introduction of the siRNA sequence. An siRNA sequence which has inhibitory effect on target gene expression but does not significantly affect the expression of other genes can be selected. In another specific example, multiple siRNA or other RNAi sequences can be introduced into the same target cell. These siRNA or RNAi sequences specifically inhibit target gene expression but not the expression of other genes. In yet another specific example, siRNA or other RNAi sequences that inhibit the expression of the target gene and other gene or genes can be used.

According to the invention, the nucleic acid which is capable of specifically binding to alpha-synuclein mRNA is targeted to a particular region in the alpha-synuclein mRNA selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synuclein sequence as defined in NCBI accession number NM_000345 (SEQ ID NO:7).

In a particular embodiment of the conjugate of the invention, the nucleic acid is capable of specifically binding to the mRNA encoding α-synuclein in a region selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7) is an antisense oligonucleotide or a gapmer.

The antisense oligonucleotide according to the invention inhibits transcription and/or translation of a nucleic acid which encodes alpha-synuclein, the activity of which is to be inhibited. The antisense nucleic acids can be bound to the potential target of the drug by means of conventional base complementarity or, for example, in the case of binding to double stranded DNA through specific interaction in the large groove of the double helix. Generally, these methods refer to a range of techniques generally used in the art and they include any method which is based on the specific binding to oligonucleotide sequences.

An antisense construct of the present invention can be distributed, for example, as an expression plasmid which, when it is transcribed in a cell, produces RNA complementary to at least one unique part of the cellular mRNA encoding alpha-synuclein. Alternatively, the antisense construct is a oligonucleotide probe generated ex vivo which, when introduced into the cell, produces inhibition of gene expression hybridizing with the mRNA and/or gene sequences of a target nucleic acid. Such oligonucleotide probes are preferably modified oligonucleotides which are resistant to endogenous nucleases, for example, exonucleases and/or endonucleases and are therefore stable in vivo. Examples of nucleic acids molecules for use thereof as antisense oligonucleotides are DNA analogs of phosphoramidate, phosphothionate and methylphosphonate (see also U.S. Pat. Nos. 5,176,996; 5,264,564; and 5,256,775). Additionally, the general approximations for constructing oligomers useful in the antisense therapy have been reviewed, for example, in Van der Krol et al., BioTechniques 6: 958-976, 1988; and Stein et al., Cancer Res 48: 2659-2668, 1988.

Preferably, in vitro studies are performed first to quantify the capacity of the antisense oligonucleotides for inhibiting gene expression. Preferably these studies use controls which distinguish between antisense gene inhibition and non specific biological effects of the oligonucleotides. Also preferably these studies compare the levels of target RNA or protein with that of an internal control of RNA or protein. The results obtained using the antisense oligonucleotides can be compared with those obtained using a control oligonucleotide. Preferably the control oligonucleotide is approximately of the same length as the oligonucleotide to be assayed and the oligonucleotide sequence does not differ from the antisense sequence more than it is deemed necessary to prevent the specific hybridization to the target sequence.

The antisense oligonucleotide can be a single or double stranded DNA or RNA or chimeric mixtures or derivatives or modified versions thereof. The oligonucleotide can be modified in the base group, the sugar group or the phosphate backbone, for example, to improve the stability of the molecule, its hybridization capacity etc. The oligonucleotide may include other bound groups, such as peptides (for example, for directing them to the receptors of the host cells) or agents for facilitating transport through the cell membrane (see, for example, Letsinger et al., Proc. Natl. Acad. Sci. U.S.A. 86: 6553-6556, 1989; Lemaitre et al., Proc. Natl. Acad. Sci. 84: 648-652, 1987; PCT Publication No. WO 88/09810) or the blood-brain barrier (see, for example, PCT Publication No. WO 89/10134), intercalating agents (see, for example, Zon, Pharm. Res. 5: 539-549, 1988). For this purpose, the oligonucleotide can be conjugated to another molecule, for example, a peptide, a transporting agent, hybridization triggered cleaving agent, etc.

The antisense oligonucleotide may comprise at least one group of modified base. The antisense oligonucleotide may also comprise at least a modified sugar group selected from the group including but not limited to arabinose, 2-fluoroarabinose, xylulose, and hexose. The antisense oligonucleotide may also contain a backbone similar to a neutral peptide. Such molecules are known as peptide nucleic acid (PNA) oligomers and are described, for example, in Perry-O'Keefe et al., Proc. Natl. Acad. Sci. U.S.A. 93: 14670, 1996, and in Eglom et al., Nature 365: 566, 1993. In yet another embodiment, the antisense oligonucleotide comprises at least one modified phosphate backbone. In yet another embodiment, the antisense oligonucleotide is an alpha-anomeric oligonucleotide.

While antisense oligonucleotides complementary to the coding region of the target mRNA sequence can be used, those complementary to the transcribed non translated region can also be used.

In some cases, it may be difficult to reach the sufficient intracellular concentrations of the antisense to suppress the endogenous mRNA translation. Therefore, a preferred approximation uses a recombinant DNA construct in which the antisense oligonucleotide is placed under the control of a strong pol III or pol II promoter. Alternatively, the target gene expression can be reduced by directing deoxyribonucleotide sequences complementary to the gene regulating region (i.e., the promoter and/or enhancers) to form triple helix structures preventing gene transcription in the target cells in the body (see in general, Helene, Anticancer Drug Des. 6(6): 569-84, 1991). In certain embodiments, the antisense oligonucleotides are antisense morpholines.

Gapmers are RNA-DNA-RNA chimeric oligonucleotide probes, where windows or 'gaps' of DNA are inserted into an otherwise normal or modified RNA oligonucleotide known as "wings". Preferably, the wings are 2'-O-methyl (OMe) or 2'-O-methoxyethyl (MOE) modified ribonucleotides that protect the internal block from nuclease degradation. More preferably, the wings are 2'-O-methyl modified ribonucleotides. Moreover, the nucleotides forming the gap or the wings may be connected by phosphodiester bonds or by phosphorothioate bonds, thus making it resistant to RNase degradation. Additionally, the nucleotides forming the wings may also be modified by incorporating bases connected by 3' methylphosphonate linkages.

In a particular preferred embodiment of the conjugate according to the invention, the nucleic acid which is capable of specifically binding to the mRNA encoding α-synuclein in a region selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7), is a gapmer which comprises a central block of 10 deoxynucleotides flanked by blocks of 4 2'-O-methyl modified ribonucleotides.

In a more preferred embodiment, the gapmer consists of a sequence selected from the group consisting of SEQ ID NO:1, SEQ ID NO:2 and SEQ ID NO:3.

```
SEQ ID NO 1:  cuccAACATTTGTCacuu   (ID #1232)

SEQ ID NO 2:  cuccCTCCACTGTCuucu   (ID #1233)

SEQ ID NO 3:  cugcTCCCTCCACTgucu   (ID #1234)
```

In an alternative embodiment of the conjugate of the invention, the nucleic acid which is capable of specifically binding to the mRNA encoding α-synuclein in a region selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7). In particular, the interfering RNA is selected from the group comprising small interfering (siRNA), short hairpin RNA (shRNA) or micro RNA (miRNA).

The term small interfering RNA ("siRNA") refers to small inhibitory RNA duplexes that induce the RNA interference pathway. These molecules may vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands. As used herein, siRNA molecules are not limited to RNA molecules but further encompass nucleic acids with one or more chemically modified nucleotides, such as morpholinos.

A particular preferred siRNA according to the invention is targeted to region in the alpha-synuclein mRNA located at position 499-517 wherein the numbering corresponds to the position with respect to the first nucleotide in the alpha-synuclein sequence as defined in NCBI accession number NM_000345. This siRNA has the sequence:

```
siRNA 499-517 sense strand:
                              (SEQ ID NO: 8)
agaagacaguggagggagcTT siRNA 499-517 antisense strand:
                              (SEQ ID NO: 9)
gcucccuccacugucuucuTT
```

The term "shRNA" or "short hairpin RNA" as used herein refers to a dsRNA where the two strands are connected by an uninterrupted chain of nucleotides between the 3'-end of one strand and the 5' end of the respective other strand to form a duplex structure.

The term "micro RNA" or "miRNA" refers to short single-stranded RNA molecules, typically of about 21-23 nucleotides in length capable of regulating gene expression. miRNAs may be synthetic (i.e., recombinant) or natural. Natural miRNAs are encoded by genes that are transcribed from DNA and processed from primary transcripts ("pri-miRNA") to short stem-loop structures ("pre-miRNA"), and finally to mature miRNA. Mature miRNA molecules are partially complementary to one or more mRNA molecules, and downregulate gene expression via a process similar to RNA interference, or by inhibiting translation of mRNA.

In another embodiment, the nucleic acid of the conjugates of the invention is a miRNA which is capable of specifically silencing α-synuclein mRNA. Suitable α-synuclein-specific miRNAs include, without limitation, miR-7 (see Proc. Natl. Acad. Sci. USA, 2009, 106: 13052-13057) and miR-153 (see J Biol Chem 2010 285(17): 12726-12734. Human miRNA 7-1 sequence is located at NCBI with accession number NR_029605 (SEQ ID NO:10), human miRNA 7-2 with accession number NR_029606 (SEQ ID NO:11) and human miRNA 7-3 with accession number NR_029607 (SEQ ID NO:12). Human miRNA 153-1 is located at NCBI with accession number NR_029688 (SEQ ID NO:13) and miRNA 153-2 with accession number NR_029689 (SEQ ID NO:14).

```
A miR-7 according to the invention has the
sequence:
                              (SEQ ID NO: 15)
UGGAAGACUAGUGAUUUUGUUG.

A miR-153 according to the present invention has
the sequence:
                              (SEQ ID NO: 16)
UUGCAUAGUCACAAAAGUGAUC.
```

Methods for pairwise alignment of two given nucleic acid sequences are widely known to the skilled person and can be carried out by standard algorithms of the type BLASTN [BLAST Manual, Altschul, S., et al., NCBI NLM NIH Bethesda, Md. 20894, Altschul, S., et al., J. Mol. Biol. 215: 403-410 (1990)] using the default parameters. Methods for the alignment of multiple nucleic acid sequences can be carried out using standard algorithms of the type CLUSTALW (Thompson J D et al, Nucleic Acids Res, 1994, 22:4673-4680) using the default parameters.

When the interfering RNA of the conjugate of the invention is a double stranded interfering RNA, the conjugate according to the invention can comprise one selectivity agent or two selectivity agents. In a particular embodiment, the first selectivity agent and the second selectivity agent are the same selectivity agent. In an alternative embodiment, the first selectivity agent is different from the second selectivity agent. The second selectivity agent of the conjugate of the invention binds specifically to one or more neurotransmitter transporters selected from the group consisting of a dopamine transporter (DAT), serotonin transporter (SERT) or a norepinephrine transporter (NET), as previously described. When the conjugate according to the invention comprises a double stranded interfering RNA and one selectivity agent, the selectivity agent can be conjugated to the 5' end of the sense strand of the interfering RNA or to the 5' of the antisense strand of the interfering RNA. When the conjugate according to the invention comprises a double stranded interfering RNA and two selectivity agents, the first selectivity agent is conjugated to the 5' end of the sense strand of the interfering RNA and the second selectivity agent is conjugated to the 5' of the antisense strand of the interfering RNA.

In a particular embodiment, the conjugate according to the invention comprises an interfering RNA, a first selectivity agent and a second selectivity agent. In a more particular embodiment, the second selectivity agent of the conjugate is connected to the opposite end of the polynucleotide (interfering RNA) which is connected to the first selectivity agent. In a particular embodiment, the second selectivity agent of the conjugate is connected to one end of the polynucleotide which is complementary to the polynucleotide which is connected to the first selectivity agent. In a particular embodiment, the second selectivity agent of the conjugate is connected to the same end of the polynucleotide which is connected to the first selectivity agent by virtue of a polyfunctional linker attached to said end.

A.3. Linker Regions of the Conjugates of the Invention

The nucleic acid and the selectivity agent may be directly coupled. However, it is preferred that both moieties are linked by a connecting group.

The terms "connecting group", "linker", "linking group" and grammatical equivalents thereof are used herein to refer to an organic moiety that connects two parts of a compound. The selectivity agent can be attached to any sense or antisense nucleotide within the nucleic acid, but it can be preferably coupled through the 3' terminal nucleotide and/or 5' terminal nucleotide. An internal conjugate may be attached directly or indirectly through a linker to a nucleotide at a 2' position of the ribose group, or to another suitable position.

In the case wherein the nucleic acid is a double-stranded nucleic acid, the conjugate can be attached to the sense 3' terminal nucleotide, the sense 5' terminal nucleotide, the antisense 3' terminal nucleotide, and/or the antisense 5' terminal nucleotide.

Though not wishing to be limited by definitions or conventions, in this application the length of the linker is described by counting the number of atoms that represent the shortest distance between the atom that joins the selectivity agent to the linker and the oxygen atom of the terminal phosphate moiety associated with the oligonucleotide through which the linker is attached to the oligonucleotide.

In cases where the linker comprises one or more ring structures, counting the atoms around the ring that represent the shortest path is preferred.

Suitable linker groups for use in the present invention include, without limitation, modified or unmodified nucleotides, nucleosides, polymers, sugars, carbohydrates, polyalkylenes such as polyethylene glycols and polypropylene glycols, polyalcohols, polypropylenes, mixtures of ethylene and propylene glycols, polyalkylamines, polyamines such as polylysin and spermidine, polyesters such as poly(ethyl acrylate), polyphosphodiesters, aliphatics, and alkylenes. Moreover, linkers/linker chemistries that are based on omega-amino-1,3-diols, omega-amino-1,2-diols, hydroxyprolinols, omega-amino-alkanols, diethanolamines, omega-hydroxy-1,3-diols, omega-hydroxy-1,2-diols, omega-thio-1,3-diols, omega-thio-1,2-diols, omega-carboxy-1,3-diols, omega-carboxy-1,2-diols, co-hydroxy-alkanols, omega-thio-alkanols, omega-carboxy-alkanols, functionalized oligoethylene glycols, allyl amine, acrylic acid, allyl alcohol, propargyl amine, propargyl alcohol, and more, can be applied in this context to generate linkers of the appropriate length.

The linker may also confer other desirable properties on the oligonucleotide conjugate improved aqueous solubility, optimal distance of separation between the conjugate moiety and the oligonucleotide, flexibility (or lack thereof), specific orientation, branching, and others.

Preferably, said connecting group has the following structure

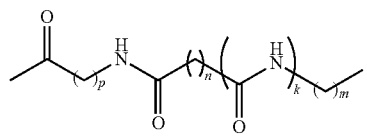

wherein
m, n and p are selected from 0, 1, 2, 3, 4, 5, 6, 7, 8, 9, 10, 11, 12 and 13,
wherein the sum of m+n+p is an integer number selected from 7, 8, 9, 10, 11, 12, 13, 14, 15, 16, 17 and 18 and
wherein k is 0 or 1.

In a preferred embodiment, p is 5, n is 2, k is 1 and m is 6 giving a linker having the structure:

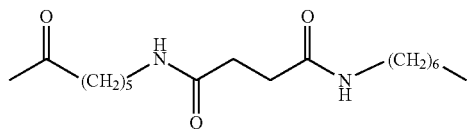

In another preferred embodiment, p is 5, n and k are 0 and m is 6 giving a linker having the structure:

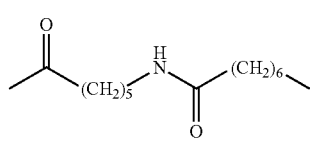

In a particular embodiment, the linker comprises more than one coupling for the selectivity agent. In a preferred embodiment, the linker is a bivalent or trivalent linker, i.e. 2 or 3 molecules of selectivity agent can be coupled, respectively.

In the case wherein more than one molecule of selectivity agent are coupled to the nucleic acid through a linker, said molecules can represent the same or different selectivity agents.

In a particular embodiment, the bivalent or trivalent linker has the following formula:

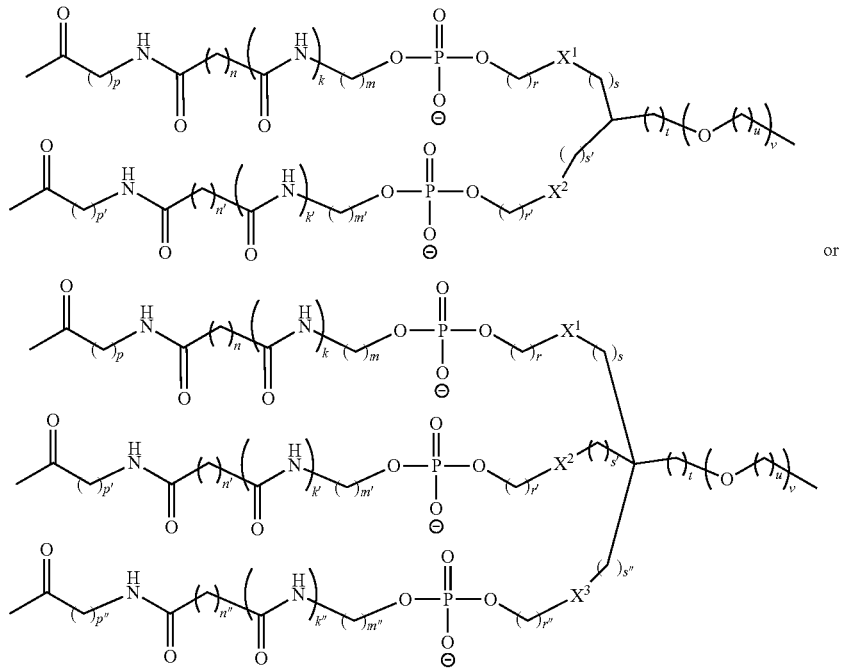

or wherein m, m', m", n, n', n", p, p', p", r, r', r", s, s', s", t and u are independently selected from 0, 1, 2, 3, 4, 5, 6, 7, 8, 9, 10, 11, 12 and 13;

k, k', k" and v are independently selected from 0 and 1; and

X$^1$, X$^2$ and X$^3$ are independently selected from CH$_2$, O, S, NH, CO, C(O)O and C(O)NH.

Depending on the values of the above mentioned groups, branched linkers can be symmetrical or asymmetrical.

In a particular embodiment, the linker is a bivalent linker as shown above wherein p and p' are 5, n and n' are 2, k and k' are 1 and m and m' are 6. In a particular embodiment, the linker is a bivalent linker wherein p and p' are 5, n, n', k and k' are 0 and m and m' are 6.

In a particular embodiment, the linker is a bivalent linker as shown above wherein r and r' are 4, s and s' are 1, t and v are 0 and X$^1$ and X$^2$ represent C(O)NH. In another embodiment, the linker is a bivalent linker wherein r is 2, r' is 0, s is 1, s' is 0, t and v are 0 and X$^1$ and X$^2$ represent CH$_2$.

In a particular embodiment, the linker is a bivalent linker wherein p and p' are 5, n and n' are 2, k and k' are 1, m and m' are 6, r and r' are 4, s and s' are 1, t and v are 0 and X$^1$ and X$^2$ represent C(O)NH.

In another embodiment, the linker is a bivalent linker wherein p and p' are 5, n and n' are 2, k and k' are 1, m and m' are 6, r is 2, r' is 0, s is 1, s' is 0, t and v are 0 and X$^1$ and X$^2$ represent CH$_2$.

In another embodiment, the linker is a bivalent linker wherein p and p' are 5, n, n', k and k' are 0 and m and m' are 6, r and r' are 4, s and s' are 1, t and v are 0 and X$^1$ and X$^2$ represent C(O)NH.

In another embodiment, the linker is a bivalent linker wherein p and p' are 5, n, n', k and k' are 0 and m and m' are 6, r is 2, r' is 0, s is 1, s' is 0, t and v are 0 and X$^1$ and X$^2$ represent CH$_2$.

In a particular embodiment, the linker is a trivalent linker as shown above wherein p, p' and p" are 5, n, n' and n" are 2, k, k' and k" are 1 and m, m' and m" are 6. In a particular embodiment, the linker is a trivalent linker wherein p, p' and p" are 5, n, n', n", k, k' and k" are 0 and m, m' and m" are 6.

In a particular embodiment, the linker is a trivalent linker as shown above wherein r, r' and r" are 3, s, s' and s" are 1, t is 1, v is 0 and X$^1$, X$^2$ and X$^3$ represent O.

In another embodiment, the linker is a trivalent linker wherein r, r' and r" are 3, s, s' and s" are 1, t is 1, u is 3, v is 1 and X$^1$, X$^2$ and X$^3$ represent O.

In a particular embodiment, the linker is a trivalent linker wherein p, p' and p" are 5, n, n' and n" are 2, k, k' and k" are 1, m, m' and m" are 6, r, r' and r" are 3, s, s' and s" are 1, t is 1, v is 0 and X$^1$, X$^2$ and X$^3$ represent O.

In another embodiment, the linker is a trivalent linker wherein p, p' and p" are 5, n, n' and n" are 2, k, k' and k" are 1, m, m' and m" are 6, r, r' and r" are 3, s, s' and s" are 1, t is 1, u is 3, v is 1 and X$^1$, X$^2$ and X$^3$ represent O.

In another embodiment, the linker is a trivalent linker wherein p, p' and p" are 5, n, n', n", k, k' and k" are 0, m, m' and m" are 6, r, r' and r" are 3, s, s' and s" are 1, t is 1, v is 0 and X$^1$, X$^2$ and X$^3$ represent O.

In another embodiment, the linker is a trivalent linker wherein p, p' and p" are 5, n, n', n", k, k' and k" are 0, m, m' and m" are 6, r, r' and r" are 3, s, s' and s" are 1, t is 1, u is 3, v is 1 and X$^1$, X$^2$ and X$^3$ represent O.

A particular preferred linking group according to the present invention has the following structure:

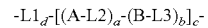

wherein:

A and B represent monomer units independently selected from the group consisting of a monosaccharide, a (C$_1$-C$_{50}$) alkyl and a (C$_2$-C$_{20}$) alkylene glycol;

a and b are integers ranging from 0 to 50;

c is an integer ranging from 0 and 30;

L1, L2 and L3 are linking compounds independently selected from the group consisting of phosphodiester, phosphorothioate, carbonyl (C=O), carbamate, methylphosphonate, guanidinium, sulfamate, sulfamide, formacetal, thioformacetal, sulfone, amide and mixtures thereof; and d is 0 or 1.

In some embodiments, A and B independently represent a (C$_1$-C$_{20}$)alkyl.

The term "(C$_1$-C$_{50}$)alkyl" refers to a straight chain or branched alkyl group having between 1 and 50 carbon atoms. The term "(C$_1$-C$_{20}$)alkyl" refers to a straight chain or branched alkyl group having between 1 and 20 carbon atoms. Examples of alkyl groups include but are not limited to methyl, ethyl, propyl, isopropyl, butyl, isobutyl, t-butyl, pentyl, and hexyl.

In a particular embodiment, the linking group has the structure:

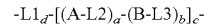

wherein b and d are 0, c is 1, A is an alkyl chain and L2 is a phosphodiester bond.

In a particular embodiment, the linking group has the structure:

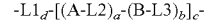

wherein b is 0, c is 1, A is a (C$_1$-C$_{50}$) alkyl, d is 1, L1 is a carbonyl, and L2 is a phosphodiester bond.

A.4. Targeting Moieties of the Conjugates of the Invention

Another modification of the conjugates of the invention involve chemically linking to the nucleic acid or to the protecting group one or more moieties or conjugates which enhance the activity, cellular distribution or cellular uptake of the nucleic acid. Such moieties include but are not limited to lipid moieties such as a cholesterol moiety (Letsinger et al, Proc. Natl. Acid. Sci. USA, 199, 86, 6553-6556), cholic acid (Manoharan et al, Biorg. Med. Chem. Let., 1994 4 1053-1060), a thioether, e.g., beryl-S-tritylthiol (Manoharan et al, Ann. N.Y. Acad. Sci., 1992, 660, 306-309; Manoharan et al, Biorg. Med. Chem. Let., 1993, 3, 2765-2770), a thiocholesterol (Oberhauser et al, Nucl. Acids Res., 1992, 20, 533-538), an aliphatic chain, e.g., dodecandiol or undecyl residues (Saison-Behmoaras et al, EMBO J, 1991, 10, 1111-1118; Kabanov et al, FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al, Tetrahedron Lett., 1995, 36, 3651-3654; Shea et al, Nucl. Acids Res., 1990, 18, 3777-3783), a polyamine or a polyethylene glycol chain (Manoharan et al., Nucleosides and Nucleotides, 1995, 14, 969-973), or adamantane acetic acid (Manoharan et al., Tetrahedron Lett., 1995, 36, 3651-3654), a palmityl moiety (Mishra et ai, Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Alternatively, the moiety capable of enhancing cellular distribution may be a low molecular weight compound or polypeptide which is capable of being specifically translocated across biological barriers by the use of receptor-mediated endocytosis using specific transporters present in said biological barriers. A wide array of uptake receptors and carriers, with an even wider number of receptor-specific ligands, are known in the art. Preferred ligands for receptors that mediates endocytosis and/or transcytosis for use in accordance with present invention include e.g. ligands for, or that specifically bind to the thiamine transporter, folate receptor, vitamin B 12 receptors, asialoglycoprotein receptors, alpha(2,3)-sialoglycoprotein receptor (with e.g., the FC5 and FC44 nanobodies consisting of llama single-domain antibodies (sdAbs) as receptor-specific ligands), transferrin-1 and -2 receptors, scavenger receptors (class A or B, types I, II or III, or CD36 or CD163), low-density lipoprotein (LDL) receptor, LDL-related protein 1 receptor (LRP1, type B), the LRP2 receptor (also known as megalin or glycoprotein 330), diphtheria toxin receptor (DTR, which is the membrane-bound precursor of heparin-binding epidermal growth factor-like growth factor (HB-EGF)), insulin receptor, insulin-like growth factors (IGF) receptors, leptin receptors, substance P receptor, glutathione receptor, glutamate receptors and mannose 6-phosphate receptor.

Preferred ligands that bind to these receptors, for use in accordance with the present invention include e.g. ligands selected from the group consisting of: lipoprotein lipase (LPL), alpha2-macroglobulin (alpha2M), receptor associated protein (RAP), lactoferrin, desmoteplase, tissue- and urokinase-type plasminogen activator (tPA/uPA), plasminogen activator inhibitor (PAI-I), tPA/uPA:PAI-1 complexes, melanotransferrin (or P97), thrombospondin 1 and 2, hepatic lipase, factor Vlla/tissue-factor pathway inhibitor (TFPI), factor VIIIa, factor IXa, Abeta1-40, amyloid-beta precursor protein (APP), Cl inhibitor, complement C3, apolipoprotein E (apoE), *pseudomonas* exotoxin A, CRM66, HIV-I Tat protein, rhinovirus, matrix metalloproteinase 9 (MMP-9), MMP-13 (collagenase-3), spingolipid activator protein (SAP), pregnancy zone protein, antithrombin III, heparin cofactor II, alpha1-antitrypsin, heat shock protein 96 (HSP-96), platelet-derived growth factor (PDGF), apolipoprotein J (apoJ, or clusterin), ABETA bound to apoJ and apoE, aprotinin, angio-pepl, very-low-density lipoprotein (VLDL), transferrin, insulin, leptin, an insulin-like growth factor, epidermal growth factors, lectins, peptidomimetic and/or humanized monoclonal antibodies or peptides specific for said receptors (e.g., sequences HAIYPRH (SEQ ID NO:17) and THRPPMWSPVWP (SEQ ID NO:18) that bind to the human transferrin receptor, or anti-human transferrin receptor (TfR) monoclonal antibody A24), hemoglobin, non-toxic portion of a diphtheria toxin polypeptide chain, all or a portion of the diphtheria toxin B chain (including DTB-His (as described by Spilsberg et al., 2005, Toxicon., 46(8):900-6)), all or a portion of a non-toxic mutant of diphtheria toxin CRM197, apolipoprotein B, apolipoprotein E (e.g., after binding to polysorb-80 coating on nanoparticles), vitamin D-binding protein, vitamin A/retinol-binding protein, vitamin B12/cobalamin plasma carrier protein, glutathione and transcobalamin-B 12.

In a particular embodiment, the conjugate of the invention further comprises a group that facilitates the transport across biological membranes of the conjugate. Preferably, the group is amphipathic. An exemplary agents include, without limitation, penetratin, the fragment of the Tat protein comprising amino acids 48-60, the signal sequence based peptide, PVEC, transportan, amphiphilic model peptide, Arg9, bacterial cell wall permeating peptide, LL-37, cecropin P1, α-defensin, β-defensin, bactenectin, PR-39 and indolicidin. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long.

In another particular embodiment of the invention, the conjugate of the invention further comprises an endosomolytic ligand. Endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In certain embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GAL4 peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68), the INF-7 peptide, the Inf HA-2 peptide, the diINF-7 peptide, the diINF3 peptide, the GLF peptide, the GALA-INF3 peptide and the INF-5 peptide. In certain embodiments, the endosomolytic component may contain a chemical group (e.g., an amino acid) which will undergo a change in charge or protonation in response to a change in pH. The endosomolytic component may be linear or branched.

A.5. Protecting Groups of the Conjugates of the Invention

The nucleic acids forming part of the conjugates of the invention have to be preserved from degrading factors, such as nucleases (endo/exonucleases), during their transport through the different fluids and compartments of the organism. With this aim, the oligonucleotides are designed to resist the enzymatic digestion, and to improve the in vivo stability and bioavailability of the oligonucleotide. Preferably, the nucleic acids are chemically modified by the presence of a group which prevents nuclease-mediated degradation.

For purposes of the present invention, "cap structure" or "protecting group" shall be understood to mean chemical modifications, which have been incorporated at either terminus of the oligonucleotide. Non-limiting examples of the 5'-cap include inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Details are described in WO97/26270, incorporated by reference herein. The 3'-cap includes, for example, 4',5'-methylene nucleotide; 1-(beta-D-erythrofuranosyl) nucleotide: 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inveiled abasic moiety; 5'-phosphoramidate; 5'-phosphorothioate; 1,4-butanediol phosphate; 5 '-amino; bridging and/or non-bridging 5'-phosphoramidate, phosphorothioate and/or phosphorodithioate, bridging or non bridging methylphosphonate and 5'-mercapto moieties. See also Beaucage and Iyer, 1993, Tetrahedron 49, 1925; the contents of which are incorporated by reference herein.

In a preferred embodiment, the cap structure which is attached to the nucleic acid sequence of the conjugates of the invention has the following general structure:

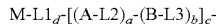

wherein:

M is H, a lipid moiety or a targeting group as defined above;

A and B represent monomer units independently selected from the group consisting of a monosaccharide and a $(C_2-C_{20})$ alkylene glycol;

a and b are integers ranging from 0 to 50;

c is an integer ranging from 0 and 30;

L1, L2 and L3 are linking compounds independently selected from the group consisting of phosphodiester, phosphorothioate, carbamate, methylphosphonate, guanidinium, sulfamate, sulfamide, formacetal, thioformacetal, sulfone, amide and mixtures thereof;

d is 0 or 1.

A lipid moiety, as used herein, refers to a group of organic compounds that has lipophilic or amphipathic properties, including, but not limited to, fats, fatty oils, essential oils, waxes, steroids, sterols, phospholipids, glycolipids, sulpholipids, aminolipids, chromolipids (lipochromes), and fatty acids, The term "lipid" encompasses both naturally occurring and synthetically produced lipids. Lipid moieties usually increase lipophilic properties of the oligonucleotide and facilitate the intracellular uptake in vivo of the oligonucleotide construction. Suitable lipids that can be used include fatty acids; fats; oils; waxes; cholesterol; sterols; fat-soluble vitamins, such as vitamins A, D, E and K; monoglycerides; diglycerides, and phospholipids. Preferred fatty acids are those selected from the group consisting of lauroic acid (C12), myristic acid (C14), palmitic acid (C16), stearic acid (C18), docosanoic acid (C22), and hybrid of lithocholic acid and oleylamine (lithocholic-oleyamine, C43). The lipid may be selected by the skilled person according to the circumstances by taking into consideration the target tissue, the target cell, the administration route, the pathway that the oligonucleotide is expected to follow, etc.

The term "monosaccharide", as used herein and is well known in the art, refers to a simple form of a sugar that consists of a single saccharide unit which cannot be further decomposed to smaller saccharide building blocks or moieties. Preferred sugar moieties for this conjugation group are selected from the group consisting of furanose, fructose, glucose, galactose, mannose, a modified monosaccharide, sialic acid and eritrose and mixtures thereof. The monosaccharides may be in its lineal or cyclic forms (hemiacetalic cyclic isomers). The furanose is any simple sugar containing a five-membered furan-based ring, such as a D-ribose or a fructose residue (D-(–)-fructofuranose). With the combination of the monosaccharides, multiple sugar structures can be attained. The fructooligosaccharides (FOS) and the galactooligosaccharides (GOS) are combinations of special interest, as well as the disaccharides sacarose or lactose; or the polysaccharides inulin, dextrin, starch or glycogen.

The terms "alkylene glycol", "poly(alkylene glycol)" an "alkylene oxide", as used herein, encompasses a family of polyether polymers which share the general formula —O—[$(CH_2)_m$—O—]$_n$—, wherein m represents the number of methylene groups present in each alkylene glycol unit, and n represents the number of repeating units, and therefore represents the size or length of the polymer. The term includes. without limitation, ethylene glycol, propylene glycol, dialkylene glycol (for example, diethylene glycol), trialkylene glycol (for example, triethylene glycol), and glycols such as corresponding mono- and di-alkyl ethers of the aforementioned glycols, wherein the alkyl ethers are lower alkyl ethers having 1 to 6 carbon atoms (for example, methyl, ethyl, propyl ether and the like).

In another embodiment, it has a $(C_2-C_{20})$alkylene glycol monomer unit, which may be any linear or branched molecules from 2 to 20 carbon atoms, or, depending on the values of a and b, a polyalkylene glycol polymer with several $(C_2-C_{20})$ alkylene glycol monomer units. Preferably, the alkylene glycol group is selected from $C_{16}-C_{20}$ alkylene glycol. Still more preferably, the alkylene glycol group is a $C_{18}$ alkylene glycol.

In a particular embodiment, the conjugate of the invention has a cap structure wherein b and d are 0, c is 1, A is an alkyl chain and L2 is a phosphodiester bond.

Protecting groups adequate for the conjugates of the present invention include, without limitation:

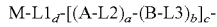

PEG+Sugar, corresponding to the above formula wherein M is H, d is 0, A is PEG, B is a sugar, a and b are each 1 and L3 and L2 are phosphodiester bonds;

PEG+(Sugar)2, corresponding to the above formula wherein A is PEG, B is a sugar, a is 1, b is 2, M is H and d is 0 and L3 and L2 are phosphodiester bonds;

(PEG)2+Sugar, corresponding to the above formula wherein A is PEG, B is a sugar, a is 2, b is 1, M is H and d is 0 and L3 and L2 are phosphodiester bonds;

(PEG)3+Sugar, corresponding to the above formula wherein A is PEG, B is a sugar, a is 3, b is 1, M is H and d is 0 and L3 and L2 are phosphodiester bonds;

(PEG)5+Sugar corresponding to the above formula wherein A is PEG, B is a sugar, a is 5, b is 1, M is H and d is 0 and L3 and L2 are phosphodiester bonds The terms "PEG" and "sugar" are used essentially as described above and include furanose as sugar and a PEG selected from the group of C3, C9 and C18 spacers.

The present invention also contemplates that the conjugate further comprises a protecting group attached to one end or to both ends of the nucleic acid which is not attached to the selectivity agent.

B. Structure of the Conjugates of the Invention

The different elements of the conjugates according to the present invention may be arranged in different manners, which form part of the present invention. Thus, the selectivity agent may be coupled to the 5' end and/or to the 3' end of the nucleic acid. Preferably, the selectivity agent is coupled to the 5' end of the nucleic acid. Moreover, the nucleic acid and the selectivity agent may be directly linked or may be connected by a linker. Similarly, the linker may be coupled to the 5' end and/or to the 3' end of the nucleic acid. Preferably, the linker is coupled to the 5' end of the nucleic acid. Thus, wherein the nucleic acid of the invention contains a single nucleic acid chain, the possible arrangements are:
- a nucleic acid comprising a selectivity agent attached to the 5' end,
- a nucleic acid comprising a selectivity agent attached to the 3' end,
- a nucleic acid comprising a selectivity agent attached to the 5' end and a protecting group attached to the 3' end,
- a nucleic acid comprising a protecting group attached to the 5'end and a selectivity agent attached to the 3' end,
- a nucleic acid modified comprising a first and a second selectivity agent, being said first and second selectivity agents the same or different, both selectivity agents connected to the two ends of a bifunctional linker which is connected to the 5' end of the nucleic acid,
- a nucleic acid modified comprising a first and a second selectivity agent, being said first and second selectivity agents the same or different, both selectivity agents connected to the two ends of a bifunctional linker which is connected to the 3' end of the nucleic acid,
- a nucleic acid modified comprising four selectivity agents, being said selectivity agents the same or different, wherein two of the selectivity agents are connected to both ends of a first bifunctional linker which is connected to the 5' end of the nucleic acid end and wherein two of the selectivity agents are connected to both ends of a second bifunctional linker which is connected to the 3' of the nucleic acid.

In a preferred embodiment, wherein the conjugate contains a single nucleic acid chain and two selectivity agents, the first selectivity agent and the second selectivity agents are both a triple reuptake inhibitors (preferably indatraline) and are connected to the 5' and 3' ends of the nucleic acid.

In another preferred embodiment, wherein the conjugate contains a single nucleic acid chain and two selectivity agents, the first selectivity agent is a serotonin reuptake inhibitor (SRI) (preferably sertraline) and the second selectivity agent is a norepinephrine dopamine double reuptake inhibitor (NDRI) and are connected to the 5' end of the nucleic acid. In a more preferred embodiment, the SRI is connected to the 5' end of the nucleic acid and the NDRI is connected to the 3' end of the nucleic acid. In another preferred embodiment, the SRI is connected to the 3' of the nucleic acid and the NDRI is connected to the 5' end of the nucleic acid.

In another embodiment, the nucleic acid may contain more than one ligand attached to one end of the nucleic acid molecule by virtue of a multifunctional linker. Thus, in another embodiment, the nucleic acid may contain a bifunctional linker attached to the 5' end, wherein each end of the bifunctional linker is coupled to a triple reuptake inhibitor (preferably indaraline). In another embodiment, the nucleic acid may contain a bifunctional linker attached to the 5' end, wherein a first end of the bifunctional linker is coupled to a SRI (preferably sertonin) and the second end of the bifunctional linker is connected to a NDRI.

In another embodiment, the nucleic acid contains a trifunctional linker attached to either the 5' or 3' end, wherein each end of the trifunctional linker is attached to a ligand. In a preferred embodiment, the three ends of the trifunctional linker are connected to triple reuptake inhibitors, which can be the same or different. In a preferred embodiment, the nucleic acid molecule is connected to three indatraline molecules.

In addition, the conjugate of the invention may contain more than one nucleic acid chain that modulates the expression of the target molecule. For example, a construction of this invention can contain up to five different nucleic acids joined in tandem through phosphodiesters targeted at different regions of a given target molecule.

Moreover, in those cases wherein the nucleic acid is a double stranded nucleic acid, the selectivity agent may be coupled to the sense and/or to the antisense strand and may be directly coupled or connected by a linker group.

The nucleic acids forming part of the conjugates of the invention have to be protected from degrading factors, such as nucleases (endo/exonucleases), during their transport through the different fluids and compartments of the organism. With this aim, the oligonucleotides are designed to resist the enzymatic digestion, and to improve the in vivo stability and bioavailability of the oligonucleotide. Cellular exonucleases use free 5' ends as targets. Thus, in the case of single stranded nucleic acid, the selectivity agent may act as a stabilizing moiety when coupled to the 5' of the nucleic acid. However, in the case of conjugates comprising a double stranded nucleic acids or a single stranded nucleic acid in which the selectivity agent is linked to the 3' end, the conjugate may further comprise an stabilising moiety or cap structure which is usually a group which prevents degradation of the nucleic acid by the activity of exonucleases. In the case of double stranded nucleic acids, the following possible arrangements exist:

[1] the selectivity agent is attached to the 5' end of one of the strands, in which case it is useful to attach a cap structure to the 5' end of the opposite strand. Additionally, a cap structure may also be present in one or two of the 3' ends.

[2] the selectivity agent is attached to the 3' end of one of strands, in which case it is is useful to attach a cap structure to the 5' ends of the sense and of the antisense strand. Additionally, a cap structure may be present at the free 3' end.

[3] the conjugate comprising more than one selectivity agent which may be the same or different in which case, the selectivity agents are coupled to the 5' ends of the sense and of the antisense strand. Optionally, a cap structure may be coupled to one or two of the free 3' ends.

In a preferred embodiment, the nucleic acid is a double stranded RNA wherein the selectivity agent is linked to the 5' end of the antisense strand and the protecting group is linked to the 5' end of the sense strand. In a still more preferred embodiment, the protecting group has the structure

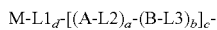

M-L1$_d$-[(A-L2)$_a$-(B-L3)$_b$]$_c$- wherein M is H, d is 0, A is a C18 spacer of polyethylene glycol, B is a furanose, a is 2, b and c are 1 and L2 and L3 are phosphodiester bonds In another embodiment, the nucleic acid may contain more than one ligand attached to one end of one of the nucleic acid strands by virtue of a multifunctional linker. Preferably, the ligands are attached to the 5' ends of either the sense or the antisense strands. Thus, in another embodiment, the nucleic acid may contain a bifunctional linker attached to the 5' end of the sense strand, wherein each end of the bifunctional linker is coupled to a triple reuptake inhibitor (preferably indaraline). In another embodiment, the nucleic acid may contain a bifunctional linker attached to the 5' end of the sense strand, wherein a first end of the bifunctional linker is coupled to a SRI (preferably sertonin) and the second end of the bifunctional linker is connected to a NDRI. In another embodiment, the nucleic acid may contain a bifunctional linker attached to the 5' end of the antisense strand, wherein each end of the bifunctional linker is coupled to a triple reuptake inhibitor (preferably indatraline). In another embodiment, the nucleic acid may contain a bifunctional linker attached to the 5' end of the antisense strand, wherein a first end of the bifunctional linker is coupled to a SRI (preferably sertonine) and the second end of the bifunctional linker is connected to a NDRI.

In another embodiment, the nucleic acid contains a trifunctional linker attached to either the 5' or 3' end of either the sense strand, the antisense strand or both, wherein each end of the trifunctional linker is attached to a ligand. In a preferred embodiment, the three ends of the trifunctional linker are connected to triple reuptake inhibitors, which can be the same or different. In a preferred embodiment, the 5' end of the sense nucleic acid strand is connected to three indatraline molecules.

The conjugate of the invention comprises
(i) at least one selectivity agent which binds specifically to one or more neurotransmitter transporters selected from the group consisting of a dopamine transporter (DAT), serotonin transporter (SERT) or a norepinephrine transporter (NET) and
(ii) at least one nucleic acid which is capable of specifically binding to a target molecule which is expressed in the same cell as the neurotransmitter transporter wherein said target molecule is α-synuclein or the mRNA encoding α-synuclein In a more preferred embodiment, the conjugate of the invention has the structure (III)

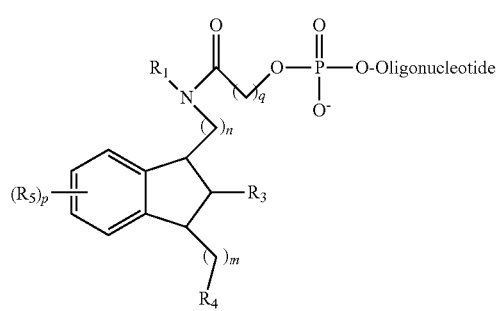

(III)

wherein
n or m are integers each having a value between 0 and 6, inclusive;
p is an integer having a value between 0 and 4, inclusive;
q is an integer having a value between 0 and 20 inclusive;
$R_1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_A$; —CO$_2$$R_A$; —C(=O)N($R_A$)$_2$ or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO$_2$R$_C$; —CN; —SCN; —SR$_C$; —SOR$_A$; SO$_2$R$_C$; —NO$_2$; —N$_3$; —N(R$_C$)$_2$; —NHC(=O)R$_C$; —NR$_C$C(=O)N(R$_C$)$_2$; —OC(=O)OR$_C$; —OC(=O)R$_C$; —OC(=O)N(R$_C$)$_2$; —NR$_C$C(=O)OR$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is substituted or unsubstituted, branched or unbranched aryl; or substituted or unsubstituted, branched or unbranched heteroaryl;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_E$; —C(=O)R$_E$; —CO$_2$R$_E$; —CN; —SCN; —SR$_E$; —SOR$_E$; SO$_2$R$_E$; —NO$_2$; —N$_3$; —N(R$_E$)$_2$; —NHC(=O)R$_E$; —NR$_E$C(=O)N(R$_E$)$_2$; —OC(=O)OR$_E$; —OC(=O)R$_E$; —OC(=O)N(R$_E$)$_2$; —NR$_E$C(=O)OR$_E$; or —C(R$_E$)$_3$ wherein each occurrence of R$_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable forms thereof.

In an embodiment of the conjugate of the invention, the oligonucleotide is an antisense oligonucleotide or a gapmer. In a preferred embodiment, the gapmer of the conjugate of the invention comprises a central block of 10 deoxynucleotides flanked by 2 blocks of 4 2'-Omethyl modified ribonucleotides.

In a particular preferred embodiment of the conjugate according to the invention, the oligonucleotide is capable of specifically binding to the mRNA encoding α-synuclein in a region selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7). In a more preferred embodiment, the gapmer consists of a sequence selected from the group consisting of SEQ ID NO:1, SEQ ID NO:2 and SEQ ID NO:3.

In a particular embodiment of the conjugate of the invention, the selectivity agent has the structure (II):

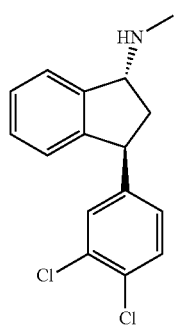

(II)

In a preferred embodiment, the conjugate of the invention has the following structure (IV):

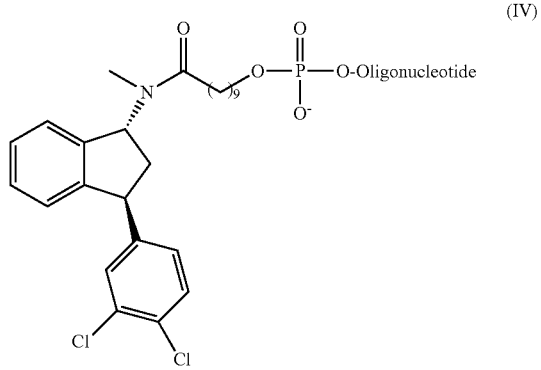

(IV)

wherein the oligonucleotide comprises a nucleic acid which is capable of specifically binding to the mRNA encoding α-synuclein in a region selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7). In particular embodiment, the oligonucleotide has a sequence selected from the group consisting of SEQ ID NO:1, SEQ ID NO:2 and SEQ ID NO:3.

In yet another preferred embodiment, the conjugate of the invention comprises a double stranded nucleic acid wherein the 5' end of the sense strand is coupled to the protecting group and the 5' end of the antisense strand is coupled to the selectivity agent and wherein the protecting group has the structure:

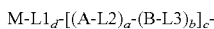

M-L1$_d$-[(A-L2)$_a$-(B-L3)$_b$]$_c$- wherein M is H, d is 0, A is a C18 spacer of polyethylene glycol, B is a furanose, a is 2, b and c are 1 and L2 and L3 are phosphodiester bonds.

In the sense of the invention, the protecting group may be linked to the 5'-OH or 3'-OH groups of the oligonucleotide by means of the linking compound.

For instance, it is possible to link into a single oligonucleotide molecule a variable number of groups of formula (II), typically from 2 to 4, depending if the oligonucleotide is double-stranded or single-stranded with the proviso that the linking is made through the 5'-OH and/or 3'-OH. It is also possible that a chain of several groups of formula (I) are linked to the oligonucleotide, said groups of formula (I) being linked to each other by means of linking compounds, such as phosphoramidite derivated ones that produce a phosphodiester bond between the molecules and/or the oligonucleotide. Also, the oligonucleotide construction may contain a chain of several groups of formula (I) linked to one end of the oligonucleotide and another group of formula (I) linked to another end of the oligonucleotide.

Also, the nucleotide constructions of the invention can contain more than one selectivity agent, distributed with all the possible combinations among the 5'-OH and 3'-OH termini of the two strands of the oligonucleotide or joined to the group of formula (I). Moreover, if there is more than one selectivity agent, these can be linked in tandem to the group of formula (I) and/or the oligonucletide.

If the oligonucleotide construction contains more than one selectivity agent, different combinations are possible. For instance, the protecting group can be linked to the 5'-OH or 3'-OH terminal groups of one of the strands of the oligonucleotide. Another possible combination includes a selectivity agent linked to the 5'-OH group of one oligonucleotide strand and a series of aptamers joined to the terminal unit of the group formula (I) that is bound to the other oligonucleotide strand.

C. Pharmaceutical Compositions of the Invention

The inventors have found that the conjugates of the invention have the ability of modulating the expression of alpha-synuclein mRNA targeted by the nucleic acid sequences of the conjugates of the invention. In particular, the conjugates comprising gapmers targeting regions 448-465 (SEQ ID NO:4), 499-516 (SEQ ID NO:5) and 502-519 (SEQ ID NO:6) of the human alpha-synuclein mRNA as in NCBU accession number NM_000345 can effectively induce a reduction of alpha-synuclein expression in olfactory bulbs (BO), substantia nigra (SNc/VTA), dorsal raphe (DR) (see Example 3 and FIG. 4).

Thus, the skilled person will appreciate that the conjugates of the invention are adequate for the treatment of diseases which may benefit from the reduction in the expression levels of the genes which are targeted by the nucleic acids present in the conjugates of the invention, i.e. the expression levels of alpha-synuclein. Thus, in another aspect, the invention relates to a conjugate according to the invention for use in medicine. Alternatively, the invention relates to the use of a conjugate according to the invention for the manufacture of a medicament. Additionally, the invention also relates to a pharmaceutical composition comprising a conjugate according to the invention and a pharmaceutically-acceptable excipient.

Appropriate amounts of oligonucleotide constructions of the invention can be formulated with pharmaceutically acceptable excipients and/or carriers to obtain a pharmaceutical composition. A composition that includes a conjugate according to the invention can be delivered to a subject by a variety of routes. Exemplary routes include intrastriatal, intracerebroventricular, intrathecal, intraparenchymal (e.g., in the striatum), intranasal, and ocular delivery. The composition can also be delivered systemically, e.g., by intravenous, subcutaneous or intramuscular injection, which is particularly useful for delivery of the conjugates to peripheral neurons. Additionally, it is also possible to administer the conjugates of the invention intranasally which allows systemic administration by a non-aggressive mode of administration. Also, intraventricular administration may also be adequate. A preferred route of delivery is directly to the brain, e.g., into the ventricles or the hypothalamus of the brain, or into the lateral or dorsal areas of the brain.

The pharmaceutical compositions of the invention may comprise a plurality of different conjugates, wherein the different conjugates comprise nucleic acids which target different regions of the same target molecule. Thus, the pharmaceutical compositions may comprises at least 2, at least 3, at least 4, at least 5, at least 6 or more different conjugates comprising each a different nucleic acid.

Those of skill in the art are familiar with the principles and procedures discussed in widely known and available sources such as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990) both of which are incorporated herein by reference.

In a preferred embodiment of the present invention, the conjugates are formulated in accordance with standard procedure as a pharmaceutical composition adapted for delivered administration to human beings and other mammals. Typically, compositions for intravenous or intraventricular administration are solutions in sterile isotonic aqueous buffer.

Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., and inert carriers having well established functionality in the manufacture of pharmaceuticals. Various delivery systems are known and can be used to administer a therapeutic of the present invention including encapsulation in liposomes, microparticles, microcapsules and the like.

In yet another preferred embodiment, therapeutics containing the conjugates of the invention can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, triethylamine, 2-ethylamino ethanol, histidine, procaine or similar.

D. Therapeutic Uses of the Conjugates of the Invention

The conjugates of the invention can be used for the treatment of any disease which can be improved by knocking down alpha-synuclein gene in a cell that expresses a neurotransmitter transporter selected from the group consisting of DAT, SERT and NET. The skilled person will understand that the conjugates are useful for the treatment of diseases characterized by abnormal expression of the protein alpha-synuclein in a cell (e.g. accumulation of α-synuclein in Lewy bodies) or for diseases wherein the alpha-synuclein protein is expressed at normal levels but which can be improved by decreasing the expression of said target protein.

Thus, in another aspect, the invention relates to a conjugate of the invention comprising
 i) at least one selectivity agent which binds specifically to one or more neurotransmitter transporters selected from the group consisting of a dopamine transporter (DAT), serotonin transporter (SERT) or a norepinephrine transporter (NET) and
 ii) at least one nucleic acid which is capable of specifically binding to a target molecule which is expressed in the same cell as the neurotransmitter transporter wherein said target molecule is α-synuclein or the mRNA encoding α-synuclein
for use in the treatment or prevention of a disease associated with the deposition of Lewy bodies.

Alternatively, the invention relates to the use of a conjugate according to the invention for the manufacture of a medicament for the treatment of a disease associated with the deposition of Lewy bodies.

Alternatively, the invention relates to a method for the prevention and/or treatment of a disease associated with the deposition of Lewy bodies in a subject in need thereof that comprises administration to said subject of a therapeutically effective amount of a conjugate according to the invention.

The term "disease associated with the deposition of Lewy bodies" refers to a condition which is characterised by disorders of alpha-synuclein metabolism, which gives rise to the formation of abnormal neuronal alpha-synuclein inclusions. More particular Lewy body disorders include Parkinson's disease (PD), dementia with Lewy bodies (DLB), PD with dementia (PDD) and multiple system atrophy. In a particular embodiment, the disease associated with the deposition of Lewy bodies is selected from the group consisting of Parkinson's disease, dementia with Lewis bodies and multiple system atrophy.

Parkinson's disease (PD) is a degenerative disorder of the central nervous system that often impairs the patient's motor skills, speech, and other functions. The symptoms of Parkinson's disease result from the greatly reduced activity of dopaminergic cells in the pars compacta region of the substantia nigra (SNpc). These neurons project to the striatum and their loss leads to alterations in the activity of the neural circuits within the basal ganglia that regulate movement, in essence an inhibition of the direct pathway and excitation of the indirect pathway. The direct pathway facilitates movement and the indirect pathway inhibits movement, thus the loss of these cells leads to a hypokinetic movement disorder. The lack of dopamine results in increased inhibition of the ventral anterior nucleus of the thalamus, which sends excitatory projections to the motor cortex, thus leading to hypokinesia.

PD is characterized by a progressive loss of dopaminergic neurons in the SNpc and the presence of intracellular inclusions designated as Lewy bodies (LB). Neurochemically, PD is marked by mitochondrial complex I dysfunction and increased indices of oxidative stress. Several pathogenic mechanisms have been proposed for PD including oxidative and nitrosative stress, mitochondrial dysfunction, protein misfolding and aggregation, and apoptosis. PD is mostly sporadic but some of the PD cases have been shown to be familial-linked. The first familial-linked PD gene identified was α-synuclein (α-syn) which in fact is the major component of LB in all PD patients. The normal function of α-synuclein is poorly understood. α-Synuclein can bind to lipids and, in neurons, is associated with presynaptic vesicles and the plasma membrane, possibly via lipid rafts. The deposited, pathological forms of α-synuclein are aggregated and show lower solubility than the normal protein. Three point mutations have been described to cause familial PD, but also duplications and triplications of the SNCA gene have been reported to be responsible of PD and Lewy body disease. Therefore, even without sequence variants, α-synuclein dosage can be causal for Lewy body disease.

Dementia with Lewy bodies (DLB) is also known as Lewy body dementia, diffuse Lewy body disease, cortical Lewy body disease or senile dementia of Lewy type. This disease is closely related to Alzheimer's and Parkinson's diseases and is anatomically characterized by the presence of Lewy bodies, which are clumps of alpha-synuclein and ubiquitin protein in neurons detectable in post mortem brain histology.

Multiple system atrophy or MSA is a neurodegenerative disorder associated with the degeneration of nerve cells in specific brain areas. As a result of cell degeneration, problems with movement, balance, and other autonomic functions of the body such as bladder control or blood-pressure regulation arise in the patient.

In a particular preferred embodiment, the conjugate according to the invention is administered intraventricularly or intranasally.

E. Synthesis of the Conjugates of the Invention

The conjugates of the invention are typically synthesized using standard procedures in organic synthesis. The skilled person will appreciate that the exact steps of the synthesis will depend on the exact structure of the conjugate which has to be synthesized. For instance, if the conjugate comprises a single nucleic acid strand conjugated to the selectivity agent through its 5' end, then the synthesis is usually carried out by contacting an amino-activated oligonucleotide and a reactive activated selectivity reagent.

Wherein the conjugate comprises a double stranded nucleic acid, then the sense and antisense strands are synthesized separately and annealed in vitro using standard molecular biology procedures. In a typical conjugate, the first nucleic acid strands carries the selectivity agent and the second nucleic acid strands carries a protecting group. In a still more preferred embodiment, the selectivity agent is coupled to the 5' end of the first nucleic acid strand and/or the protecting group is attached to the 5' end of the second nucleic acid strand, although the attachment of the selectivity agent or of the protecting group can also be carried out at the 3' ends of the nucleic acid strands.

Synthesis of the conjugates can be carried out as follows:

[1] Conjugates having the structure

Selectivity agent-[Oligonucleotide]-3' are typically synthesized using the following steps:
(i) Activating the selectivity agent. Preferably, the activation group in the selectivity agent is a succinimide group or an amino group; If the selectivity agent carries a primary or secondary amine, the activation may not be needed since the activated oligonucleotide may react with the amino group in the selectivity agent.
(ii) Activating the oligonucleotide on its 5' end. Preferably, the activation group in the oligonucleotide is an amino group (wherein the selectivity agent has been activated by a succinimide group) or a carboxyl group (wherein the selectivity agent has been activated by an amine group or contains an amino group) and
(iii) contacting the activated selectivity agent with the activated oligonucleotide under conditions adequate for the reaction between the two activation groups.

[2] Conjugates having the structure

```
Protecting group-[Sense strand]-3'
              3'-[Antisense strand]-
                 Selectivity agent
``` are typically synthesized using the following steps:
(i) Activating the selectivity agent. Preferably, the activation group in the selectivity agent is a succinimide or an amino group,
(ii) Activating the sense strand on its 5' end. Preferably, the activation group in the oligonucleotide is an amino group (wherein the selectivity agent has been activated by a succinimide group) or a carboxyl group (wherein the selectivity agent has been activated by an amine group),
(iii) contacting the activated selectivity agent with the activated sense strand under conditions adequate for the reaction between the two activation groups,
(iv) Adding the protecting group to the immobilised antisense strand. This step is preferably carried out using an oligonucleotide which reactive groups are blocked by acetylation or benzylation (the furanose groups), 2-cyanoethylation (the phosphodiester linkages) and 9-H-fluorenylmethoxycarbonyl (Fmoc) (the exocyclic amino groups).
(v) Annealing the sense and antisense strands The conjugates of the invention can be prepared using techniques known by those skilled in the art. The synthesis of conjugates may involve the selective protection and deprotection of functional groups. Suitable protecting groups are well known to the skilled person in the art. For example, a general review of protecting groups in organic chemistry is provided by Wuts, P. G. M. and Greene T. W. in *Protecting Groups in Organic Synthesis* (4$^{th}$ Ed. Wiley-Interscience), and by Kocienski P. J. in *Protecting Groups* (3$^{rd}$ Ed. Georg Thieme Verlag).

In the context of the present invention, the following terms have the meaning detailed below:

The term "$C_1$-$C_6$ alkyl" relates to a linear or branched hydrocarbon radical consisting of carbon and hydrogen atoms, which does not contain unsaturation, having one to six, preferably one to three ($C_1$-$C_3$ alkyl), carbon atoms and which is joined to the rest of the molecule by a single bond. Examples of alkyl groups include but are not limited to alkyl groups such as methyl, ethyl, propyl, isopropyl, butyl, isobutyl, t-butyl, pentyl and hexyl. Preferably alkyl refers to methyl.

The term "halogen" refers to bromo, chloro, iodo or fluoro.

The term "haloalkyl" refers to an alkyl group as defined above wherein at least one hydrogen atom has been replaced by halogen. Examples of haloalkyl groups include but are not limited to $CF_3$, $CCl_3$, $CHF_2$, $CF_2CF_3$. Preferably haloalkyl refers to $CF_3$.

The term "$C_6$-$C_{10}$ aryl" refers to an aromatic group having between 6 and 10 carbon atoms, comprising 1 or 2 aromatic nuclei, bound by means of a carbon-carbon bond or fused, including for example phenyl, naphthyl and diphenyl. Preferably "aryl" refers to phenyl.

The term "heterocyclyl" refers to a stable 3- to 10-membered ring radical, preferably a 5- or 6-membered ring, which consists of carbon atoms and from one to five heteroatoms selected from the group consisting of nitrogen, oxygen, and sulphur and which can be partially or fully saturated or aromatic ("heteroaryl"). For the purposes of this invention, the heterocycle can be a monocyclyl, bicyclyl or tricyclyl ring system, which can include systems of fused rings. In a particular embodiment, the heterocyclyl group is succinimide.

The compounds of the present invention represented by the above described formula (III) may include stereoisomers depending on the presence of chiral centres. The single isomers, enantiomers or diastereoisomers and mixtures thereof fall within the scope of the present invention.

Unless otherwise indicated, the compounds used in the invention are intended to include compounds that only differ in the presence of one or more isotopically enriched atoms. For example, compounds having the present structures except for the substitution of a hydrogen with deuterium or tritium, or the substitution of a carbon with a $^{13}$C- or $^{14}$C-enriched carbon or a $^{15}$N-enriched nitrogen are within the scope of this invention.

Synthesis Using an Amino-Derivatized Nucleic Acid and an Activated Triple Reuptake Inhibitor In a first embodiment, the conjugates according to the invention may be obtained by coupling an amino-derivatized nucleic acid to an activated derivative form of a compound with structure (I) or analog thereof. In a particular embodiment, the activated derivative form is a derivative of a compound with structure (I) wherein $R_2$ is H, according to the following structure (VII):

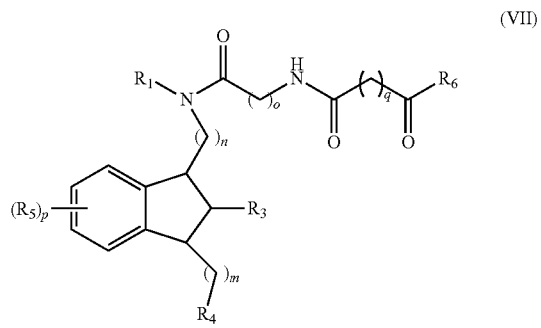

(VII)

wherein n or m are integers each having a value between 0 and 6, inclusive;

p is an integer having a value between 0 and 4, inclusive;

q is an integer having a value between 0 and 20 inclusive;

$R_1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_A$; —CO$_2$$R_A$; —C(=O)N($R_A$)$_2$ or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_C$; —C(=O)$R_C$; —CO$_2$$R_C$; —CN; —SCN; —S$R_C$; —SO$R_C$; SO$_2$$R_C$; —NO$_2$; —N$_3$; —N($R_C$)$_2$; —NHC(=O)$R_C$; —NR$_C$C(=O)N($R_C$)$_2$; —OC(=O)O$R_C$; —OC(=O)$R_C$; —OC(=O)N($R_C$)$_2$; —NR$_C$C(=O)O$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is substituted or unsubstituted, branched or unbranched aryl; or substituted or unsubstituted, branched or unbranched heteroaryl;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_E$; —C(=O)$R_E$; —CO$_2$$R_E$; —CN; —SCN; —S$R_E$; —SO$R_E$; SO$_2$$R_E$; —NO$_2$; —N$_3$; —N($R_E$)$_2$; —NHC(=O)$R_E$; —NR$_E$C(=O)N($R_E$)$_2$; —OC(=O)O$R_E$; —OC(=O)$R_E$; —OC(=O)N($R_E$)$_2$; —NR$_E$C(=O)O$R_E$; or —C($R_E$)$_3$ wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety and $R^6$ is a carbonyl activating radical.

The term "carbonyl activating radical" refers to a substituent of a carbonyl that renders that carbonyl prone to nucleophilic addition. In a particular embodiment, it forms, together with the carbonyl group, an anhydride, an acid halide or an ester group. In a preferred embodiment, the carbonyl activating radical is selected from halogen, —OC(O)R, —OR', —SR"; wherein R, R' and R" are independently selected from $C_1$-$C_6$ alkyl, haloalkyl, heterocyclyl, aryl and heteroaryl.

The term "carbonyl activating group" refers to a compound that converts the carbonyl of a carboxylic acid group to one that is more prone to nucleophilic addition, such as e.g. anhydrides, carboxylic acid halides, carbodiimides, halogenating agents, disulfides, etc. In a particular embodiment, the carbonyl activating group is selected from halogenating agent, R(O)COC(O)R, RC(O)halogen, R'OH, R"SH, R"SSR"; wherein R, R' and R" are independently selected from $C_1$-$C_6$ alkyl, haloalkyl, heterocyclyl, aryl and heteroaryl.

In a particular embodiment, the carbonyl activating group is N-hydroxysuccinimide. In this case, the reaction is preferably performed in the presence of a further carbonyl activating group.

Carbonyl activating group suitable for this process include carbodiimides, such as dicyclohexylcarbodiimide (DCC) and diisopropylcarbodiimide (DIC) and triazoles, such as 1-hydroxy-benzotriazole (HOBt) and 1-hydroxy-7-aza-benzotriazole (HOAt). In a preferred embodiment, the compound of formula (VII) is reacted with N-hydroxysuccinimide in the presence of diisopropylcarbodiimide to afford the activated derivative.

In a particular embodiment, $R^6$ is a succinimidoxy group. Therefore, in another embodiment, the conjugates according to the invention may be obtained by coupling a amino-derivatized nucleic acid to an activated derivative form of sertraline or analog thereof, wherein the activated derivative of a selectivity agent is a compound of formula (VIII):

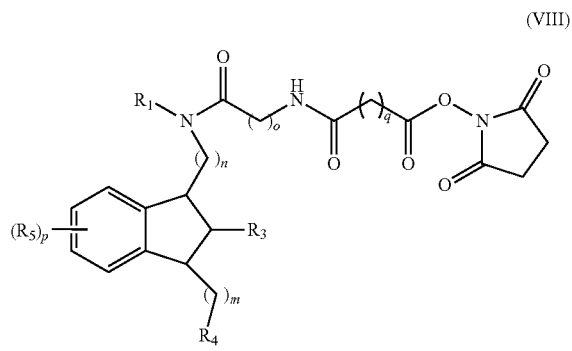

(VIII)

wherein $R_1$, $R_3$, $R_4$, $R_5$, $R_6$, n, m, p and q are as defined above

According to a particular embodiment, the activated compound of formula (VIII) is the compound:

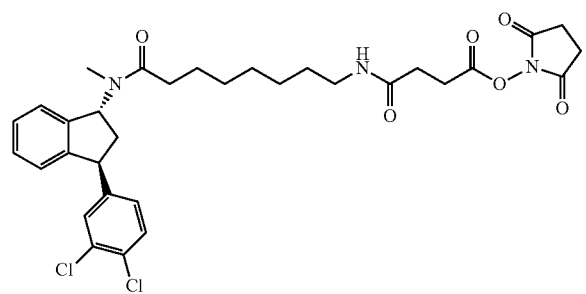 [SMILES: CN(C(=O)CCCCCCCNC(=O)CCC(=O)ON1C(=O)CCC1=O)[C@@H]1C[C@@H](c2ccc(Cl)c(Cl)c2)c2ccccc21]

According to one embodiment, the compounds of according to the invention may be prepared by a sequence comprising:

a) reacting a compound of formula (V)

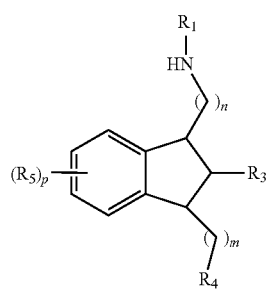

and an acylating agent of formula (IX):

(IX)

wherein p is as defined above, Z is halogen or OH and PG is an amine protecting group to yield a compound of formula (X)

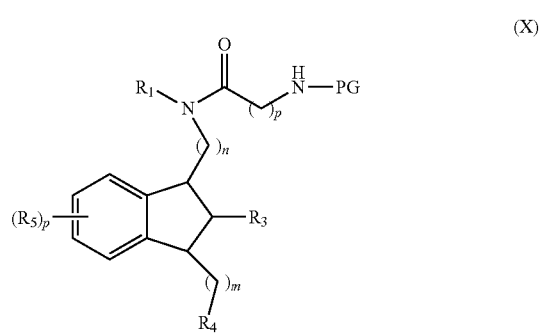

(X)

Commonly used protecting groups for amines include carbamates, such as tert-butyl, benzyl, 2,2,2-trichloroethyl, 2-trimethylsilylethyl, 9H-fluorenylmethyl (Fmoc), allyl or nitrophenyl carbamates; amides, such as formamides, acetamides, trifluoroacetamides, sulfonamides, trifluoromethanesulfonyl amides or tert-butylsulfonyl amides; and aryl or arylakylamines, such as p-methoxyphenyl, benzyl, p-methoxybenzyl, 3,4-dimethoxybenzyl, dimethoxytrityl or monomethoxytrityl amines. In a particular embodiment, the acylating agent of formula (IX) is 9H-fluorenylmethoxycarbonyl-6-aminohexanoic acid.

Compounds of formula (V) can in turn be prepared for example as described in U.S. Pat. No. 6,455,736. In particular, when the compound of formula (V) is sertraline, it can be obtained from the corresponding chlorohydrate (commercially available) by treatment with a suitable base, including organic or inorganic bases such a alkali or alkaline earth carbonates or hydroxides, ammonia or amines, such as trimethylamine, triethylamine, diisopropylethylamine, pyridine, piperidine, morpholine and the like.

b) deprotecting the amino protecting group in the compound of formula (V) to yield a compound of formula (XI):

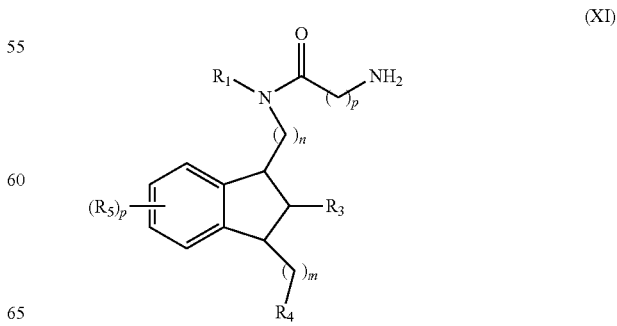

(XI)

Suitable deprotecting conditions are known to the skilled person, for example in *Protecting Groups in Organic Synthesis* (Wuts, P. G. M. and Greene T. W., 4$^{th}$ Ed. Wiley-Interscience) and in *Protecting Groups* (Kocienski P. J., 3$^{rd}$ Ed. Georg Thieme Verlag). In a particular embodiment, the protecting group is removed in the presence of an amine, such as piperidine, morpholine, dicyclohexylamine, diisopropylethylamine or dimethylaminopyridine, preferably in the presence of piperidine.

c) reacting the compound of formula (XI) with an acylating agent of formula (XII) or (XIII):

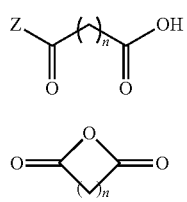

(XII)

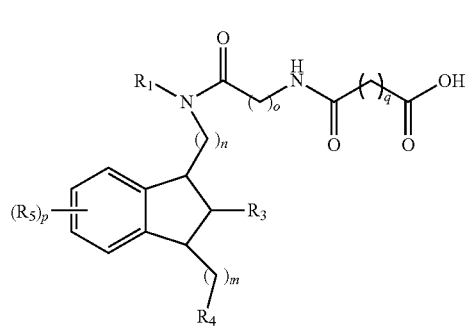

(XIII)

wherein n is as defined above and Z is halogen or OH, leading to a compound of formula (XIV):

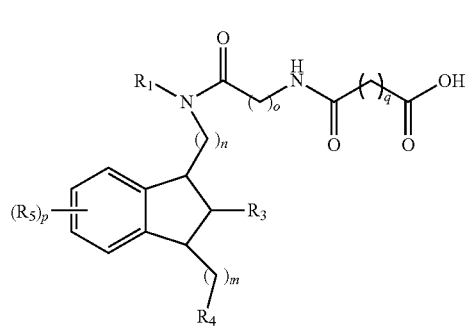

(XIV)

In a particular embodiment, the acylating agent is succinic anhydride, d) treating a compound of formula (XIV) with a carbonyl activating group.

The term "carbonyl activating group" refers to a compound that converts the carbonyl of a carboxylic acid group to one that is more prone to nucleophilic addition, such as e.g. anhydrides, carboxylic acid halides, carbodiimides, halogenating agents, disulfides, etc. In a particular embodiment, the carbonyl activating group is selected from halogenating agent, R(O)COC(O)R, RC(O)halogen, R'OH, R"SH, R"SSR"; wherein R, R' and R" are independently selected from C$_1$-C$_6$ alkyl, haloalkyl, heterocyclyl, aryl and heteroaryl.

In a particular embodiment, the carbonyl activating group is N-hydroxysuccinimide. In this case, the reaction is preferably performed in the presence of a further carbonyl activating group.

Therefore, in a particular embodiment, step d) comprises treating a compound of formula (XIV) with N-hydroxysuccinimide in the presence of a further carbonyl activating group.

Carbonyl activating group suitable for this process include carbodiimides, such as dicyclohexylcarbodiimide (DCC) and diisopropylcarbodiimide (DIC) and triazoles, such as 1-hydroxy-benzotriazole (HOBt) and 1-hydroxy-7-aza-benzotriazole (HOAt). In a preferred embodiment, the compound of formula (XIV) is reacted with N-hydroxysuccinimide in the presence of diisopropylcarbodiimide to afford the activated derivative.

According to another aspect, the invention is directed to an intermediate of formula (X),

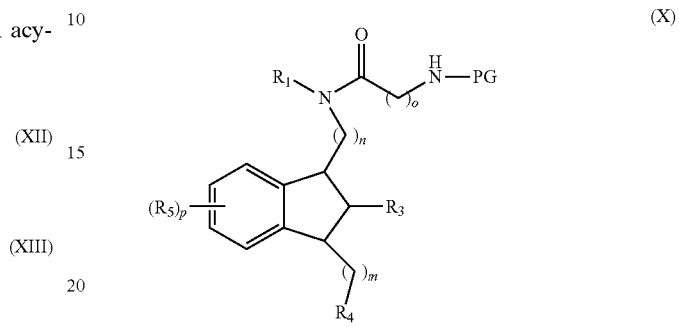

(X)

wherein R$^1$-R$^5$, m, n, o, p and PG are as defined above.

In a preferred embodiment, R$^1$ is methyl, R$^2$-R$^5$ are hydrogen, X and Y are chloride, W is hydrogen, p is 5 and PG is 9H-fluorenylmethoxycarbonyl. More preferably, the compound of formula (X) is compound:

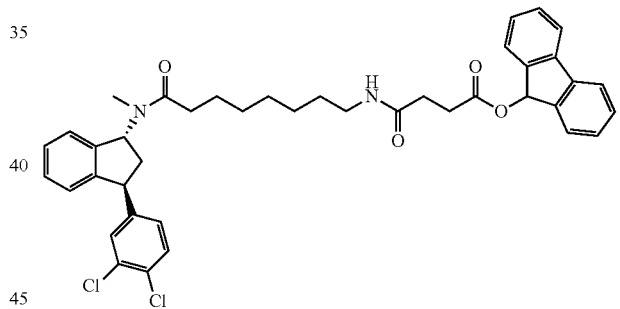

According to another aspect, the invention is directed to an intermediate of formula (XI),

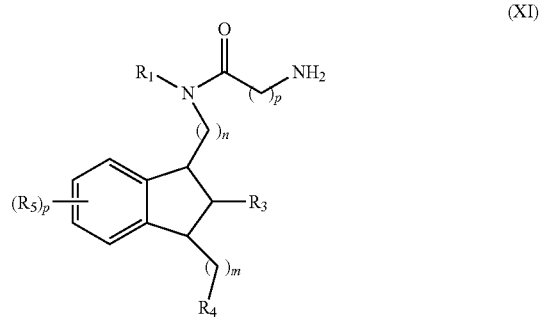

(XI)

wherein R$^1$-R$^5$, m, n, o and p are as defined above.

More preferably, the compound of formula (VII) is compound:

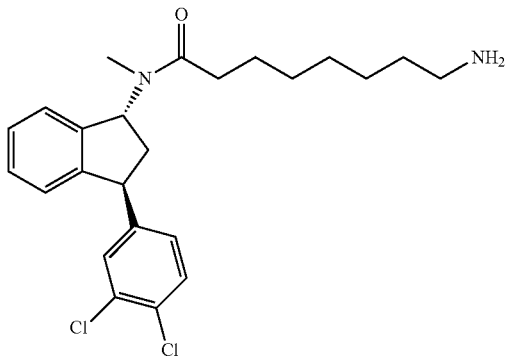 [SMILES: CN(C(=O)CCCCCCCN)[C@@H]1C[C@@H](c2ccc(Cl)c(Cl)c2)c2ccccc21]

More preferably, the compound of formula (VII) is:

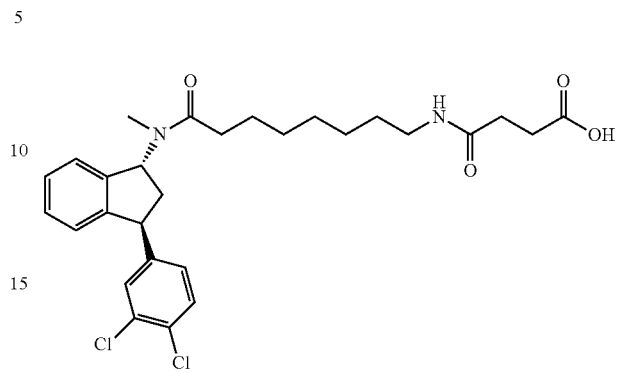

According to another aspect, the invention is directed to an intermediate of formula (XIV)

According to another aspect, the invention is directed to an intermediate of formula (XV),

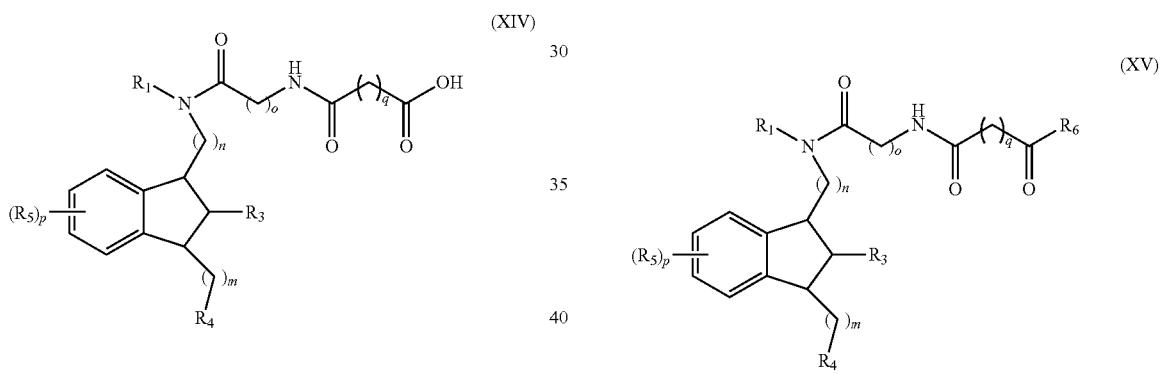

wherein $R^1$-$R^5$, m, n, o, p and q are as defined above wherein $R^1$-$R^6$, m, n, o, p and q are as defined above.

More preferably, the compound of formula (XV) is compound:

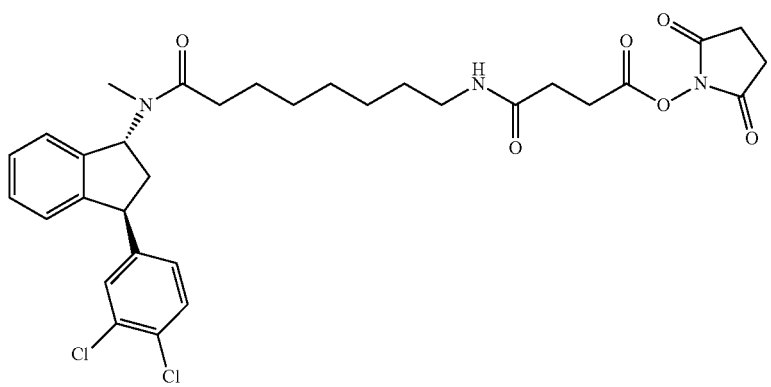 [SMILES: CN(C(=O)CCCCCCCNC(=O)CCC(=O)ON1C(=O)CCC1=O)[C@@H]1C[C@@H](c2ccc(Cl)c(Cl)c2)c2ccccc21]

The siRNA strand which is going to be attached to the selectivity agent is formed by step-wise solid phase synthesis on a solid support following the method disclosed in "Oligonucleotide synthesis, a practical approach." edited by M. J. Gait. IRL Press—1985.

In order to conjugate the selectivity agent, the oligonucleotide needs to be aminoderivatized. This can be done in the 5' or in the 3' end. In a preferred embodiment the selectivity agent is attached to the 5' end.

According to one embodiment of the synthesis of the invention, a conjugate according to the invention can be prepared by reacting the selectivity agent and an amino modified oligonucleotide of formula:

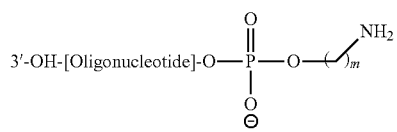

The general procedure for activating an oligonucleotide using an amino linker modifier will typically be according to the scheme below:

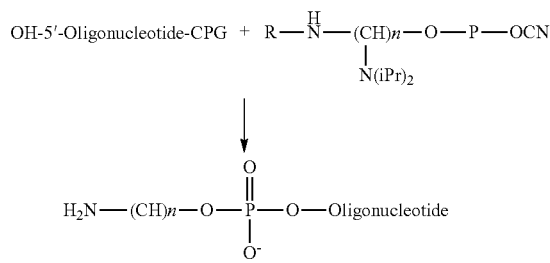

After coupling the 5'-OH group of the oligonucleotide to the amino linker, the amine protecting group is removed under known conditions. For example, TFA-protected amino-derivatives may be deprotected by treatment with ammonia; whereas MMT-protected amino-derivatives may be deprotected by treatment with acetic acid, chloroacetic acid, dichloroacetic acid or trifluoroacetic acid.

General method of synthesis of the aminomodified oligonucleotide:
(i) prepare a solution of linker/modifier molecule (vacuum dried) in anhydrous acetonitrile (0.1M solution is used in most of the commercially available amidites) and place it into an extra reservoir in the synthesizer (Y)
(ii) at the start of the synthesis of the required oligonucleotide sequence, add the Y base at the 5' end. This will enable the linker/modifier molecule from Y reservoir to couple at the end of the oligonucleotide sequence.
(iii) start the synthesis using the appropriate coupling cycle. The same coupling cycle will be used to carry out the linker/modifier molecule coupling.
(iv) at the end of the oligonucleotide synthesis, wash the support and finally dry the support with gas
(v) remove the solid support from the column and transfer it into a screw capped vial and complete the 2 step de-protection.

The aminomodified oligonucleotide should be deprotected for further conjugation with the selectivity agent. For this purpose all the remaining protecting groups in the oligonucleotide are removed as follows. 500 μl of a mixture containing 20% v/v of methylamine (aqueous solution 40% w/v) and 80% v/v of a saturated ammonia solution, (containing 30-32% w/v of $NH_3$) were added to an Eppendorf tube with the oligonucleotide (200 nmole scale). The tube was hermetically closed and heated for 45 minutes to a temperature of 65° C. This procedure eliminates the protecting groups in the phosphorous atom of the nucleotides (acetylation or benzoylation of the furanose and the 2-cyanoethylation of the phosphodiester linkages), and the protecting groups of the exocyclic amino groups (Bz, Ac, IBu). The mixture was then cooled and filtered and the supernatant was dried. The residual pellet was reacted with 1M triethylamine-HF for 3 hours at 65° C. to cleave the protecting groups at 2' of the nucleotides (2'-t-butyl dimethyl silyl—TBDMS). Finally, the resultant solution was desalted in a Sephadex column, leaving a aminomodified-5'-oligonucleotide.

In the case of incorporating the amino modifier linker in the 3'OH terminus; the corresponding polymer support (CPG balls) should be used and the synthesis scheme will correspond to the following diagram:

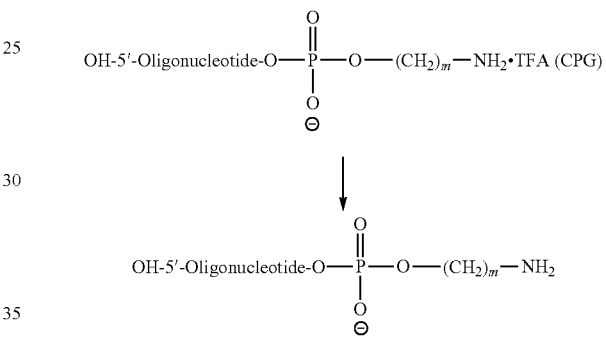

(the hydrolysis can be done by using ammonium hydroxide or Beckman reagent) (methyl amine:Ammonium hydroxide).

In both cases, the de-protection step will be identical and the conjugation approach in such event is also identical but with different degrees of efficiency. In most cases, better results are achieved with 5'-amino derivatization.

In a particular embodiment, the oligonucleotide is previously reacted with a bivalent or trivalent phosphoramide. In this way a compound with two or three coupling positions can be obtained, so that two or three molecules of selectivity agent can be coupled to the oligonucleotide. Said two or three molecules of selectivity agent can be similar or different.

In a particular embodiment two or three molecules of the same selectivity agent are coupled to the oligonucleotide. In another embodiment, two or three different selectivity agents are coupled to the oligonucleotide.

In an embodiment, the oligonucleotide is reacted with a bivalent or trivalent phosphoramidite.

Hydroxy protecting groups, as well as suitable protecting and deprotecting conditions, are known to the skilled person, for example in *Protecting Groups in Organic Synthesis* (Wuts, P. G. M. and Greene T. W., 4$^{th}$ Ed. Wiley-Interscience) and in *Protecting Groups* (Kocienski P. J., 3$^{rd}$ Ed. Georg Thieme Verlag).

In a particular embodiment, the hydroxy protecting groups are selected from ethers, silyl ethers, esters, sulfonates, sulfenates, sulfinates, carbonates and carbamates. In a preferred embodiment, the hydroxyl protecting groups are selected from acetyl, benzoyl, benzyl, methoxyethoxymethyl ether (MEM), dimethoxytrityl (DMT), methoxymethyl ether (MOM), methoxytrityl (MMT), p-methoxybenzyl ether (PMB), methylthiomethyl ether, pivaloyl (Piv), tetrahydropyranyl (THP), Trityl (Tr), 9H-fluorenylmethoxycarbonyl (Fmoc), trimethyl silyl (TMS), tert-butyldimethylsilyl (TBDMS), tert-butyldimethylsilyloxymethyl (TOM), and triisopropylsilyl (TIPS) ether. Preferably, PG, PG' and PG" are independently selected from H, DMT and Fmoc.

Synthesis Using an Carboxy-Derivatized Nucleic Acid and an Activated Triple Uptake Inhibitor In an alternative preferred embodiment, the conjugate of the invention is obtained by the conjugation of an amino-derivatized selectivity agent and a carboxyl-derivatized oligonucleotide. In particular, the conjugate of the invention has the structure (III):

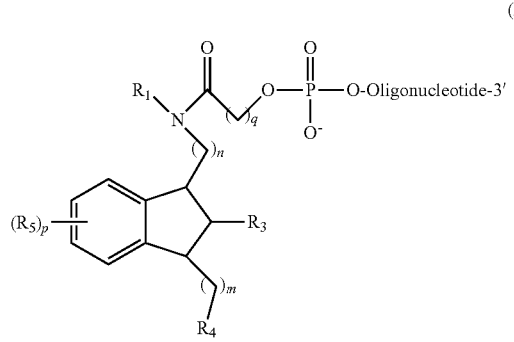

(III)

wherein
n or m are integers each having a value between 0 and 6, inclusive;
p is an integer having a value between 0 and 4, inclusive;
q is an integer having a value between 0 and 20 inclusive;
$R_1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-C(=O)R_A$; $-CO^2R_A$; $-C(=O)N(R_A)_2$ or $-C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_C$; $-C(=O)R_C$; $-CO_2R_C$; $-CN$; $-SCN$; $-SR_C$; $-SOR_C$; $SO_2R_C$; $-NO_2$; $-N_3$; $-N(R_C)_2$; $-NHC(=O)R_C$; $-NR_CC(=O)N(R_C)_2$; $-OC(=O)OR_C$; $-OC(=O)R_C$; $-OC(=O)N(R_C)_2$; $-NR_CC(=O)OR_C$; or $-C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is substituted or unsubstituted, branched or unbranched aryl; or substituted or unsubstituted, branched or unbranched heteroaryl;
$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_E$; $-C(=O)R_E$; $-CO_2R_E$; $-CN$; $-SCN$; $-SR_E$; $-SOR_E$; $SO_2R_E$; $-NO_2$; $-N_3$; $-N(R_E)_2$; $-NHC(=O)R_E$; $-NR_EC(=O)N(R_E)_2$; $-OC(=O)OR_E$; $-OC(=O)R_E$; $-OC(=O)N(R_E)_2$; $-NR_EC(=O)OR_E$; or $-C(R_E)_3$ wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable forms thereof;

and wherein the oligonucleotide is a nucleic acid which is capable of specifically binding to a target molecule wherein said target molecule is alpha-synuclein or the mRNA encoding α-synuclein.

The process of synthesis of a conjugate having the structure of (III) comprises reacting a compound having the structure of (V):

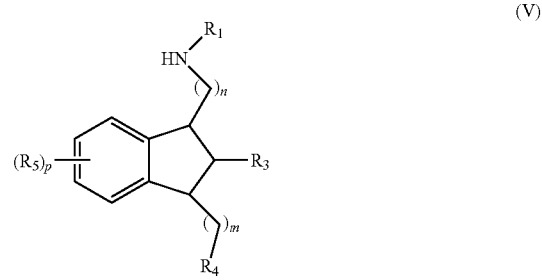

(V)

with a carboxymodified oligonucleotide having the formula (VI):

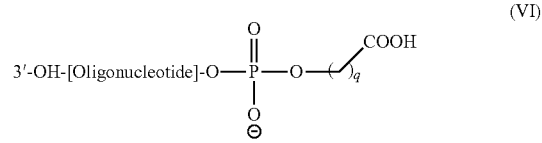

(VI)

Thus, the invention is also related to a compound having the structure (VI) wherein the oligonucleotide is a nucleic acid which is capable of specifically binding to a target molecule wherein said target molecule is alpha-synuclein or the mRNA encoding alpha-synuclein. In a particular embodiment, the oligonucleotide in the compound having the structure (VI) is an antisense gapmer. In particular, said gapmer comprises a central block of 10 deoxynucleotides flanked by blocks of 4 2'-Omethyl modified ribonucleotides.

In a particular embodiment, the oligonucleotide is targeted to a region in the alpha-synuclein mRNA selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7). In a preferred embodiment, the oligonucleotide in the compound having the structure (VI) consists of a sequence selected from the group consisting of SEQ ID NO:1, SEQ ID NO:2 or SEQ ID NO:3.

Commonly used protecting groups for amines include carbamates, such as tert-butyl, benzyl, 2,2,2-trichloroethyl, 2-trimethylsilylethyl, 9H-fluorenylmethoxycarbonyl (Fmoc), allyl or nitrophenyl carbamates; amides, such as formamides, acetamides, trifluoroacetamides, sulfonamides, trifluoromethanesulfonyl amides or tert-butylsulfonyl amides; and aryl or arylakylamines, such as p-methoxyphenyl, benzyl, p-methoxybenzyl, 3,4-dimethoxybenzyl, dimethoxytrityl or monomethoxytrityl amines. In a particular embodiment, the acylating agent of formula (VII) is 9H-fluorenylmethoxycarbonyl-6-aminohexanoic acid.

Suitable deprotecting conditions are known to the skilled person, for example in *Protecting Groups in Organic Synthesis* (Wuts, P. G. M. and Greene T. W., 4$^{th}$ Ed. Wiley-Interscience) and in *Protecting Groups* (Kocienski P. J., 3$^{rd}$ Ed. Georg Thieme Verlag). In a particular embodiment, the protecting group is removed in the presence of an amine, such as piperidine, morpholine, dicyclohexylamine, diisopropylethylamine or dimethylaminopyridine, preferably in the presence of piperidine.

The siRNA strand which is going to be attached to the selectivity agent is formed by step-wise solid phase synthesis on a solid support following the method disclosed in "Oligonucleotide synthesis, a practical approach." edited by M. J. Gait. IRL Press—1985.

In order to conjugate the selectivity ligand, the oligonucleotide needs to be carboxyderivatized. This can be done in the 5' or in the 3' end. In a preferred embodiment the selectivity ligand is attached to the 5' end.

According to one embodiment, the conjugates of formula (III) may be prepared by reacting a compound of formula (V) as described above and an carboxy-modified oligonucleotide of formula (VI).

The general procedure for activating an oligonucleotide using a carboxyl linker a modifier will typically be according to the scheme below:

(ii) at the start of the synthesis of the required oligonucleotide sequence, add the Y base at the 5'end. This will enable the linker/modifier molecule from Y reservoir to couple at the end of the oligonucleotide sequence.
(iii) start the synthesis using the appropriate coupling cycle. The same coupling cycle will be used to carry out the linker/modifier molecule coupling.
(iv) at the end of the oligonucleotide synthesis, wash the support and finally dry the support with gas
(v) remove the solid support from the column and transfer it into a screw capped vial and complete the 2 step de-protection.

The carboxymodified oligonucleotide should be deprotected for further conjugation with the selectivity agent. For this purpose all the remaining protecting groups in the oligonucleotide are removed as follows. 500 µl of a mixture containing 20% v/v of methylamine (aqueous solution 40% w/v) and 80% v/v of a saturated ammonia solution, (containing 30-32% w/v of NH$_3$) were added to an Eppendorf tube with the oligonucleotide (200 nmole scale). The tube was hermetically closed and heated for 45 minutes to a temperature of 65° C. This procedure eliminates the protecting groups in the phosphorous atom of the nucleotides (acetylation or benzoylation of the furanose and the 2-cyanoethylation of the phosphodiester linkages), and the protecting groups of the exocyclic amino groups (Bz, Ac, IBu). The mixture was then cooled and filtered and the supernatant was dried. The residual pellet was reacted with 1M triethylamine-HF for 3 hours at 65° C. to cleave the protecting groups at 2' of the nucleotides (2'-t-butyl dimethyl silyl—TBDMS). Finally, the resultant solution was desalted in a Sephadex column, leaving a carboxymodified-5'-oligonucleotide.

In a particular embodiment, the oligonucleotide comprised by the conjugate synthesized by the method of the invention is an antisense gapmer. In particular, the gapmer comprises a central block of 10 deoxynucleotides flanked by blocks of 4 2'-O-methyl modified ribonucleotides.

In a preferred embodiment, the oligonucleotide comprised by the conjugate synthesized by the method of the invention is targeted to a region in the alpha-synuclein mRNA selected from the group consisting of a region located at positions

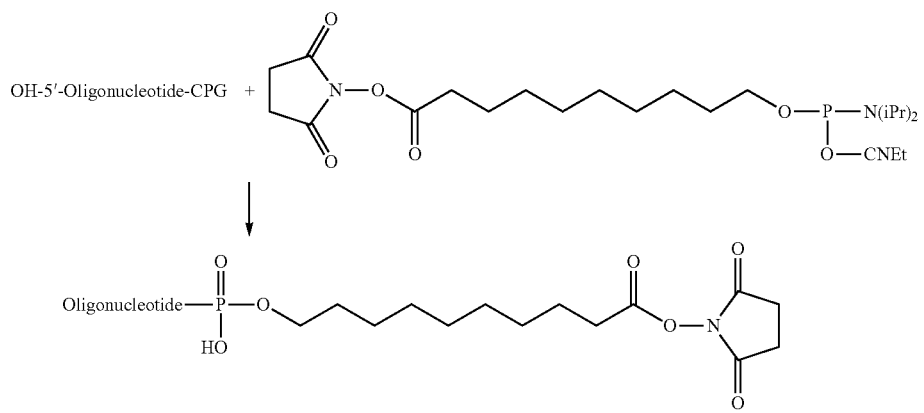

General method of synthesis of the carboxymodified oligonucleotide:

(i) prepare a solution of modifier molecule in anhydrous acetonitrile and place it into an extra reservoir in the synthesizer (Y)

448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7). In particular, the nucleic acid consists of a sequence selected from the group consisting of SEQ ID NO:1, SEQ ID NO:2 or SEQ ID NO:3.

The carboxyl-activated oligonucleotide is then reacted with the activated derivative of a selectivity agent of formula (V) as defined above. A compound is obtained having the general formula (III):

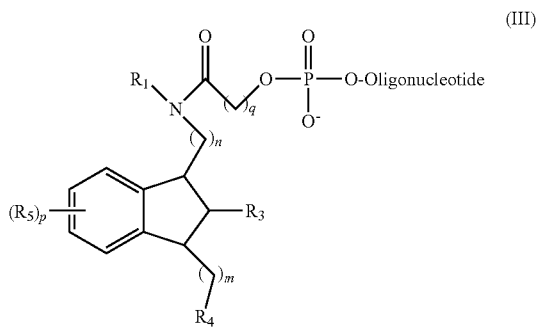

In particular, this compound (III) comprises an oligonucleotide which is capable of specifically binding to a target molecule wherein said target molecule is alpha-synuclein or the mRNA encoding alpha-synuclein. In a particular embodiment, the oligonucleotide in the compound having the structure (III) is an antisense gapmer. In particular, said gapmer comprises a central block of 10 deoxynucleotides flanked by blocks of 4 2'-O-methyl modified ribonucleotides.

In a particular embodiment, the oligonucleotide is targeted to a region in the alpha-synuclein mRNA selected from the group consisting of a region located at positions 448-465 (SEQ ID NO:4), 499-516 (SEQ ID NO:5) and 502-519 (SEQ ID NO:6) of the human alpha-synuclein mRNA wherein the numbering corresponds to the position with respect to the first nucleotide in the alpha-synucleic sequence as defined in NCBI accession number NM_000345 (SEQ ID NO:7). In a preferred embodiment, the oligonucleotide in the compound having the structure (III) consists of a sequence selected from the group consisting of SEQ ID NO:1, SEQ ID NO:2 and SEQ ID NO:3.

F. Diagnostic Conjugates and Uses Thereof

The possibility of specifically delivering a therapeutic compound to a target-cell by using selectivity agents capable of binding with high affinity to neurotransmitter transporters can also be applied for the delivery of compounds that can be used for diagnostic purposes. Thus, in another embodiment, the invention provides a conjugate comprising a
(i) at least one selectivity agent which binds specifically to one or more neurotransmitter transporters selected from the group consisting of a dopamine transporter (DAT), serotonin transporter (SERT) or a norepinephrine transporter (NET) and
(ii) an imaging agent.

The term "selectivity agent" and "neurotransmitter transporter" have been described in detail above and can be understood equally for the diagnostic conjugates of the invention.

The terms "imaging agent" and "contrast agent", are used herein interchangeably and refer to a biocompatible compound, the use of which facilitates the differentiation of different parts of the image, by increasing the "contrast" between those different regions of the image. The term "contrast agents" thus encompasses agents that are used to enhance the quality of an image that may nonetheless be generated in the absence of such an agent (as is the case, for instance, in MRI), as well as agents that are prerequisites for the generation of an image (as is the case, for instance, in nuclear imaging). Suitable contrast agents include, without limitation, contrast agents for Radionuclide imaging, for computerized tomography, for Raman spectroscopy, for Magnetic resonance imaging (MRI) and for optical imaging.

Contrast agents for radionuclide imaging include radiopharmaceuticals and are commonly labeled with positron-emitters such as $^{11}C$, $^{13}N$, $^{15}O$, $^{18}F$, $^{82}Rb$, $^{62}Cu$ and $^{68}Ga$. SPECT radiopharmaceuticals are commonly labeled with positron emitters such as $^{94}mTc$, $^{201}Tl$ and $^{67}Ga$. Radionuclide imaging modalities (positron emission tomography (PET); single photon emission computed tomography (SPECT)) are diagnostic cross-sectional imaging techniques that map the location and concentration of radionuclide-labeled radiotracers. PET and SPECT can be used to localize and characterize a radionuclide by measuring metabolic activity. PET and SPECT provide information pertaining to information at the cellular level, such as cellular viability. In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high. In certain embodiments of the invention, a cell is labeled ex vivo for PET or SPECT imaging in vivo. Closely related to PET is single-photon emission computed tomography, or SPECT. The major difference between the two is that instead of a positron-emitting substance, SPECT uses a radioactive tracer that emits low-energy photons.

Contrast agents for CT imaging include, for example, iodinated or brominated contrast media. Examples of these agents include iothalamate, iohexyl, diatrizoate, iopamidol, ethiodol and iopanoate. Gadolinium agents have also been reported to be of use as a CT contrast agent (see, e.g., Henson et al., 2004). For example, gadopentate agents has been used as a CT contrast agent (discussed in Strunk and Schild, 2004). Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth. In CT, intravenous injection of a radiopaque contrast agent such as those described herein can assist in the identification and delineation of soft tissue masses when initial CT scans are not diagnostic.

Contrast agents for optical imaging include, for example, fluorescein, a fluorescein derivative, indocyanine green, Oregon green, a derivative of Oregon green, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye and the various other fluorescent compounds disclosed herein.

In a preferred embodiment, the contrast agent is a compound that is able to be imaged by a magnetic resonance imaging apparatus. Contrast agents which can be imaged by a magnetic resonance imaging apparatus differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles. In one particular embodiment, the MRI contrast agent is $^{19}$F. Both CT and MRI provide anatomical information that aid in distinguishing tissue boundaries. Compared to CT, the disadvantages of MRI include lower patient tolerance, contraindications in pacemakers and certain other implanted metallic devices, and artifacts related to multiple causes, not the least of which is motion. CT, on the other hand, is fast, well tolerated, and readily available but has lower contrast resolution than MRI and requires iodinated contrast and ionizing radiation. A disadvantage of both CT and MRI is that neither imaging modality provides functional information at the cellular level. For example, neither modality provides information regarding cellular viability. Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

MRI contrast agents include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). In a preferred embodiment, the compound that is able to be imaged by a magnetic resonance imaging apparatus is a gadolinium-based compound.

The term "gadolinium-based compound", as used herein, shall mean, where used with respect to imaging, any gadolinium-containing substance administrable to a subject which results in an intravascular enhancement. In another embodiment, the gadolinium-containing contrast agent is selected from the group consisting of gadolinium, gadolinium pentate, and gadodiamide.

The amount of the gadolinium-containing contrast agent to be administered varies in an amount of about 10 mg per kg body weight. In another embodiment, the second magnetic resonance image is acquired about 45 minutes after administering the gadolinium-containing contrast agent. This invention also provides the above-described method further comprising the step of intraperitoneally administering a saline solution (e.g. Ringer's solution) to the subject, which administering follows either step (c) or step (d).

The invention also provides the use of a conjugate as defined above as diagnostic agent and methods for the detection of cells expressing the neurotransmitter transporter on their surface.

Diagnostic conjugates according to the invention comprise at least one selectivity agent which binds specifically to one or more neurotransmitter transporters selected from the group consisting of a DAT, SERT or NET and an imaging agent. In a particular embodiment, the selectivity agent is a triple blocker, more particularly, a triple reuptake inhibitor with the structure (I)

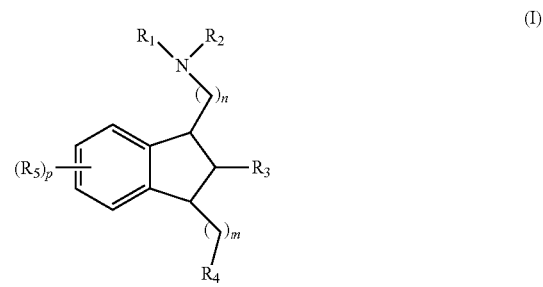

wherein
n or m are integers each having a value between 0 and 6, inclusive;
p is an integer having a value between 0 and 4, inclusive
$R_1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_A$; —CO$_2R_A$; —C(=O)N($R_A$)$_2$ or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_B$; —CO$_2R_B$; —C(=O)N($R_B$)$_2$ or —C($R_B$)$_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_C$; —C(=O)$R_C$; —CO$_2R_C$; —CN; —SCN; —S$R_C$; —SO$R_C$; SO$_2R_C$; —NO$_2$; —N$_3$; —N($R_C$)$_2$; —NHC(=O)$R_C$; —N$R_C$C(=O)N($R_C$)$_2$; —OC(=O)O$R_C$; —OC(=O)$R_C$; —OC(=O)N($R_C$)$_2$; —N$R_C$C(=O)O$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is substituted or unsubstituted, branched or unbranched aryl; or substituted or unsubstituted, branched or unbranched heteroaryl;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —$C(=O)R_E$; —$CO_2R_E$; —CN; —SCN; —$SR_E$; —$SOR_E$; $SO_2R_E$; —$NO_2$; —$N_3$; —$N(R_E)_2$; —$NHC(=O)R_E$; —$NR_EC(=O)N(R_E)_2$; —$OC(=O)OR_E$; —$OC(=O)R_E$; —$OC(=O)N(R_E)_2$; —$NR_EC(=O)OR_E$; or —$C(R_E)_3$ wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable forms thereof.

The invention also provides multimodal imaging methods. Certain embodiments of the present invention pertain to methods of imaging a subject, or a site within a subject using multiple imaging modalities that involve measuring multiple signals. In certain embodiments, the multiple signals result from a single label on, or in a cell. As set forth above, any imaging modality known to those of ordinary skill in the art can be applied in these embodiments of the present imaging methods.

The imaging modalities are performed at any time during or after administration of the labeled composition, e.g., labeled cell. For example, the imaging studies may be performed during administration of the labeled cell of the present invention, i.e., to aid in guiding the delivery to a specific location, or at any time thereafter.

Additional imaging modalities may be performed concurrently with the first imaging modality, or at any time following the first imaging modality. For example, additional imaging modalities may be performed about 1 sec, about 1 hour, about 1 day, or any longer period of time following completion of the first imaging modality, or at any time in between any of these stated times. In certain embodiments of the present invention, multiple imaging modalities are performed concurrently such that they begin at the same time following administration of the labeled cell or agent. One of ordinary skill in the art would be familiar with performance of the various imaging modalities contemplated by the present invention.

In some embodiments of the present methods of imaging, the same imaging device is used to perform a first imaging modality and a second imaging modality. In other embodiments, different imaging devices are used to perform the different imaging modalities. One of ordinary skill in the art would be familiar with the imaging devices that are available for performance of the imaging modalities described herein.

The instant invention provides methods for imaging cells using one or more imaging modalities. In some embodiments the cells are labeled with multiple imaging agents, and in other aspects the cells are labeled with a single labeling agent. In certain embodiments, the single labeling agent is a multimode-detectable agent.

G. Conjugates Comprising Liposomes and Dendrimers

In another embodiment, the invention provides conjugates wherein a liposome is coupled to one or more neurotransmitter transporters selected from the group consisting of a dopamine transporter (DAT), serotonintransporter (SERT) or a norepinephrine transporter (NET).

In another embodiment, the invention provides conjugates wherein a dendrimer is coupled to one or more neurotransmitter transporters selected from the group consisting of a dopamine transporter (DAT), serotonintransporter (SERT) or a norepinephrine transporter (NET).

By encapsulating a therapeutical compound within the dendrimer or liposome, the conjugates allows the selective delivery of said compound to cells which express said neurotransmitter transporter.

In a preferred embodiment, the selectivity agent is selected from the group consisting of a triple reuptake inhibitor, a noradrenaline dopamine double reuptake inhibitor, a serotonin single reuptake inhibitor, a noradrenaline single reuptake inhibitor and a dopamine single reuptake inhibitor. In a still more preferred embodiment, the selectivity agent is indatraline, a compound having the general formula

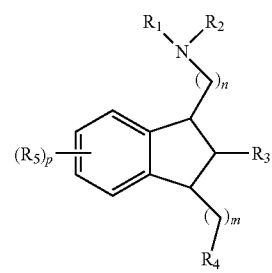

or a pharmaceutically active salt thereof, wherein n, m, p, $R_1$, $R_2$, $R_3$ $R_4$ and $R_5$ is as defined above.

Liposomes and nanoparticles are exemplary forms of nanocontainers that are commonly used for encapsulation of drugs. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol, along with a small amount (1 percent) of cationic lipid, such as didodecyldimethylammonium bromide (DDAB) to stabilize the DNA within the liposome.

The liposome can be replaced with a nanoparticle or any other molecular nanocontainer with a diameter less than 200 nm that can encapsulate the DNA and protect the nucleic acid from nucleases while the formulation is still in the blood or in transit from the blood to the intracellular compartment of the target cell. Also, instead of using conjugation agents such as PEG strands, one or more other polymeric substances, such as sphingomyelin, can be attached to the surface of the liposome or nanocontainer and serve the dual purpose of providing a scaffold for conjugation of the "transportable peptide" and for delaying the removal of the formulation from blood and optimizing the plasma pharmacokinetics. Further, the present invention contemplates delivery of DNA to any group of cells or organs which have specific target receptors. The liposomes may be used to deliver DNA to organs, such as liver, lung and spleen.

Other suitable containers for the delivery of the conjugates of the invention include dendrimers. The term "dendrimer" refers to a macromolecule having a core and having multiple shells of branching structures emanating from the core. The shape and size of a dendritic carrier can vary. In some instances, the dendritic carrier can be approximately spherical or globular in shape. Furthermore, the dendritic carrier can have a diameter in the range of about 15 angstroms (A) to about 250 A, with a corresponding range of molecular weights, e.g., from about 500 Daltons to about 2 million Daltons. Dendrimers can be obtained commercially from various sources (e.g., Dendritech, Midland, Mich.) or synthesized by methods known to those skilled in the art. Dendritic molecules can roughly be divided into the low-molecular weight and the high-molecular weight species. The first category includes dendrimers and dendrons whereas the second encompasses dendronized polymers, hyperbranched polymers, and brush-polymers (also called bottle-brushes). Dendrimers and dendrons are repeatedly branched, monodisperse, and usually highly symmetric compounds. There is no apparent difference in defining dendrimer and dendron. A dendron usually contains a single chemically addressable group that is called the focal point. Because of the lack of the molar mass distribution high-molar-mass dendrimers and dendrons are macromolecules but not polymers. The properties of dendrimers are dominated by the functional groups on the molecular surface. Dendritic encapsulation of functional molecules allows for the isolation of the active site, a structure that mimics the structure of active sites in biomaterials because dendritic scaffolds separate internal and external functions. For example, a dendrimer can be water-soluble when its end-group is a hydrophilic group, like a carboxyl group.

Dendrimers may be generally characterised by the following features: (i) an initiator core (I) which may have one or more reactive sites and be point-like or of significant size so as to effect the final topology of the dendrimer; (ii) one or more layers of branched repeating units attached to the initiator core; (iii) functional terminal groups, such as anionic or cationic groups, attached, optionally through linking groups, to the surface of the dendrimer.

Dendrimers contemplated herein may comprise lysine, or lysine analogue building units. The term "lysine analogue" refers to a molecule which has a single apex carboxyl group for attachment to the previous layer of building units, and two or three primary amine groups to which can be attached further building units, blocking groups, linkers or aryl acid groups. Examples of "lysine analogues" contemplated herein are described in PCT/AU2007/000352, for example glycyl-lys. In some particular examples, the dendrimer comprises only lysine or one type of lysine analogue as the building unit.

Other dendrimers contemplated herein include those comprising polyamidoamine (PAMAM), poly(etherhydroxylamine) (PEHAM) or polypropyleneimine building units. In particular examples thereof, the dendrimer has only polyamidoamine (PAMAM), poly(etherhydroxylamine) (PEHAM) or polypropyleneimine as the building unit.

The core moiety may contain only 1 point of attachment for a building unit or may contain 2, 3 or more points, which may or may not be further utilized for the attachment of building units. Typically, the point of attachment is a free amino group. Core moieties may consist of, comprise or be derived from a building unit or may be a molecule different to the building units. Exemplary core moieties are illustrated herein and described in PCT/AU2007/000352.

The liposomes and dendrimers may be combined with any suitable pharmaceutical carrier for intravenous administration. Intravenous administration of the composition is the preferred route since it is the least invasive. Other routes of administration are possible, if desired. Suitable pharmaceutically acceptable carriers include saline, Tris buffer, phosphate buffer, or any other aqueous solution. An appropriate dosage can be established by procedures well known to those of ordinary skill in the art.

The liposomes and dendrimers of the conjugates according to the invention may encapsulate any of the nucleic acids mentioned above which are capable of specifically targeting α-synuclein. In addition, the liposomes and dendrimers may also contain compounds which are adequate for the treatment of Parkinson's disease and which exert their action in the neurons which express the neurotransmitter receptors. Suitable drugs that can be incorporated in the dendrimers or liposomes according to the invention include Levodopa, a dopamine agonist, a MAO-B inhibitor, amantadine and an anticholinergic.

The following examples and drawings are provided by way of illustration, and are not intended to be limiting of the present invention.

EXAMPLES

Example 1

Targeting Validation: Function

Experimental Design

To determine functionally the targeting of the molecules according to the invention, an oligo anti-5HT1A with indatraline was used. The molecule was intra-nasally administrated to validate that indatraline targets raphe nuclei. Two different concentrations were tested (30 and 100 μg/mouse) and hypothermia after 8-OH-DPAT administration was assessed to determine functionally that 5-HT1A receptors in raphe were targeted. Basal temperature was determined 24 hours after intra-nasal administration of the molecule.

8-Hydroxy-2-(di-n-propylamino)tetralin (8-OH-DPAT) is a selective 5-HT1A agonist that induces hypothermia in mice by activating somatodendritic 5-HT1A autoreceptors in median raphe. By this assay, it was determined if the hypothermia induced by 8-OH-DPAT can be blocked by indatraline, if able to target raphe, and the oligo that blocks down 5-HT1A.

30 and 100 μg/mouse of molecule according to the invention was intra-nasally administered and 24 hours later basal temperature was measured. 8-OH-DPAT 1 mg/kg was administered intraperitoneally (i.p.) and temperature was measured 5, 15, 30, 60 and 120 minutes afterwards.

Results

It was observed that oligos targeted with indatraline are able to reach raphe intranasally and to knockdown the expression of 5-HT1A 24 hours after administration in single application (see FIG. 1). Both concentrations were able to block the temperature change caused by 8-OH-DPAT at a single dose, but 30 μg/mouse was chosen in the following experiments due to the standard administration of 4 days, allowing an accumulation of the oligo overtime.

Example 2

Targeting Validation: Localization

Experimental Design

To visualize whether substantia nigra, locus coeruleus and raphe were targeted, an intra-ventricular administration of indatraline-antisense labelled with the fluorophore Alexa488 was used. Indatraline is a non-selective monoamine transporter inhibitor that blocks the reuptake of dopamine, norepinephrine, and serotonin.

Dopamine transporter (DAT) expression is localized in dopaminergic neurons of the substantia nigra pars compacta (SNC).

Norepinephrine transporter (NET also known as solute carrier family 6 member 2, SLC6A2) expression is restricted to noradrenergic neurons in locus coeruleous (LC) and are not present on neurons that release dopamine or epinephrine.

Serotonin transporter (SERT) expression is primarily located in serotonergic neurons localized in raphe nuclei with high levels in dorsal raphe (DR).

For co-localization purposes tyrosine hydroxylase (TH) and tryptophan hydroxylase (TPH) were selected. TH catalyzes the rate limiting step in the synthesis of catecholamines and is highly expressed in SN and LC. TPH is involved in the synthesis of serotonin and in expressed in raphe.

Results

Single plane confocal images of the three areas of interest (SN, LC and DR) were taken. Direct fluorescence of indatraline-oligo-Alexa488 in green was performed, co-stained with anti-TH (Tyroxine Hydroxylase) for LC and SN, anti-TPH (Tryptophan Hydroxylase) for DR and DAPI for nuclear staining. Animals were sacrificed 1 hour and 24 hours after surgery, and a clear staining of the oligo was observed at 1 hour. No Alexa488 fluorescence was detected in other brain regions.

Single plane confocal images of the three areas at higher magnification showed that the cytoplasmic and intranuclear staining of the molecule colocalizing in neurons TH (SN and LC) and TPH (DR) was positive.

Thus, specific targeting of the molecule was observed 1 hour after administration only in the desired areas: SN, LC and DR in animals with intraventricular administration of oligos conjugated with indatraline, providing evidence that targeted oligos reached the desired areas and got internalized into neurons, reaching cytoplasm and nucleus.

Example 3

Candidate Selection

Experimental Design

A total of 7 pre-candidates molecules were selected by RNase H assay. The objective of this assay was to determine which of the seven oligonucleotides promotes the activity of this non-specific endonuclease that catalyzes the cleavage of mRNA.

To determine the knockdown of mRNA in vivo, in situ hybridization was performed in a total of five animals per analyzed molecule. The seven pre-candidates molecules were divided in two groups administrated in consecutive weeks. A total of 30 μg/mouse/day was administered during 4 consecutive days. Animals were sacrificed 24 hours after the last administration.

Results

Figure 2:
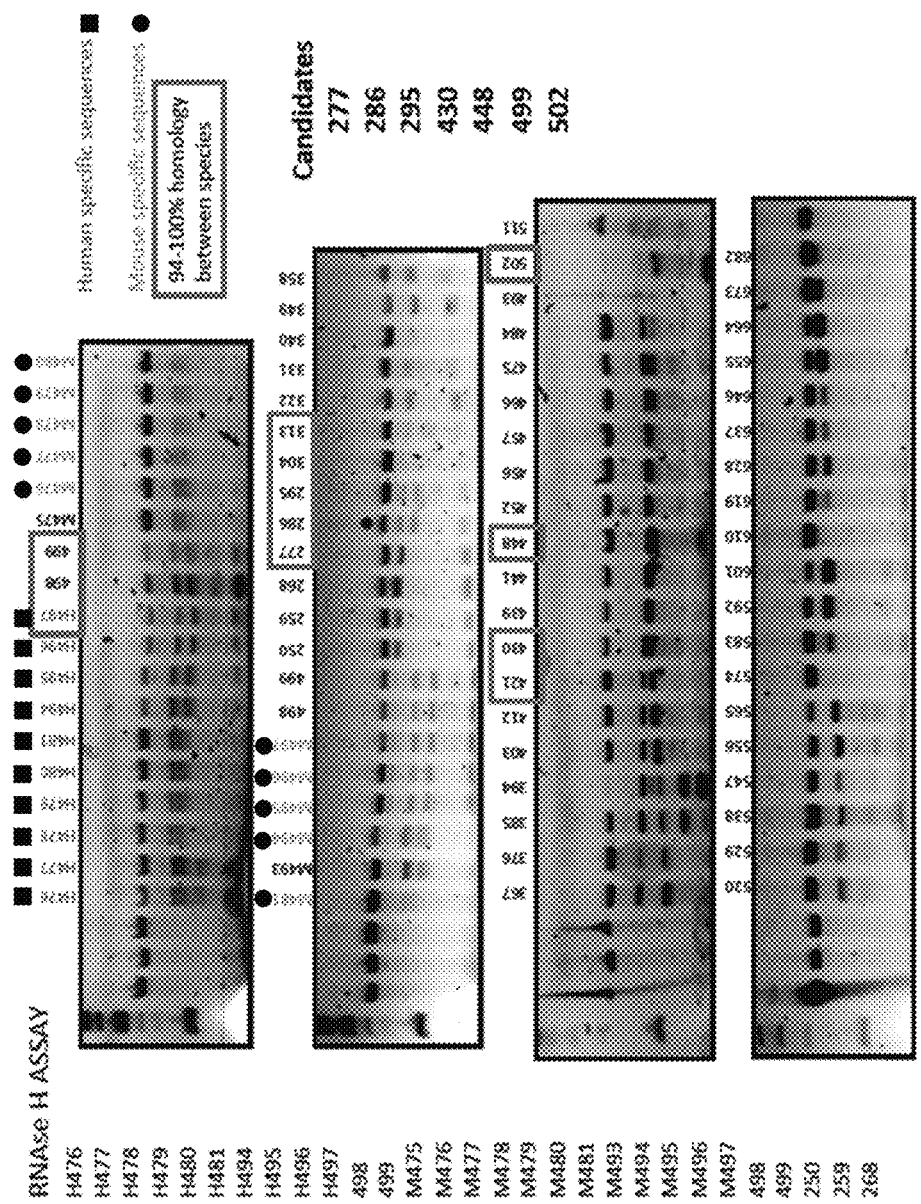
FIG. 2 shows an RNase H assay performed for candidate molecules selection. After in vitro transcription of human alpha synuclein mRNA, this mRNA was purified and subjected to an RNase H assay to measure the activity of individual sequences as potential inducers of the enzyme. In brief, mRNA (100 nM) was incubated in buffer with a 5-fold excess of the different molecules (500 nM) at 37° C. for 7.5 minutes. After that, reaction was stopped, samples run on an agarose gel and UV visualized. Sequences were either specific for human, mouse or both. Sequences selected (Candidates) were chosen regarding their ability to induce RNase H activity, their interspecies homology, and the lack of homology with beta and gamma synucleins.

FIG. 2 shows the results of the RNase H assay.

The following criteria were used during selection: selected candidates as shown in FIG. 2, a 94-100% homology between 5 species (mouse, rat, dog, monkey and human), no homology with other synucleins (gamma and beta) and induce of RNase H activity.

Figure 3:
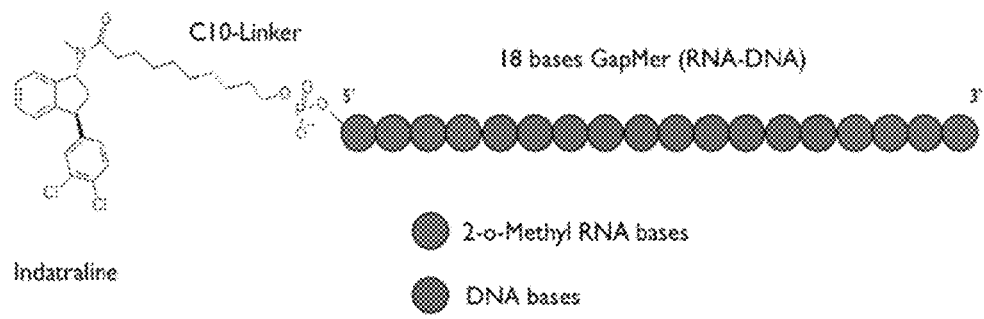
FIG. 3 shows an scheme of the conjugate according to the invention. It comprises indatraline as selectivity agent and a 18-bases gapmer, linked by a C10 linker.

To perform the in vivo studies, the final chemistry for the oligonucleotide was selected as described in the schema shown in FIG. 3.

Features of group I selected pre-candidates are shown in Table 1.

TABLE 1

Group-I pre-candidates

| ID# | Name | Target Nt gene | Species | Anti-sense sequence (5'3') | SEQ ID NO |
|---|---|---|---|---|---|
| 1232 | D-SNCA448-ASO4 | 18 SNCA | All | cuccAACATTTGTCacuu | 1 |
| 1233 | D-SNCA499-ASO4 | 18 SNCA | All | cuccCTCCACTGTCuucu | 2 |
| 1234 | D-SNCA502-ASO4 | 18 SNCA | All | cugcTCCCTCCACTgucu | 3 |

Figure 4:
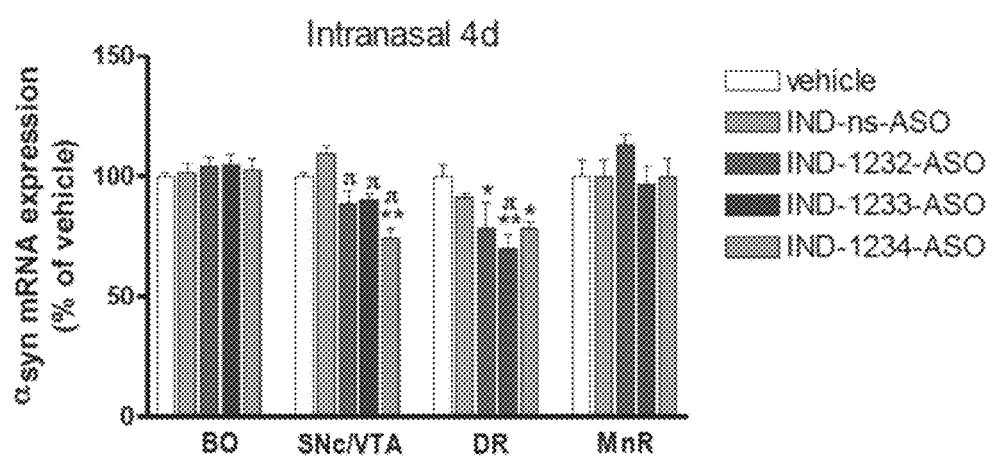
FIG. 4 shows the inhibition of alpha-synuclein mRNA expression by candidate molecules 1232, 1233 and 1234 according to the invention in olfactory bulbs (BO), substantia nigra (SNc/VTA), dorsal raphe (DR) and median raphe (MnR).

FIG. 4 shows the quantification of mRNA levels of α-synuclein (α-syn), calculated as percentage of vehicle, in olfactory bulbs (BO), substantia nigra (SNc/VTA), dorsal raphe (DR) and median raphe (MnR). it p<0.05 vs non-sense (IND-ns-ASO), *p<0.05 vs vehicle, **p<0.01 vs vehicle (two-way ANOVA).

It was observed that candidates 1232, 1233 and 1234 were able to decrease mRNA levels of α-synuclein in the targeted areas at a dose of 30 μg/mouse/day for 4 consecutive days without affecting levels in other brain areas. The highest decrease was observed in SN with the pre-candidate 1234 and raphe with the pre-candidate 1233.

Example 4

Toxicity

Experimental Design

It was also analyzed whether previously assayed molecules were able to induce IL-1β, IL-2, IL-6, IL-10, IFN-α, IFNγ, and TNFα secretion in human PBMCs (peripheral blood mononuclear cells). Compounds were tested as semi-log 6-point dilutions (10, 3.16, 1.0, 0.32, 0.1, and 0.03 μM concentrations). Effect of compounds on PBMC was tested in triplicate with alamarBlue cytotoxicity plate run in parallel.

Results

Table 2 shows that none of the molecules was able to induce an immune response in PBMCs.

TABLE 2

Immune response to the molecules under analysis

| | IFNα | IL-10 | IL-12p40 | IL-1β | IL-2 | IL-6 | INFγ | TNFα |
|---|---|---|---|---|---|---|---|---|
| | 6-Point Induction EC50 (μM) | | | | | | | |
| 1232-01 | N/A | N/A | N/A | N/A | N/A | N/A | N/A | N/A |
| 1233-01 | N/A | N/A | N/A | N/A | N/A | N/A | N/A | N/A |
| 1234-01 | N/A | N/A | N/A | N/A | N/A | N/A | N/A | N/A |

TABLE 2-continued

Immune response to the molecules under analysis

| | IFNα | IL-10 | IL-12p40 | IL-1β | IL-2 | IL-6 | INFγ | TNFα |
|---|---|---|---|---|---|---|---|---|
| | | | 6-Point Induction EMax (pg/mL) | | | | | |
| 1232-01 | 6.9 | 2.4 | 2.4 | 3.1 | 3.8 | 36 | 12 | 3.1 |
| 1233-01 | 12 | 2.4 | 2.4 | 2.5 | 3.6 | 28 | 12 | 3.5 |
| 1234-01 | 11 | 2.4 | 2.9 | 7.9 | 5.4 | 27 | 12 | 3.7 |
| Unstim. ctrl. 1 | 2.4 | 2.4 | 2.4 | 2.4 | 2.5 | 55 | 12 | 3.6 |
| Unstim. ctrl. 1 | 2.4 | 2.4 | 2.4 | 2.4 | 2.5 | 48 | 12 | 3.1 |
| Ref. comp. | 2.4 | 38 | 21 | 170 | 590 | 95 | 24 | 1100 |

Unstim. ctrl. 1: unstimulated control 1; Unstim. Ctrl. 2: unstimulated control 2.
Ref. comp.: reference compound Example 5

Further Candidate Selection

Experimental Design

Final selection was performed by assessing complementarity of the candidates sequences with several species including human. Species considered for further characterization were mouse, monkey and human. A BLAST analysis was performed by using genomic and transcriptomic databases for human and mouse, and by using the ref.seq.RNA database for monkey.

Results

It was observed that all three pre-candidates were 100% homologous to human and monkey α-synuclein.

In particular, pre-candidate molecule 1234 had a mismatch in nt2 for the mouse α-synuclein sequence but this did not affect its activity. Pre-candidate molecules 1232 and 1233 had no homology with any other human gene. Pre-candidate 1234 had some homology with 2 more genes. Special attention was required to putative off-target effects on syntaphilin. This gene is highly expressed in brain and also in SN in humans.

Figure 5:
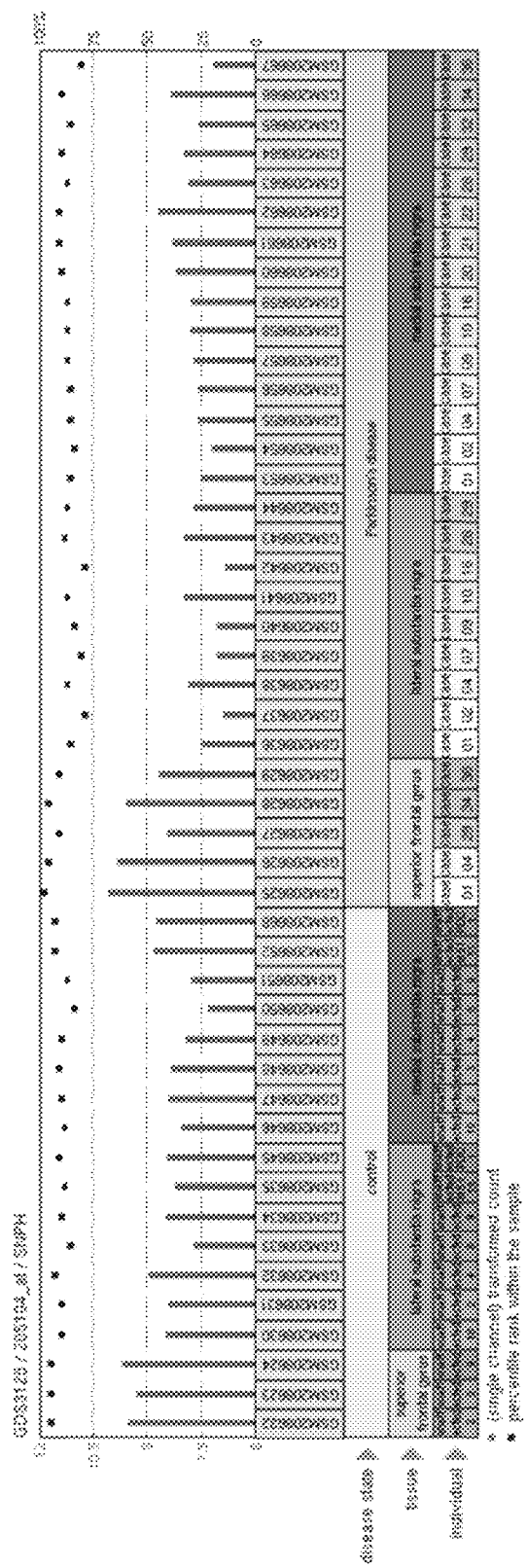
FIG. 5 shows an analysis of medial and lateral substantia nigras (SNs) from post-mortem brain samples obtained from individuals with sporadic Parkinson's disease (PD). The SN exhibits extensive tissue damage in PD. Results provide insight into the pathogenesis of PD.

FIG. 5 shows the analysis of a medial and lateral substantin nigras (SNs) from post-mortem brain samples obtained from individuals with sporadic Parkinson's disease (PD). The SN exhibits extensive tissue damage in PD.

Figure 6:
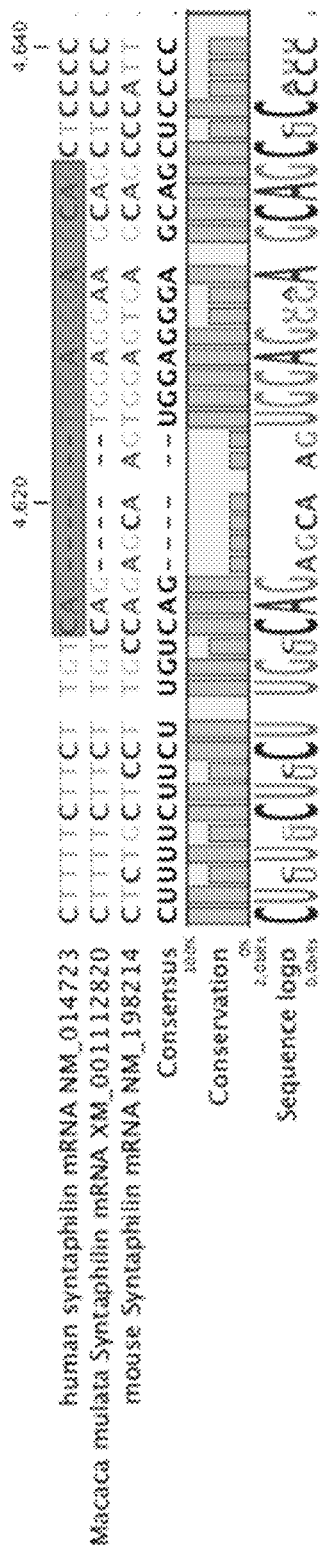
FIG. 6 shows an alignment of syntaphilin mRNA. Human, macaca mulata and mouse syntaphilin mRNAs were aligned with CLC sequence wiewer software and analyse to find out the putative homologies between them and candidate 1234-01 (the 15 nt of candidate 1234-01 common to α-synuclein mRNA in humans is shown in a box).

FIG. 6 shows the alignment of syntaphilin sequence for the tree species (the 15 nt of candidate 1234-01 common to α-synuclein mRNA in humans is shown in a box). This alignment showed that there is no homology with the mouse sequence, and that there is an internal mismatch in the monkey sequence at nt10, probably decreasing RNase H activity in monkey.

Figure 7:
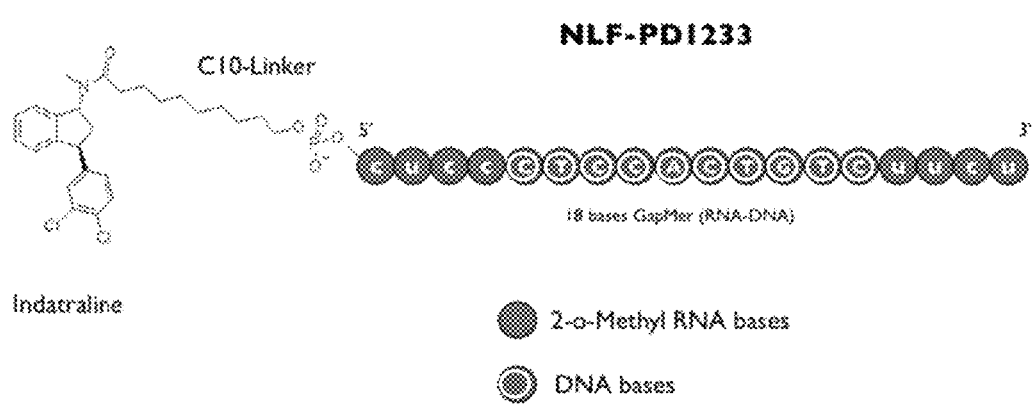
FIG. 7 shows an scheme of the preferred conjugate molecule according to the invention.

Considering all these data, the inventors of the present invention selected molecule #1233 as the best candidate, with sequence: cuccCTCCACTGTCuucu, as shown in FIG. 7.

The invention claimed is:

1. A conjugate comprising
   (i) at least one selectivity agent which binds specifically to one or more neurotransmitter transporters selected from the group consisting of a dopamine transporter (DAT), a serotonin transporter (SERT), and a norepinephrine transporter (NET) and
   (ii) at least one nucleic acid which is capable of specifically binding to a target molecule which is expressed in the same cell as the neurotransmitter transporter wherein said target molecule is a mRNA encoding α-synuclein, wherein the nucleic acid which is capable of specifically binding to said mRNA is targeted to a region located at positions 499-516 (SEQ ID NO:5) of the human α-synuclein mRNA, wherein the numbering corresponds to the position with respect to the first nucleotide in the α-synuclein sequence as defined in NCBI accession number NM 000345 (SEQ ID NO: 7).

2. The conjugate according to claim 1 wherein the binding of the nucleic acid to the target molecule results in an inhibition of the activity of α-synuclein or in the silencing of the mRNA encoding α-synuclein.

3. The conjugate according to claim 1 wherein the selectivity agent is selected from the group consisting of a triple reuptake inhibitor, a noradrenaline dopamine double reuptake inhibitor, a serotonin single reuptake inhibitor, a noradrenaline single reuptake inhibitor, and a dopamine single reuptake inhibitor.

4. The conjugate according to claim 3 wherein the selectivity agent is a triple reuptake inhibitor having the following structure (I)

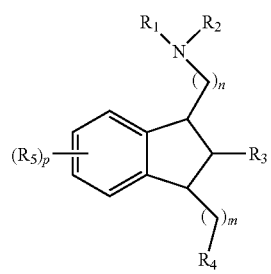

wherein
   n or m are integers each having a value between 0 and 6, inclusive;
   p is an integer having a value between 0 and 4, inclusive;
   $R_1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_4$; —CO$_2R_4$; —C(=O)N($R_4$)$_2$ or —C($R_4$)$_3$; wherein each occurrence of $R_4$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; $R_2$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_B$; —CO$_2R_B$; —C(=O)N($R_B$)$_2$ or —C($R_B$)$_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_C$; —C(=O)$R_C$; —CO$_2R_C$; —CN; —SCN; —S$R_C$; —SO$R_C$; SO$_2R_C$; —NO$_2$; —N$_3$; —N($R_C$)$_2$; —NHC(=O)$R_C$; —N$R_C$C(=O)N($R_C$)$_2$; —OC(=O) O$R_C$; —OC(=O)$R_C$; —OC(=O)N($R_C$)$_2$; —N$R_C$C (=O)O$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is substituted or unsubstituted, branched or unbranched aryl; or substituted or unsubstituted, branched or unbranched heteroaryl;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_E$; —C(=O)$R_E$; —CO$_2R_E$; —CN; —SCN; —S$R_E$; —SO$R_E$; SO$_2R_E$; —NO$_2$; —N$_3$; —N($R_E$)$_2$; —NHC(=O)$R_E$; —N$R_E$C(=O)N($R_E$)$_2$; —OC(=O) O$R_E$; —OC(=O)$R_E$; —OC(=O) N($R_E$)$_2$; —N$R_E$C (=O)O$R_E$; or —C($R_E$)$_3$ wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

and pharmaceutically acceptable forms thereof.

5. The conjugate according to claim 4 wherein the triple reuptake inhibitor has the structure (II)

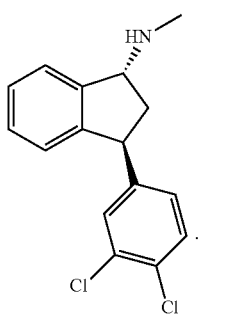

(II)

6. The conjugate according to claim 1 wherein the nucleic acid which is capable of specifically binding to a target molecule which is expressed in the same cell as the neurotransmitter transporter is selected from the group consisting of a gapmer, double stranded interference RNA, an antisense oligonucleotide, a mRNA coding for shRNAs, a PNA, a LNA, a ribozyme, and an aptamer.

7. The conjugate according to claim 6 wherein the nucleic acid is an antisense oligonucleotide or a gapmer.

8. The conjugate according to claim 7 wherein the gapmer comprises a central block of 10 deoxynucleotides flanked by blocks of 4 2'—O-methyl modified ribonucleotides.

9. The conjugate according to claim 7 wherein the selectivity agent is conjugated to the 5' end of the nucleic acid.

10. The conjugate according to claim 7 further comprising a second selectivity agent which binds specifically to one or more neurotransmitter transporters selected from the group consisting of a dopamine transporter (DAT), a serotonin transporter (SERT), and a norepinephrine transporter (NET), and wherein the first and second selectivity agent are the same or different.

11. The conjugate according to claim 10 wherein the first selectivity agent and the second selectivity agent bind specifically to different neurotransmitter transporters.

12. The conjugate according to claim 6 wherein the nucleic acid is interfering RNA and is a siRNA or a shRNA.

13. The conjugate according to claim 10 wherein the second selectivity agent is connected:

(i) to the opposite end of the nucleic acid which is connected to the first selectivity agent, (ii) to one end of nucleic acid which is complementary to the nucleic acid which is connected to the first selectivity agent and/or (iii) to the same end of the nucleic acid which is connected to the first selectivity agent by virtue of a polyfunctional linker attached to said end.

14. The conjugate according to claim 1 wherein the selectivity agent and the nucleic acid are connected by a linking group.

15. The conjugate according to claim 14 wherein the linking group has the structure

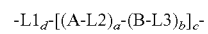

wherein:

A and B represent monomer units independently selected from the group consisting of a monosaccharide, a ($C_1$-$C_{50}$) alkyl, and a ($C_2C_{20}$) alkylene glycol;

a and b are integers ranging from 0 to 50;

c is an integer ranging from 0 and 30;

L1, L2 and L3 are linking compounds independently selected from the group consisting of phosphodiester, phosphorothioate, carbonyl, carbamate, methylphosphonate, guanidinium, sulfamate, sulfamide, formacetal, thioformacetal, sulfone, amide and mixtures thereof;

d is 0 or 1.

16. The conjugate according to claim 15 wherein b and d are 0, c is 1, A is an alkyl chain and L2 is a phosphodiester.

17. The conjugate according to claim 1 further comprising a protecting group attached to the end or ends of the nucleic acid which is not attached to the selectivity agent.

18. The conjugate according to claim 4 wherein the conjugate has the structure (III)

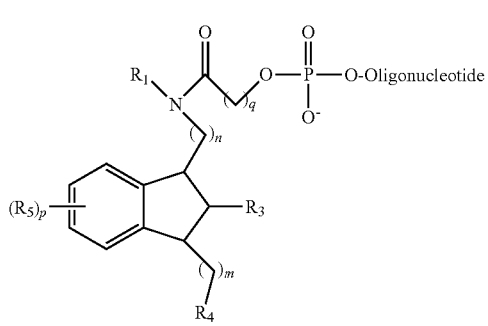

wherein the oligonucleotide is a nucleic acid which is capable of specifically binding to a target molecule and wherein q is an integer having a value between 0 and 20 inclusive and pharmaceutically acceptable forms thereof.

19. The conjugate according to claim 18 having the structure (IV)

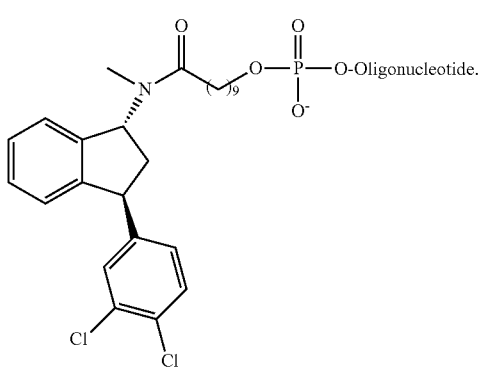

20. A conjugate comprising
(i) at least one selectivity agent which binds specifically to one or more neurotransmitter transporters selected from the group consisting of a dopamine transporter (DAT), serotonin transporter (SERT), and a norepinephrine transporter (NET) and
(ii) a nanotransporter comprising a nucleic acid which is capable of specifically binding to a target molecule which is expressed in the same cell as the neurotransmitter transporter wherein said target molecule is a mRNA encoding α-synuclein and the nucleic acid which is capable of specifically binding to said mRNA is targeted to a region located at positions 499-516 (SEQ ID NO:5) of the human α-synuclein mRNA, wherein the numbering corresponds to the position with respect to the first nucleotide in the α-synuclein sequence as defined in NCBI accession number NM 000345 (SEQ ID NO: 7), and wherein said nanotransporter is a liposome or a dendrimer.

21. A method for the treatment of a disorder associated with the deposition of Lewy bodies in a subject in need thereof, comprising administering to the subject a therapeutically effective amount of the conjugate of claim 1.

22. The method according to claim 21 wherein the disease associated with the deposition of Lewy bodies is selected from the group consisting of: Parkinson's disease, dementia with Lewy bodies and multiple system atrophy.

23. The method according to claim 21 wherein the conjugate is administered intraventricularly, intrathecally, or intranasally.

* * * * *

SEQUENCE LISTING

<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: Gapmer targeted to region 448-465 of alpha-synuclein mRNA

<400> SEQUENCE: 1
cuccaacatt tgtcacuu                                              18

<210> SEQ ID NO 2
<211> LENGTH: 18
<212> TYPE: DNA
<213> ORGANISM: Artificial Sequence
<220> FEATURE:
<223> OTHER INFORMATION: Gapmer targeted to region 499-516 of alpha-synuclein mRNA

<400> SEQUENCE: 2
cuccctccac tgtcuucu                                              18

<210> SEQ ID NO 3
<211> LENGTH: 18
<212> TYPE: DNA
<213> ORGANISM: Artificial Sequence
<220> FEATURE:
<223> OTHER INFORMATION: Gapmer targeted to region 502-519 of alpha-synuclein mRNA

<400> SEQUENCE: 3
cugctccctc cactgucu                                              18

<210> SEQ ID NO 4

```
<211> LENGTH: 18
<212> TYPE: DNA
<213> ORGANISM: Homo sapiens

<400> SEQUENCE: 4
aagtgacaaa tgttggag                                                   18

<210> SEQ ID NO 5
<211> LENGTH: 18
<212> TYPE: DNA
<213> ORGANISM: Homo sapiens

<400> SEQUENCE: 5
agaagacagt ggagggag                                                   18

<210> SEQ ID NO 6
<211> LENGTH: 18
<212> TYPE: DNA
<213> ORGANISM: Homo sapiens

<400> SEQUENCE: 6
agacagtgga gggagcag                                                   18

<210> SEQ ID NO 7
<211> LENGTH: 3215
<212> TYPE: DNA
<213> ORGANISM: Homo sapiens

<400> SEQUENCE: 7
aggagaagga gaaggaggag gactaggagg aggaggacgg cgacgaccag aaggggccca       60
agagaggggg cgagcgaccg agcgccgcga cgcggaagtg aggtgcgtgc gggctgcagc      120
gcagaccccg gccggcccc tccgagagcg tcctgggcgc tccctcacgc cttgccttca      180
agccttctgc ctttccaccc tcgtgagcgg agaactggga gtggccattc gacgacagtg      240
tggtgtaaag gaattcatta gccatggatg tattcatgaa aggactttca aaggccaagg      300
agggagttgt ggctgctgct gagaaaacca acagggtgt ggcagaagca caggaaaga       360 caaaagaggg tgttctctat gtaggctcca aaaccaagga gggagtggtg catggtgtgg      420
caacagtggc tgagaagacc aaagagcaag tgacaaatgt tggaggagca gtggtgacgg      480
gtgtgacagc agtagcccag aagacagtgg agggagcagg gagcattgca gcagccactg      540
gctttgtcaa aaaggaccag ttgggcaaga atgaagaagg agccccacag gaaggaattc      600
tggaagatat gcctgtggat cctgacaatg aggcttatga aatgccttct gaggaagggt      660
atcaagacta cgaacctgaa gcctaagaaa tatctttgct cccagtttct tgagatctgc      720
tgacagatgt tccatcctgt acaagtgctc agttccaatg tgcccagtca tgacatttct      780
caaagttttt acagtgtatc tcgaagtctt ccatcagcag tgattgaagt atctgtacct      840
gcccccactc agcatttcgg tgcttccctt tcactgaagt gaatacatgg tagcagggtc      900
tttgtgtgct gtggatttg tggcttcaat ctacgatgtt aaaacaaatt aaaaacacct      960
aagtgactac cacttatttc taaatcctca ctatttttt gttgctgttg ttcagaagtt     1020
gttagtgatt tgctatcata tattataaga ttttaggtg tctttaatg atactgtcta     1080 agaataatga cgtattgtga aatttgttaa tatatataat acttaaaaat atgtgagcat     1140
gaaactatgc acctataaat actaaatatg aaattttacc attttgcgat gtgttttatt     1200
cacttgtgtt tgtatataaa tggtgagaat taaaataaaa cgttatctca ttgcaaaaat     1260
attttatttt tatcccatct cactttaata ataaaaatca tgcttataag caacatgaat     1320
```

```
taagaactga cacaaaggac aaaaatataa agttattaat agccatttga agaaggagga      1380 atttagaag aggtagagaa aatggaacat taaccctaca ctcggaattc cctgaagcaa      1440
cactgccaga agtgtgtttt ggtatgcact ggttccttaa gtggctgtga ttaattattg      1500
aaagtggggt gttgaagacc ccaactacta ttgtagagtg gtctatttct cccttcaatc      1560
ctgtcaatgt ttgcttacg tattttgggg aactgttgtt tgatgtgtat gtgtttataa       1620
ttgttataca ttttaattg agccttttat taacatatat tgttattttt gtctcgaaat     1680
aattttttag ttaaaatcta ttttgtctga tattggtgtg aatgctgtac ctttctgaca      1740
ataaataata ttcgaccatg aataaaaaaa aaaaaaagt gggttcccgg gaactaagca      1800
gtgtagaaga tgattttgac tacaccctcc ttagagagcc ataagacaca ttagcacata      1860
ttagcacatt caaggctctg agagaatgtg gttaactttg tttaactcag cattcctcac      1920
tttttttttt taatcatcag aaattctctc tctctctctc tcttttctc tcgctctctt      1980 ttttttttt ttttacagg aaatgccttt aaacatcgtt ggaactacca gagtcacctt       2040
aaaggagatc aattctctag actgataaaa atttcatggc ctcctttaaa tgttgccaaa      2100
tatatgaatt ctaggatttt tccttaggaa aggtttttct ctttcaggga agatctatta      2160
actccccatg ggtgctgaaa ataaacttga tggtgaaaaa ctctgtataa attaatttaa      2220
aaattatttg gttctctttt ttaattattc tggggcatag tcatttctaa aagtcactag      2280
tagaaagtat aatttcaaga cagaatattc tagacatgct agcagtttat atgtattcat      2340
gagtaatgtg atatatattg ggcgctggtg aggaaggaag gaggaatgag tgactataag      2400
gatggttacc atagaaactt ccttttttac ctaattgaag agagactact acagagtgct      2460
aagctgcatg tgtcatctta cactagagag aaatggtaag tttcttgttt tatttaagtt      2520
atgtttaagc aaggaaagga tttgttattg aacagtatat ttcaggaagg ttagaaagtg      2580
gcggttagga tatattttaa atctacctaa agcagcatat tttaaaaatt taaaagtatt      2640
ggtattaaat taagaaatag aggacagaac tagactgata gcagtgaccct agaacaattt     2700 gagattagga aagttgtgac catgaattta aggatttatg tggatacaaa ttctcctta       2760 aagtgtttct tcccttaata tttatctgac ggtaattttt gagcagtgaa ttactttata      2820
tatcttaata gtttatttgg gaccaaacac ttaaacaaaa agttctttaa gtcatataag      2880 cctttttcagg aagcttgtct catattcact cccgagacat tcacctgcca agtggcctga     2940
ggatcaatcc agtcctaggt ttattttgca gacttacatt ctcccaagtt attcagcctc      3000
atatgactcc acggtcggct ttaccaaaac agttcagagt gcactttggc acacaattgg      3060
gaacagaaca atctaatgtg tggtttggta ttccaagtgg ggtcttttc agaatctctg       3120 cactagtgtg agatgcaaac atgtttcctc atctttctgg cttatccagt atgtagctat      3180
ttgtgacata ataaatatat acatatatga aaata                                 3215
```

<210> SEQ ID NO 8
<211> LENGTH: 21
<212> TYPE: DNA
<213> ORGANISM: Artificial Sequence
<220> FEATURE:
<223> OTHER INFORMATION: siRNA targeted to region 499-517 of alpha-
      synuclein (sense strand)

<400> SEQUENCE: 8
agaagacagu ggagggagct t                                                 21

```
<210> SEQ ID NO 9
<211> LENGTH: 21
<212> TYPE: DNA
<213> ORGANISM: Artificial Sequence
<220> FEATURE:
<223> OTHER INFORMATION: siRNA targeted to region 499-517 of alpha-
      synuclein mRNA (antisense strand)

<400> SEQUENCE: 9
gcucccucca cugucuucut t                                                21

<210> SEQ ID NO 10
<211> LENGTH: 110
<212> TYPE: DNA
<213> ORGANISM: Homo sapiens

<400> SEQUENCE: 10
ttggatgttg gcctagttct gtgtggaaga ctagtgattt tgttgttttt agataactaa      60
atcgacaaca aatcacagtc tgccatatgg cacaggccat gcctctacag                110

<210> SEQ ID NO 11
<211> LENGTH: 110
<212> TYPE: DNA
<213> ORGANISM: Homo sapiens

<400> SEQUENCE: 11
ctggatacag agtggaccgg ctggccccat ctggaagact agtgattttg ttgttgtctt      60
actgcgctca acaacaaatc ccagtctacc taatggtgcc agccatcgca                110

<210> SEQ ID NO 12
<211> LENGTH: 110
<212> TYPE: DNA
<213> ORGANISM: Homo sapiens

<400> SEQUENCE: 12
agattagagt ggctgtggtc tagtgctgtg tggaagacta gtgattttgt tgttctgatg      60
tactacgaca acaagtcaca gccggcctca tagcgcagac tcccttcgac                110

<210> SEQ ID NO 13
<211> LENGTH: 90
<212> TYPE: DNA
<213> ORGANISM: Homo sapiens

<400> SEQUENCE: 13
ctcacagctg ccagtgtcat ttttgtgatc tgcagctagt attctcactc cagttgcata      60
gtcacaaaag tgatcattgg caggtgtggc                                       90

<210> SEQ ID NO 14
<211> LENGTH: 87
<212> TYPE: DNA
<213> ORGANISM: Homo sapiens

<400> SEQUENCE: 14
agcggtggcc agtgtcattt ttgtgatgtt gcagctagta atatgagccc agttgcatag      60
tcacaaaagt gatcattgga aactgtg                                          87

<210> SEQ ID NO 15
<211> LENGTH: 22
<212> TYPE: RNA
<213> ORGANISM: Homo sapiens

<400> SEQUENCE: 15
```

```
uggaagacua gugauuuugu ug                                              22

<210> SEQ ID NO 16
<211> LENGTH: 22
<212> TYPE: RNA
<213> ORGANISM: Homo sapiens

<400> SEQUENCE: 16
uugcauaguc acaaaaguga uc                                              22

<210> SEQ ID NO 17
<211> LENGTH: 7
<212> TYPE: PRT
<213> ORGANISM: Homo sapiens

<400> SEQUENCE: 17

His Ala Ile Tyr Pro Arg His
1               5

<210> SEQ ID NO 18
<211> LENGTH: 12
<212> TYPE: PRT
<213> ORGANISM: Homo sapiens

<400> SEQUENCE: 18

Thr His Arg Pro Pro Met Trp Ser Pro Val Trp Pro
1               5                   10
```